US012686866B2

(12) United States Patent (10) Patent No.: US 12,686,866 B2
Kaser et al. (45) Date of Patent: Jul. 21, 2026

(54) METHODS OF TREATING CANCER BY SUPPRESSION OF FAMIN EXPRESSION

(71) Applicant: Cambridge Enterprise Limited, Cambridge (GB)

(72) Inventors: Arthur Kaser, Cambridge (GB); Mohammed Zaeem Cader, Cambridge (GB)

(73) Assignee: CAMBRIDGE ENTERPRISE LIMITED, Cambridge (GB)

( * ) Notice: Subject to any disclaimer, the term of this patent is extended or adjusted under 35 U.S.C. 154(b) by 252 days.

(21) Appl. No.: 17/312,362

(22) PCT Filed: Dec. 9, 2019

(86) PCT No.: PCT/EP2019/084265
§ 371 (c)(1),
(2) Date: Jun. 9, 2021

(87) PCT Pub. No.: WO2020/120410
PCT Pub. Date: Jun. 18, 2020

(65) Prior Publication Data
US 2022/0017900 A1 Jan. 20, 2022

(30) Foreign Application Priority Data

Dec. 10, 2018 (GB) ...................................... 1820098

(51) Int. Cl.
| | |
|---|---|
| *C12N 15/113* | (2010.01) |
| *A61K 31/52* | (2006.01) |
| *A61K 31/708* | (2006.01) |
| *A61K 35/17* | (2025.01) |
| *A61K 38/46* | (2006.01) |
| *A61K 40/11* | (2025.01) |
| *A61K 40/42* | (2025.01) |
| *A61K 40/46* | (2025.01) |
| *A61K 45/06* | (2006.01) |

(52) U.S. Cl.
CPC ............ *C12N 15/113* (2013.01); *A61K 31/52* (2013.01); *A61K 31/708* (2013.01); *A61K 35/17* (2013.01); *A61K 38/465* (2013.01); *A61K 40/11* (2025.01); *A61K 40/42* (2025.01); *A61K 40/46* (2025.01); *A61K 45/06* (2013.01); *A61K 2239/31* (2023.05); *A61K 2239/38* (2023.05); *C12N 2310/11* (2013.01); *C12N 2310/14* (2013.01); *C12N 2310/20* (2017.05); *C12N 2310/531* (2013.01)

(58) Field of Classification Search
CPC .............. C12N 15/113; C12N 2310/11; C12N 2310/14; C12N 2310/531; A61K 31/713; A61P 35/00
See application file for complete search history.

(56) References Cited

U.S. PATENT DOCUMENTS

| | | |
|---|---|---|
| 12,331,343 B2 | 6/2025 | Kaser et al. |
| 2005/0101571 A1 | 5/2005 | Jolivet |
| 2022/0017943 A1 | 1/2022 | Kaser et al. |

FOREIGN PATENT DOCUMENTS

| | | |
|---|---|---|
| CA | 2005205 A1 | 6/1990 |
| CA | 3019628 A1 | 10/2017 |
| WO | 2020/120406 A1 | 6/2020 |
| WO | 2020/120410 A1 | 6/2020 |

OTHER PUBLICATIONS

Assadi et al., Dec. 13, 2016, "Functional Analyses of the Crohn's Disease Risk Gene LACC1", PLOS One, 11(12): e0168276 (Year: 2016).*
Assadi et al., Dec. 13, 2016, "Functional Analyses of the Crohn's Disease Risk Gene LACC1", PLOS ONE, DOI: 10.1371/journal. pone.0168276 (Year: 2016).*
Cader et al., Sep. 2016, "C13orf31 (FAMIN) is a central regulator of immunometabolic function", Nature Immunology, vol. 17, No. 9, p. 1046-1060 (Year: 2016).*
Lahiri et al., Jun. 8, 2017, "Human LACC1 increases innate receptor-induced responses and a LACC1 disease-risk variant modulates these outcomes", Nature Communications, 8:151614, DOI: 10.1038/ncomms 15614 (Year: 2017).*
Aartsma-Rus et al., 2009, "Guidelines for Antisense Oligonucleotide Design and Insight Into Splice-modulating Mechanisms", Molecular Therapy, vol. 17, No. 3, p. 548-553 (Year: 2009).*
Dang et al., Sep. 29, 2018, "New insights into molecular mechanisms of rosiglitazone in monotherapy or combination therapy against cancers", Chemico-Biological Interactions, 296 (2018), p. 162-170 (Year: 2018).*
Nakajima et al., 2015, "Adenosine Deaminase Inhibitor EHNA Exhibits a Potent Anticancer Effect Against Malignant Pleural Mesothelioma", Cellular Physiology and Biochemistry, 2015;35:51-60 (Year: 2015).*
Reynolds et al., 2012, "A Phase III trial of fludarabine, cyclophosphamide, and rituximab vs. pentostatin, cyclophosphamide, and rituximab in B-cell chronic lymphocytic leukemia", Invest New Drugs, (2012) 30: 1232-1240 (Year: 2012).*

(Continued)

*Primary Examiner* — Soren Harward
*Assistant Examiner* — Jenna L Persons
(74) *Attorney, Agent, or Firm* — HAMILTON, BROOK, SMITH & REYNOLDS, P.C.

(57) ABSTRACT
This invention relates to the finding that inhibition or inactivation of FAMIN ('fatty acid metabolism—immunity nexus'; C13orf31: LACC1 (laccase domain containing 1)) reduces tumourigenesis and stimulates cell-mediated immune responses. Method of treating cancer orstimulating cell-mediated immune responsesin an individual by reducing FAMIN activity in the individual are provided. Also provided are methodsofactivating T cells in vitro using FAMIN deficient immune cells and stimulating cell-mediated immune responses comprising administering(a) a population of FAMIN deficient immune cells; or(b) a population of T cells activated in vitro by a population of FAMIN deficient immune cells.

8 Claims, 23 Drawing Sheets

Specification includes a Sequence Listing.

(56) References Cited

OTHER PUBLICATIONS

Samudio et al., 2010, "Pharmacologic inhibition of fatty acid oxidation sensitizes human leukemia cells to apoptosis induction", J Clin Invest. 120(1): 142-156 (Year: 2010).*

Skon-Hegg et al., Dec. 3, 2018, "LACC1 Regulates TNF and IL-17 in Mouse Models of Arthritis and Inflammation", The Journal of Immunology, 1;202(1): 181-193 (Year: 2018).*

De Souza, et al., 2006, "Transcriptional and phenotypic comparisons of Ppara knockout and siRNA knockdown mice", Nucleic Acids Research, vol. 34, No. 16, p. 4486-4494 (Year: 2006).*

Saveljeva et al., 2022, Cell Metabolism, 34, p. 106-124 (Year: 2022).*

Laccase domain-containing protein 1 isoform 1, NCBI Reference Sequence: NP_001121775.1, available Sep. 10, 2017 (Year: 2017).*

*Homo sapiens* laccase domain containing 1 (LACC1), transcript variant 1, mRNA, NCBI Reference Sequence: NM_001128303.2, available Jul. 17, 2017 (Year: 2017).*

International Search Report and Written Opinion for PCT/EP2019/084256, entitled "FAMIN Assay Methods", issued on Feb. 28, 2020.

Cader, M. Z. et al., C13orf31 (FAMIN) is a central regulator of immunometabolic function, Nature Immunology, vol. 17, No. 9, Aug. 1, 2016 (Aug. 1, 2016), pp. 1046-1056.

Cader, M. Zaeem et al., FAMIN Is a Multifunctional Purine Enzyme Enabling the Purine Nucleotide Cycle, Cell, Elsevier, Amsterdam, Nl, vol. 180, No. 2, Jan. 23, 2020 (Jan. 23, 2020), p. 278.

Moriwaki, Y. et al., Enzymes involved in purine metabolism—A review of histochemical localization and functional Implications, Histology and Histopathology: Cellular and Molecular Biology, Gutenberg, ES, vol. 14, No. 4, Oct. 1, 1999 (Oct. 1, 1999), pp. 1321-1340.

Wakil, Salma M. et al., Association of a Mutation in LACCI With a Monogenic Form of Systemic Juvenile Idiopathic Arthritis: Monogenic Systemic Juvenile Idiopathic Arthritis, ARTHRITIS & Rheumatology (Hoboken), vol. 67, No. 1, Dec. 27, 2014 (Dec. 27, 2014), pp. 288-295.

International Search Report and Written Opinion for PCT/EP2019/084265, entitled "Methods of Cancer Treatment", issued on Apr. 9, 2020.

Cader, M. Zaeem et al., C13orf31 (FAMIN) is a central regulator of immunometabolic function, Nature Immunology, vol. 17, No. 9, Sep. 1, 2016 (Aug. 1, 2016), pp. 1046-1056.

Albers "Metabolic Characteristics and Importance of the Universal Methionine Salvage Pathway Recycling Methionine from 5'-Methylthioadenosine" IUBMB Life. Dec. 2009;61(12):1132-42.

Ashihara, et al. "Purine salvage in plants" Phytochemistry 147, 89-124 (2018).

Assadi, et al. "Functional Analyses of the Crohn's Disease Risk Gene LACC1" PLOS ONE 11(12): e0168276 (2016).

Beloqui, et al. "Novel Polyphenol Oxidase Mined from a Metagenome Expression Library of Bovine Rumen: Biochemical Properties, Structural Analysis, and Phylogenetic Relationships" Journal of Biological Chemistry, vol. 281, No. 32, 2006, 22933-22942.

Boison "Adenosine Kinase: Exploitation for Therapeutic Gain" Pharmacol Rev. Jul. 2013;65(3):906-43.

Bradford, et al. "Adenosine Deaminase (ADA)-Deficient Severe Combined Immune Deficiency (SCIO): Molecular Pathogenesis and Clinical Manifestations" J. Clin. Immunol. 37, 626-637 (2017).

Bzowska, et al. "Purine nucleoside phosphorylases: properties, functions, and clinical aspects" Pharmacol. Ther. 88, 349-425 (2000).

Camici, et al. "Interplay between adenylate metabolizing enzymes and AMP-activated protein kinase." The FEBS Journal 285 (2018): 3337-3352.

Camici, et al. "The Inside Story of Adenosine" Int. J. Mol. Sci. 2018; 19(3):784.

Canas, et al. "Laccases and their natural mediators: Biotechnological tools for sustainable eco-friendly processes" Biotechnol. Adv. 28, 694-705 (2010).

Chen, et al. "Gene Deletion Chemoselectivity: Codeletion of the Genes for p16INK4, Methylthioadenosine Phosphorylase, and the a- and -Interferons in Human Pancreatic Cell Carcinoma Lines and Its Implications for Chemotherapy" Cancer Res. 56, 1083-1090 (1996).

Della Ragione, et al. "Purification and Characterization of Recombinant Human 5-Methylthioadenosine Phosphorylase: Definite Identification of Coding cDNA" Biochem. Biophys. Res. Commun. 223, 514-519 (1996).

Folch, et al. "A simple method for the isolation and purification of total lipides from animal tissues" J Biol Chem. May 1957;226(1):497-509. PMID: 13428781.

Friedkin, et al., "Nucleoside Phosphorylases," The Enzymes, p. D. Boyer, H. Lardy, K. Myrback, Eds. (Academic Press, New York, 1961), vol. 5, pp. 237-255.

Giblett, et al. "Adenosine-Deaminase Deficiency in Two Patients With Severely Impaired Cellular Immunity" Lancet 2, 1067-1069 (1972).

Giblett, et al. "Nucleoside-Phosphorylase Deficiency in a Child With Severely Defective T- Cell Immunity and Normal B-Cell Immunity" Lancet 1, 1010-1013 (1975).

Gizzi, et al. "A naturally occurring antiviral ribonucleotide encoded by the human genome" Nature. Jun. 2018;558 (7711):610-614.

Gorshkov, et al. "Polyphenol oxidase from Pectobacterium atrosepticum: identification and cloning of gene and characteristics of the enzyme." Journal of basic microbiology 57.12 (2017): 998-1009.

Holm, et al. "An Evolutionary Treasure: Unification of a Broad Set of Amidohydrolases Related to Urease" Proteins: Structures, Function, and Genetics, 28, 72-82 (1997).

Jabri, et al. "The Crystal Structure of Urease from Klebsiella aerogenes" Science 268, 998-1004 (1995).

Kim, et al. "Crystal Structure of Hypothetical Protein YfiH From Shigella flexneri at 2 A Resolution" Proteins 63, 1097-1101 (2006).

Kryukov, et al. "MTAP deletion confers enhanced dependency on the arginine methyltransferase PRMT5 in human cancer cells" Science. Mar. 11, 2016;351(6278):1214-8.

Landgraf, et al. "Radical S-Adenosylmethionine Enzymes in Human Health and Disease" Annu. Rev. Biochem. 2016. 85:485-514.

Lindley, et al. "Demonstration of adenosine deaminase activity in human fibroblast lysosomes" Biochem J. Mar. 1, 1993;290 (Pt 2):457-62.

Mavrakis, et al. "Disordered methionine metabolism in MTAP/CDKN2A-deleted cancers leads to dependence on PRMT5" Science 351, 1208-1213 (2016).

Maynes, et al. "Design of an adenosine phosphorylase by active-site modification of murine purine nucleoside phosphorylase" Biochem. J. 344 Pt 2, 585-592 (1999).

Murray "The Biological Significance of Purine Salvage" Annu. Rev. Biochem. 40,811 (1971).

Nobori, et al. "Genomic Cloning of Methylthioadenosine Phosphorylase: A Purine Metabolic Enzyme Deficient in Multiple Different Cancers" Proc. Natl. Acad. Sci. U.S.A. 93, 6203 (1996).

Non-Final Office Action received for U.S. Appl. No. 17/312,350, mailed on Apr. 4, 2024, 7 pages.

O'Neill, et al. "Immunometabolism governs dendritic cell and macrophage function" J. Exp. Med. 2016 vol. 213 No. 1 15-23.

Perna, et al. "Multiple Reaction Monitoring for quantitative laccase kinetics by LC-MS" Sci Rep 8, 8114 (2018).

Prosser, et al. "Metabolomic strategies for the identification of new enzyme functions and metabolic pathways" EMBO Reports (2014) 15, 657-669.

Wilson, et al. "Atomic Structure of Adenosine Deaminase Complexed with a Transition-State Analog: Understanding Catalysis and Immunodeficiency Mutations" Science 252, 1278-1284 (1991).

Zhao, et al. "Discovery of new enzymes and metabolic pathways using structure and genome context" Nature. Oct. 31, 2013;502(7473):698-702. doi: 10.1038/nature12576. Epub Sep. 22, 2013. PMID: 24056934; PMCID: PMC3966649.

Zimmerman, et al. "Adenine as Substrate for Purine Nucleoside Phosphorylase" Can. J. Biochem. 49, 1050-1054 (1971).

Notice of Allowance received for U.S. Appl. No. 17/312,350, mailed on Feb. 21, 2025, 5 pages.

Notice of Allowance received for U.S. Appl. No. 17/312,350, mailed on Oct. 22, 2024, 8 pages.

(56)          References Cited

OTHER PUBLICATIONS

Xiao et al., "EENdb: a database and knowledge base of ZFNs and TALENs for endonuclease engineering", Nucleic Acids Research, vol. 41, Nov. 29, 2012, pp. D415-D422.

Yang et al., "One-step generation of mice carrying reporter and conditional alleles by CRISPR/Cas mediated genome engineering", Cell. Author manuscript, vol. 154, No. 6, Sep. 12, 2013, pp. 1-18.

Altschul et al., "Basic Local Alignment Search Tool", J. Mol. Biol., vol. 215, 1990, pp. 403-410.

Altschul et al., "Gapped blast and PSI-BLAST: a new generation of protein database search programs", Nucleic Acids Research, vol. 25, No. 17, 1997, pp. 3389-3402.

Angell et al., "Consistent gene silencing in transgenic plants expressing a replicating potato virus X RNA", The Embo Journal, vol. 16, No. 12, 1997, pp. 3675-3684.

Autissier et al., "Evaluation of a 12-Color Flow Cytometry Panel to Study Lymphocyte, Monocyte, and Dendritic Cell Subsets in Humans", Cytometry Part A, Jan. 22, 2010, pp. 410-419.

Banchereau et al., "Dendritic cells and the control of immunity", Nature, vol. 392, Mar. 19, 1998, pp. 245-252.

Beerli RR, Barbas CF 3rd., Engineering polydactyl zinc-finger transcription factors, Nat Biotechnol. Feb. 2002, 135-41, 20(2).

Cader et al., "C13orf31 (FAMIN) is a central regulator of immunometabolic function", Nat Immunol, vol. 17, No. 9, Sep. 1, 2016, pp. 1-35.

Chauhan et al., "A comprehensive review on bioactive fused heterocycles as purine-utilizing enzymes inhibitors", Med Chem Res, Nov. 16, 2014, pp. 2259-2282.

Cong et al., "Multiplex Genome Engineering Using CRISPR/Cas Systems", Science, vol. 339, No. 6121, Feb. 15, 2013, pp. 1-9.

Elbashir et al., "RNA interference is mediated by 21-and 22-nucleotide RNAs", Genes & Development, Dec. 1, 2006, pp. 188-200.

Elbashir SM et al., Duplexes of 21-nucleotide RNAs mediate RNA interference in cultured mammalian cells, May 24, 2001, Nature, 494-498, 411.

Fire et al., "Potent and specific genetic interference by double-strandedRNAin Caenorhabditis elegans", Nature, vol. 391, Feb. 19, 1998, pp. 806-811.

Firestone et al., "Heat Capacity Changes for Transition-State Analogue Binding and Catalysis with Human 5'-Methylthioadenosine Phosphorylase", ACS Chemical Biology, Dec. 6, 2016, pp. 464-473.

Gaj e al., "ZFN, TALEN and CRISPR/Cas-based methods for genome engineering", Trends Biotechnol., vol. 31, No. 7, Jul. 2013, pp. 1-20.

Gaudernack et al., Isolation of pure functionally active CD8+ T cells. Positive selection with monoclonal antibodies directly conjugated to monosized magnetic microspheres, 1986 J Immunol Methods, 179-87, 90(2).

Gilbert et al., "CRISPR-Mediated Modular RNA-Guided Regulation of Transcription in Eukaryotes", Cell, vol. 154, No. 2, Jul. 18, 2013, pp. 1-20.

Grivennikov et al., "Immunity, Inflammation, and Cancer", Cell, vol. 140, No. 6, Mar. 19, 2010, pp. 1-31.

Gupta et al., "An optimized two-finger archive for ZFN-mediated gene targeting", Nat Methods., vol. 9, No. 6, Jun. 9, 2012, pp. 1-16.

Ho et al., In vitro methods for generating CD8+ T-cell clones for immunotherapy from the naïve repertoire, Journal of Immunological Methods (2006), 40-52, 310.

Horvath et al., "CRISPR/Cas, the Immune System of Bacteria and Archaea", Science, vol. 327, Jan. 8, 2010, pp. 167-170.

Hwang et al., "Efficient In Vivo Genome Editing Using RNA-Guided Nucleases", Nat Biotechnol., vol. 31, No. 3, Mar. 31, 2013, pp. 1-12.

Jinek et al., "A programmable dual RNA-guided DNA endonuclease in adaptive bacterial immunity", Science. Author Manuscript, vol. 337, No. 6096, Aug. 17, 2012, pp. 1-14.

Jinek et al., "RNA-programmed genome editing in human cells", ELife, Jan. 29, 2013, pp. 1-9.

Johnson et al., "Hidden Markov model speed heuristic and iterative HMM search procedure", BMC Bioinformatics, 2010, pp. 1-8.

Jostins et al., "Host-microbe interactions have shaped the genetic architecture of inflammatory bowel disease", Nature, vol. 491, No. 7422, Nov. 1, 2012, pp. 1-18.

Joung et al., "TALENs: a widely applicable technology for targeted genome editing", Nat Rev Mol Cell Biol., Jan. 14, 2013, pp. 1-16.

Kim et al., A library of TAL effector nucleases spanning the human genome, Nat Biotechnol. Mar. 2013, 251-258, 31 (3).

Kinzler et al., "Lessons from Hereditary Colorectal Cancer", Cell, vol. 87, Oct. 18, 1996, pp. 159-170.

Liu et al. "Discovery of six new susceptibility loci and analysis of pleiotropic effects in leprosy", Nature Genetics, vol. 47, No. 3, Mar. 2015, 8 pages.

Lum et al., In Vitro Regulation of Immunoglobulin Synthesis by T-Cell Subpopulations Defined by a New Human T-Cell Antigen (9.3), (1982) Cell Immunol, 122-129, 72.

Maeder et al., "Rapid "open-source" engineering of customized zinc-finger nucleases for highly efficient gene modification", Cell, vol. 31, No. 2, Jul. 25, 2008, pp. 1-13.

Mali et al., "RNA-Guided Human Genome Engineering via Cas9", Science, vol. 339, No. 6121, Feb. 15, 2013, pp. 1-8.

Mantovani, Molecular Pathways Linking Inflammation and Cancer, Curr. Mol. Med. 2010, 369-373, 10.

Miller et al., "A Tale nuclease architecture for efficient genome editing", Nature Biotechnology, vol. 29, No. 2, Feb. 2011, 8 pages.

Moser et al., "A Dominant Mutation That Predisposes to Multiple Intestinal Neoplasia in the Mouse", Science, vol. 247, Jan. 19, 1990, pp. 321-324.

Patel, N et al., Study of Mendelian forms of Crohn's disease in Saudi Arabia reveals novel risk loci and alleles, Gut, Nov. 2014, 1831-1832, 63(11).

Pearson et al., "An Introduction to Sequence Similarity ("Homology") Searching", Curr Protoc Bioinformatics, Jun. 2013, pp. 1-9.

Pearson et al., "Improved tools for biological sequence comparison", Proc. Natl. Acad. Sci., vol. 85, 1988, pp. 2444-2448.

Qi et al., "Repurposing CRISPR as an RNA-Guided Platform for Sequence-Specific Control of Gene Expression", Cell., vol. 152, No. 5, Feb. 28, 2013, pp. 1-22.

Qu et al., "Zinc-finger-nucleases mediate specific and efficient excision of HIV-1 proviral DNA from infected and latently infected human T cells", Nucleic Acids Research, vol. 41, No. 16, Jun. 26, 2013, pp. 7771-7782.

Reinherz et al., "Separation of functional subsets of human T cells by a monoclonal antibody", Proc. Natl. Acad. Sci., vol. 76, No. 8, Aug. 1979, pp. 4061-4065.

Reyon et al., "Flash Assembly of TALENs Enables High-Throughput Genome Editing", Nat Biotechnol., vol. 30, No. 5, 2012, pp. 1-23.

Rosenberg et al., Use of tumor-infiltrating lymphocytes and interleukin-2 in the immunotherapy of patients with metastatic melanoma. A preliminary report, Dec. 22, 1988, New Eng. J. of Med., 1676-80, 319.

Silva et al., "Meganucleases and Other Tools for Targeted Genome Engineering: Perspectives and Challenges for Gene Therapy", Current Gene Therapy, vol. 11, No. 1, 2011, pp. 11-27.

Smith et al., "Identification of Common Molecular Subsequences", J. Mol. Biol., 1981, 4 pages.

Stanley T. Crooke, Therapeutic applications of oligonucleotides, Annu. Rev. Pharmacol. Toxicol. 1992, 329-376, 32.

Uhlmann, E.; Peyman, A., Antisense oligonucleotides: a new therapeutic principle, Chem. Rev. Jun. 1990, 543-584, 90(4).

Voinnet & Baulcombe, Systemic signalling in gene silencing, Oct. 9, 1997, Nature, 553, 389.

Wang et al., "One-Step Generation of Mice Carrying Mutations in Multiple Genes by CRISPR/Cas-Mediated Genome Engineering", Cell. Author Manuscript, vol. 153, No. 4, May 9, 2013, pp. 1-17.

Wynn et al., "Origins and Hallmarks of Macrophages: Development, Homeostasis, and Disease", Nature. Author manuscript, vol. 496, No. 7446, Apr. 25, 2013, pp. 1-24.

Latchman, Y.E. et al., "PD-L1-deficient mice show that PD-L1 on T cells, antigen-presenting cells, and host tissues 1 negatively regulates T cells," PNAS, 101(29): 10691-10696 (Jul. 20, 2004).

Basu, et al., A pico-molar 5'-methylthioadenosine phosphorylase transition state analog inhibits human lung cancer growth and

(56) References Cited

OTHER PUBLICATIONS metastases in mouse xenografts, Apr. 1, 2009, Proceedings of the Annual Meeting of the American Association for Cancer Research American Association for Cancer Research, US, 436, 50.

Basu, et al., A Transition State Analogue of 5'-Methylthioadenosine Phosphorylase Induces Apoptosis in Head and Neck Cancers*, Jul. 20, 2007, Journal of Biological Chemistry American Society for Biochemistry and Molecular Biology, US, 21477-21485, 282:29.

Basu, et al., Growth and Metastases of Human Lung Cancer Are Inhibited in Mouse Xenografts by a Transition State Analogue of 5'-Methylthioadenosine Phosphorylase, Feb. 11, 2011, Journal of Biological Chemistry, 4902-4911, 286:6.

De Fouw, et al., Differential cytotoxicity of deoxyguanosine and 8-aminoguanosine for human leukemic cell lines and normal bone marrow progenitor cells, Apr. 1, 1984, Hematological Oncology, 189-197, 2:2.

Polanski, et al., Transition state analogue inhibitors of Methylthioadenosine Phosphorylase (MTAP), polyamine biosynthesis, and prostate cancer, May 1, 2005, Cancer Research American Association for Cancer Research.

Sato, et al., Effect of combinations of deoxyguanosine and 8-aminoguanosine with 2,3-dihydro-1H-imidazo[1,2-b] pyrazole on L1210 cell crowth in culture, Feb. 15, 1984, Biochemical Pharmacology Elsevier, US,, 689-691, 33:4.

* cited by examiner

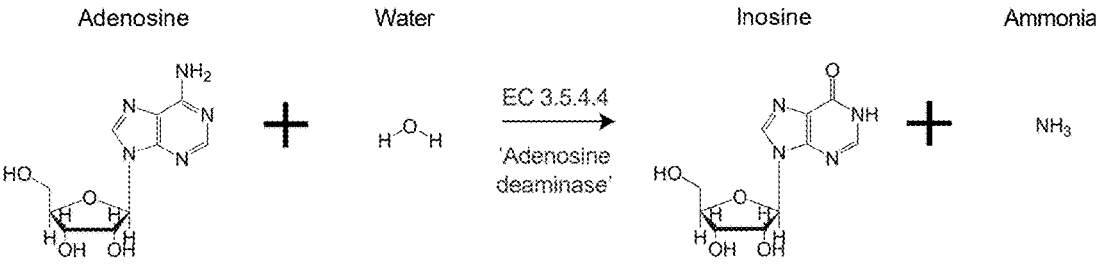
FIG. 10B
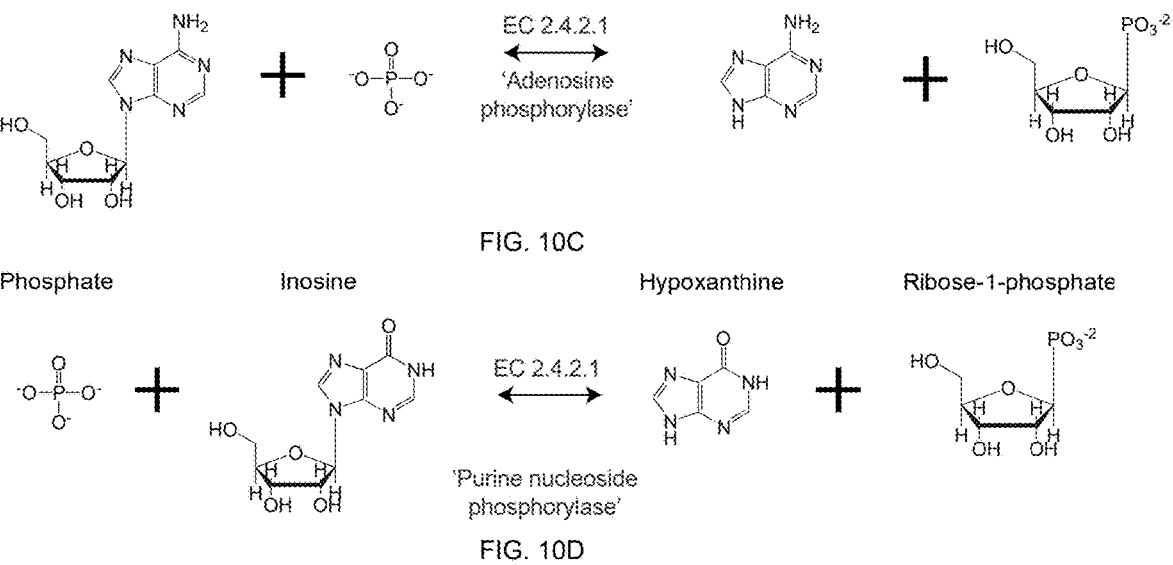
FIG. 10C
FIG. 10D
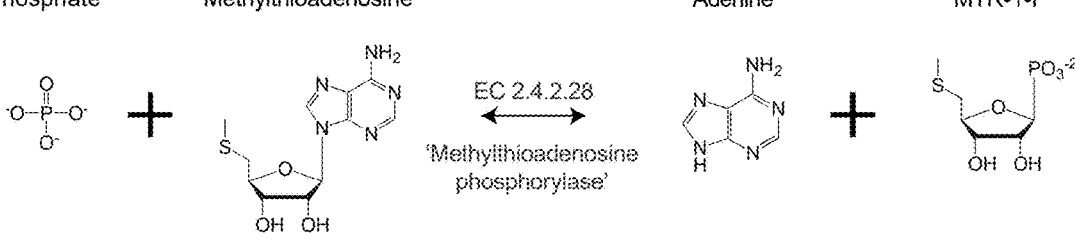
FIG. 10E

Adenosine → R-1-P

Inosine → Hypoxanthine

METHODS OF TREATING CANCER BY SUPPRESSION OF FAMIN EXPRESSION

RELATED APPLICATIONS

This application is the U.S. National Stage of International Application No. PCT/EP2019/084265, filed Dec. 9, 2019, which designates the U.S., published in English, and claims priority under 35 U.S.C. § 119 or 365 (c) to GB Application No. 1820098.0, filed Dec. 10, 2018. The entire teachings of the above applications are incorporated herein by reference.

INCORPORATION BY REFERENCE OF MATERIAL IN ASCII TEXT FILE

This application incorporates by reference the Sequence Listing contained in the following ASCII text file:
    a)    File    name:    42854473_5559.1004-002_Sub._Seq._Listing2.txt; created May 9, 2024, 10,388 bytes in size.

FIELD

This invention relates to the targeting of the protein 'FAMIN' ('fatty acid metabolism-immunity nexus'), for example for the treatment of cancer and stimulating cell-mediated immune responses.

BACKGROUND

Single-nucleotide variations in LACC1 (C13orf31) that encode p.C284R and p.I254V in a protein of unreported function (called 'FAMIN' here) are associated with increased risk for systemic juvenile idiopathic arthritis, leprosy and Crohn's disease[6-9].

FAMIN has been shown to form a complex with fatty acid synthase (FASN) on peroxisomes and promote flux through de novo lipogenesis to concomitantly drive high levels of fatty-acid oxidation (FAO) and glycolysis and, consequently, ATP regeneration. FAMIN-dependent FAO has been shown to control inflammasome activation, mitochondrial and NADPH-oxidase-dependent production of reactive oxygen species (ROS), and the bactericidal activity of macrophages[1].

SUMMARY

The present inventors have unexpectedly found that inhibition or inactivation of FAMIN ('fatty acid metabolism-immunity nexus'; C13orf31; LACC1 (laccase domain containing 1)) reduces tumourigenesis and may therefore be useful in the treatment of cancer. In addition, the present inventors have also found that FAMIN inhibition or inactivation stimulates cell-mediated immune responses and may therefore be useful, for example in promoting tumour immune surveillance and/or treating infection.

A first aspect of the invention provides a method of treating cancer in an individual in need thereof comprising reducing FAMIN activity in the individual.

Related aspects of the invention provide a FAMIN inhibitor or antagonist for use in the treatment of cancer in an individual and the use of a FAMIN inhibitor or antagonist in the manufacture of a medicament for use in the treatment of cancer in an individual.

A second aspect of the invention provides a method of stimulating a cell-mediated immune response in an individual in need thereof comprising reducing FAMIN activity in the individual.

Related aspects of the invention provide a FAMIN inhibitor or antagonist for use in stimulating a cell-mediated immune response in an individual in need thereof and the use of a FAMIN inhibitor or antagonist in the manufacture of a medicament for use stimulating a cell-mediated immune response in an individual in need thereof.

FAMIN activity may be reduced by administering a FAMIN inhibitor or antagonist to the individual or by administering to the individual a FAMIN suppressor nucleic acid or targeted nuclease or a vector encoding a FAMIN suppressor nucleic acid or targeted nuclease that reduces expression of FAMIN.

FAMIN activity may be reduced systemically in the individual or may be reduced selectively or specifically in a particular cell type, such as tumour cells, endothelial cells, stromal cells or immune cells.

A third aspect of the invention provides a method of stimulating a cell-mediated immune response in an individual in need thereof comprising;
    administering a population of immune cells having reduced FAMIN activity to the individual.

In some embodiments, the individual may have cancer and the method may be a method of cancer immunotherapy. In other embodiments, the individual may have an infection and the method may be a method of immunotherapy.

Suitable immune cells include neutrophils, macrophages and dendritic cells.

The immune cells may have reduced FAMIN activity relative to control immune cells or may be devoid of FAMIN activity.

In some embodiments, the population of immune cells having reduced FAMIN activity may be produced by a method comprising;
    providing an initial population of immune cells, for example obtained from a donor individual,
    reducing the activity of FAMIN in the immune cells to produce a population of FAMIN deficient immune cells, and
    culturing the immune cells having reduced FAMIN activity.

In other embodiments, the population of immune cells having reduced FAMIN activity may be produced by a method comprising;
    providing an initial population of immune progenitor cells, for example obtained from a donor individual,
    reducing the activity of FAMIN in the immune progenitor cells to produce a population of FAMIN deficient immune progenitor cells, and
    differentiating the FAMIN deficient immune progenitor cells to produce a population of immune cells having reduced FAMIN activity.

A fourth aspect of the invention provides an in vitro method of activating antigen-specific T cells comprising;
    providing a population of T cells,
    culturing the T cells with a population of immune cells having reduced FAMIN activity,
    thereby producing an activated T cell population specific for the displayed target antigen.

The T cells may be naïve T cells or antigen specific T cells.

The activated T cell population may have increased cytolytic activity relative to T cells activated with control immune cells displaying the antigen.

A fifth aspect of the invention provides a method of stimulating a cell-mediated immune response in an individual in need thereof comprising administering to an individual in need thereof a population of T cells activated in vitro by immune cells having reduced FAMIN activity.

Preferably, the individual has cancer and the method is a method of cancer immunotherapy. The T cells may be specific for an antigen expressed by cancer cells in the individual.

A sixth aspect of the invention provides a population of T cells activated in vitro by immune cells having reduced FAMIN activity.

Suitable immune cells for use in the activation of T cells include dendritic cells.

The activity of FAMIN in the immune cells or immune progenitor cells of the second to sixth aspects may be reduced by inactivation or suppression of FAMIN expression in the cells or inhibition of FAMIN activity in the cells, for example using a small molecule inhibitor.

Other aspects and embodiments of the invention are described in more detail below.

BRIEF DESCRIPTION OF FIGURES

FIG. 1 shows the results of culturing splenic Famin$^{+/+}$ or Famin$^{-/-}$ CD11c$^+$ DCs pulsed with the I-Ad-restricted OVA MHC class II epitope OVA$^{323-339}$ with CFSE labelled naïve CD4$^+$ OT-II; Rag2$^{-/-}$ T cells, which carry a T cell receptor specific for OVA$^{323-339}$.

FIG. 2 shows the results of intravenously injecting 7.5× 10$^6$ CFSE-labelled naïve CD4$^+$ OT-II; Rag2$^{-/-}$ T cells into Famin$^{\Delta DC}$ and Famin$^{WT}$ mice that were thereafter intraperitoneally immunised with 25 µg OVA.

FIG. 3 shows the results of pulsing splenic CD11c$^+$ DCs isolated from Famin$^{\Delta DC}$ and Famin$^{WT}$ mice with the H-2Kb-restricted OVA MHC class I epitope OVA$^{257-264}$, which were then co-cultured in vitro with naïve T cells from OT-I; Rag$^{-/-}$ mice for 72 h, followed by passaging for a further 6 days. CD8$^+$ OT-I T cells are transgenic for a T cell receptor recognising OVA$^{257-264}$.

FIG. 4 shows the effect of FAMIN on the differentiation of naïve CD8$^+$ T cells into antigen-specific CTLs in vivo. Naïve CD8$^+$ OT-I; Rag$^{-/-}$ T cells were intravenously injected into Famin$^{\Delta DC}$ and Famin$^{WT}$ mice that were thereafter intraperitoneally immunised with 25 µg OVA.

FIG. 5 shows the effect of FAMIN on tumour immune surveillance.

FIG. 10 shows that FAMIN is a purine nucleoside metabolising enzyme. FIGS. 10B, C, D, and E depict the enzymatic activities of FAMIN that were unambiguously identified by incubating pure substrate with recombinant FAMIN and measuring its products. Methylthioadenosine refers to S-methyl-5'-thioadenosine and MTR-1-P to S-methyl-5'-thioribose-1-phosphate.

FIG. 11 shows modulation of FAMIN enzymatic function with small molecules.

DETAILED DESCRIPTION

Figure 1A:
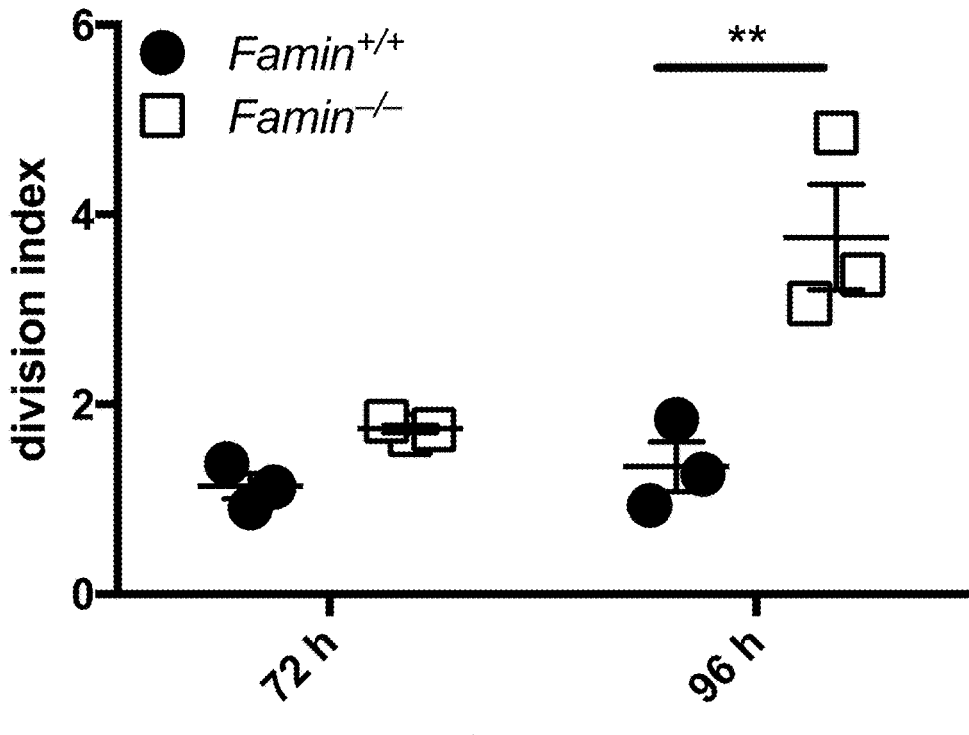
FIG. 1A shows the proliferative response of OT-II T cells expressed as division index (average number of cell divisions that a cell in the original population has undergone) derived from such co-cultures with Famin$^{-/-}$ and Famin$^{+/+}$ DCs.

This invention relates to the unexpected finding that FAMIN ('fatty acid metabolism-immunity nexus'; C13orf31; LACC1 (laccase domain containing 1)) is a trifunctional purine salvage enzyme that displays a combination of adenosine deaminase, purine nucleoside phosphorylase and methylthioadenosine phosphorylase activities. In addition, the present inventors have surprisingly found that reducing the activity of FAMIN in one or more cells of a mammal reduces tumourigenesis and stimulates cell-mediated immune responses. In some embodiments, these findings provide treatments for cancer or infection comprising reducing FAMIN activity in one or more cells of an individual in vivo. In other embodiments, this finding provides for methods of stimulation of cell-mediated immune responses by administering immune cells with reduced FAMIN activity or T cells activated in vitro by immune cells with reduced FAMIN activity.

In preferred embodiments, a FAMIN polypeptide is human FAMIN. However, in some embodiments, for example when the individual to be treated is a non-human mammal, a non-human mammalian FAMIN may be employed.

The human gene (Gene ID NO: 144811) encoding the FAMIN polypeptide has 9 exons and is located at 13q14.11 (NC_000013.11; 43878834 . . . 43893932). A reference human FAMIN amino acid sequence is shown in SEQ ID NO: 1. Other reference human FAMIN amino acid sequences have the database accession numbers NP_001121775.1, NP_001337567.1, NP_001337568.1, NP_001337569.1, NP_001337570.1, NP_001337571.1, NP_001337572.1, NP_001337573.1, NP_001337574.1, NP_001337575.1, NP_001337576.1, NP_001337577.1 and NP_694950.2. A FAMIN polypeptide as described herein may comprise a reference amino acid sequence, such as SEQ ID NO: 1 or an amino acid sequence having at least 80% sequence identity, at least 85% sequence identity, at least 90% sequence identity, at least 95% identity, or at least 98% identity to a reference amino acid sequence, such as SEQ ID NO: 1.

A FAMIN protein as described herein may comprise or consist of a DUF152 domain (Pfam02578, Cluster of Orthologous Group [COG] 1496). The DUF152 domain of a FAMIN protein may be identified using standard sequence analysis techniques. For example, the DUF152 domain is located in the C terminal portion (amino acids 176-430) of human FAMIN. The DUF152 domain may be responsible for the enzymatic activity of the FAMIN protein and the sequence of the DUF152 domain may be conserved between different FAMIN proteins.

A reference human FAMIN coding nucleotide sequence is shown in SEQ ID NO: 2. Other reference human FAMIN coding sequences have the database accession numbers NM_001128303.1, NM_001350638.1, NM_001350639.1, NM_001350640.1, NM_001350641.1, NM_001350642.1, NM_001350643.1, NM_001350644.1, NM_001350645.1, NM_001350646.1, NM_001350647.1, NM_001350648 and NM_153218.2. A FAMIN nucleotide sequence as described herein may comprise a nucleotide sequence of a reference human FAMIN coding sequence, such as SEQ ID NO: 2 or a nucleotide sequence having at least 80% sequence identity, at least 85% sequence identity, at least 90% sequence identity, at least 95% identity, or at least 98% identity to a reference human FAMIN coding sequence, such as SEQ ID NO: 2.

Sequence identity is commonly defined with reference to the algorithm GAP (Wisconsin GCG package, Accelerys Inc, San Diego USA). GAP uses the Needleman and Wunsch algorithm to align two complete sequences that maximizes the number of matches and minimizes the number of gaps. Generally, default parameters are used, with a gap creation penalty=12 and gap extension penalty=4. Use of GAP may be preferred but other algorithms may be used, e.g. BLAST (which uses the method of Altschul et al. (1990) *J. Mol. Biol.* 215:405-410), FASTA (which uses the method of Pearson and Lipman (1988) PNAS USA 85:2444-2448), SSEARCH (Smith and Waterman (1981) *J. Mol Biol.* 147:195-197;), HMMER3 (Johnson L S et al BMC Bioinformatics. 2010 Aug. 18; 11 ( ) 431) or the TBLASTN program, of Altschul et al. (1990) supra, generally employing default parameters (see for example Pearson Curr Prot Bioinformatics (2013) 0 3 doi: 10.1002/0471250953.bi0301s42). In particular, the psi-Blast algorithm may be used (Altschul et al. Nucl. Acids Res. (1997) 25 3389-3402). Sequence identity and similarity may also be determined using Genomequest™ software (Gene-IT, Worcester MA USA). Sequence comparisons are preferably made over the full-length of the relevant sequence described herein.

FAMIN is shown herein to display a combination of adenosine deaminase, purine nucleoside phosphorylase and methylthioadenosine phosphorylase activities. The purine nucleoside activity of FAMIN includes a unique adenosine phosphorylase activity.

The adenosine deaminase activity of FAMIN converts adenosine into inosine or 5'- or 2'-deoxyadenosine into deoxyinosine. The purine nucleoside phosphorylase activity of FAMIN converts purine nucleosides into purine nucleobases and ribose-1-phosphate molecules in the presence of phosphate (e.g. orthophosphate $PO_4^{3-}$). For example, inosine nucleosides may be converted into hypoxanthine and α-D-ribose-1-phosphate (EC2.4.2.1) and guanosine nucleosides may be converted into guanine and α-D-ribose-1-phosphate (EC2.4.2.15) by the FAMIN protein. In addition, the purine nucleoside phosphorylase activity of FAMIN includes an adenosine phosphorylase activity which converts adenosine nucleosides into adenine and α-D-ribose-1-phosphate (EC2.4.2.1 KEGG R01561; adenosine: phosphate α-D-ribosyltransferase; also known as adenosine phosphorylase).

The methylthioadenosine phosphorylase activity converts 5'-methylthioadenosine (S-methyl-5'-thioadenosine) into adenine and S-methyl-5-thio-α-D-ribose-1-phosphate.

FAMIN activity may be determined by measuring any one, two or all three of the adenosine deaminase activity, purine nucleoside phosphorylase activity and methylthioadenosine phosphorylase activity of a FAMIN protein, for example by measuring the depletion of a substrate or the generation of a product in a FAMIN-mediated reaction. The depletion of a substrate or the generation of a product in a FAMIN-mediated adenosine deaminase, purine nucleoside phosphorylase and/or methylthioadenosine phosphorylase reaction may be determined using any convenient analytical technique, such as absorbance, chromatography-coupled mass spectrometry (e.g. LC-MS/MS) or NMR.

In some embodiments, FAMIN activity may be determined in a FAMIN deficient cell relative to a FAMIN proficient cell.

Reduced FAMIN activity is shown herein to reduce tumorigenesis in cancer models. An agent which reduces FAMIN activity may therefore be useful in the treatment of cancer, for example for the inhibition of tumour growth or metastasis. Independently of these tumorigenesis effects, reduced FAMIN activity is also shown herein to increase the activation of cell mediated immune responses. Reduced FAMIN activity is shown herein to reduce tumorigenesis in cancer models. An agent which reduces FAMIN activity may therefore be useful in stimulating immune surveillance/responses, for example in cancer immunotherapy, and cell-based methods of treating infection.

FAMIN activity may be reduced systemically in the individual (i.e. all the cells of the individual may be affected). The restricted expression pattern of FAMIN may be advantageous for systemic approaches.

FAMIN activity may be reduced selectively (i.e. only certain types of cells of the individual may be affected). For example, FAMIN activity may be selectively reduced in cancer cells, stromal cells, endothelial cells or immune cells of the individual. Selective reduction of FAMIN activity may be achieved by the direct administration of an agent which reduces FAMIN activity to target cells, such as a tumour e.g. by injection. Selective reduction of FAMIN activity may be achieved using conventional techniques, such as cell targeted delivery vehicles, such as viral vectors that express a ligand for a specific cell type.

In some embodiments, FAMIN activity may be reduced by administering an agent that inhibits FAMIN activity, such as a FAMIN inhibitor or antagonist. It will be appreciated that an FAMIN antagonist is any such agent capable of antagonising, inhibiting, blocking or down-regulating FAMIN. A FAMIN inhibitor or antagonist may reduce or inhibit one, two, three or all four of the adenosine deaminase activity, adenosine phosphorylase activity, purine nucleoside phosphorylase activity and methylthioadenosine phosphorylase activity of a FAMIN protein.

A suitable FAMIN inhibitor or antagonist may, for example, include small chemical molecules, for example non-polymeric organic compounds having a molecular weight of 900 Daltons or less.

Suitable FAMIN inhibitors or antagonists may include compounds that inhibit similar activities to the adenosine deaminase, purine nucleoside phosphorylase and methylthioadenosine phosphorylase activities of FAMIN, or analogues, derivatives or pro-forms of such compounds. Suitable compounds include ADA inhibitors, such as 3'-deoxy-N-(1-oxododecyl) adenosine, pentostatin (PubchemID 439693, CAS ID 53910-25-1) and EHNA (erythro-9-(2-hydroxy-3-nonyl) adenine (PubchemID 3206, CAS ID 59262-86-1)); PNP inhibitors, such as 8-aminoguanosine (PubchemID 96849; CAS ID 180288-69-1); MTAP inhibitors, such as MT-ImmA and MT-DADMe-ImmA (MTDIA); and purine nucleosides.

The terms "FAMIN antagonist" and "FAMIN inhibitor" as used herein, cover pharmaceutically acceptable salts and solvates of these compounds.

Techniques for the rational design of small molecule inhibitors through structural analysis of target proteins are well-known in the art.

Other aspects of the invention relate to methods of screening to identify FAMIN inhibitors or antagonists that are potentially useful in the treatment of cancer or the stimulation of a cell-mediated immune response. For example, a method of screening for a compound useful in the treatment of cancer or the stimulation of a cell-mediated immune response may comprise;

determining the activity of an isolated FAMIN protein in the presence and absence of a test compound.

A decrease in activity in the presence relative to the absence of the test compound may be indicative that the compound is a FAMIN inhibitor that is potentially useful in the treatment of cancer.

The adenosine deaminase activity, purine nucleoside phosphorylase activity and/or methylthioadenosine phosphorylase activity of the FAMIN protein may be determined in the presence and absence of test compound.

A decrease or reduction in the adenosine deaminase activity, purine nucleoside phosphorylase activity and/or methylthioadenosine phosphorylase activity of the FAMIN protein in the presence relative to the absence of test compound may be indicative that the test compound inhibits the activity of FAMIN protein. For example, the test compound may be a FAMIN inhibitor or antagonist.

For example, a decrease in one or more of (i) the conversion of an adenosine molecule into an inosine molecule, (ii) the conversion of a purine nucleoside into a nucleobase and a ribose-1-phosphate molecule in the presence of the FAMIN protein, (iii) the conversion of a nucleobase and a ribose-1-phosphate molecule into a purine nucleoside (iv) the conversion of adenosine into adenine and a ribose-1-phosphate molecule in the presence of the FAMIN protein, (v) the conversion of adenine and a ribose-1-phosphate molecule into adenosine (vi) the conversion of methylthioadenosine into adenine and a S-methyl-5'-thioribose-1-phosphate molecule, or (vii) the conversion of adenine and a S-methyl-5'-thioribose-1-phosphate molecule into methylthioadenosine; by the FAMIN protein in the presence relative to the absence of the test compound is indicative that the test compound is a FAMIN inhibitor.

The precise format of any of the screening or assay methods of the present invention may be varied by those of skill in the art using routine skill and knowledge. The skilled person is well aware of the need to employ appropriate control experiments. For example, in some embodiments, the amount of the above compounds may also be determined in a control in which FAMIN is inactivated.

A test compound may be an isolated molecule or may be comprised in a sample, mixture or extract, for example, a biological sample. Compounds which may be screened using the methods described herein may be natural or synthetic chemical compounds used in drug screening programmes. Extracts of plants, microbes or other organisms, which contain several characterised or uncharacterised components may also be used.

Suitable test compounds for screening include compounds that inhibit similar activities to the adenosine deaminase, purine nucleoside phosphorylase and methylthioadenosine phosphorylase activities of FAMIN. Suitable test compounds include ADA inhibitors, such as 3'-deoxy-N-(1-oxododecyl) adenosine, pentostatin (PubchemID 439693, CAS ID 53910-25-1) and EHNA (erythro-9-(2-hydroxy-3-nonyl) adenine (PubchemID 3206, CAS ID 59262-86-1) (see for example Chauhan & Kumar, Med Chem Res (2015) 24:2259); PNP inhibitors, such as 8-aminoguanosine (PubchemID 96849; CAS ID 180288-69-1) (see for example Bzowska et al Pharmacol Therap 2000, 88:349); MTAP inhibitors, such as MT-ImmA and MT-DADMe-ImmA (MT-DIA) (Firestone et al, ACS Chem Biol 2017, 12:464); and purine nucleosides.

Suitable test compounds also include analogues, derivatives, variants and mimetics of any of the compounds listed above, for example compounds produced using rational drug design to provide test candidate compounds with particular molecular shape, size and charge characteristics suitable for modulating FAMIN activity.

Combinatorial library technology provides an efficient way of testing a potentially vast number of different compounds for ability to modulate FAMIN activity. Such libraries and their use are known in the art, for all manner of natural products, small molecules and peptides, among others. The use of peptide libraries may be preferred in certain circumstances.

The amount of test compound which may be added to an assay of the invention will normally be determined by trial and error depending upon the type of compound used. Typically, from about 0.001 nM to 1 mM or more concentrations of putative inhibitor compound may be used, for example from 0.01 nM to 100 µM, e.g. 0.1 to 50 µM, such as about 10 µM. Even a compound which has a weak effect may be a useful lead compound for further investigation and development.

A test compound identified as modulating FAMIN activity may be investigated further. For example, the selectivity of a compound for FAMIN may be determined by screening against other isolated ADA, PNP or MTAP enzymes. Suitable methods for determining the effect of a compound on the activity of recombinant enzymes are well known in the art.

A test compound identified as a FAMIN inhibitor or antagonist may be isolated and/or purified or alternatively, it may be synthesised using conventional techniques of recombinant expression or chemical synthesis. Furthermore, it may be manufactured and/or used in preparation, i.e. manufacture or formulation, of a composition such as a medicament, pharmaceutical composition or drug. Methods described herein may thus comprise formulating the test compound in a pharmaceutical composition with a pharmaceutically acceptable excipient, vehicle or carrier for therapeutic application.

Following identification of a FAMIN inhibitor that is potentially useful in the treatment of cancer or the stimulation of a cell-mediated immune response as described herein, a method may further comprise modifying the compound to optimise its pharmaceutical properties. Suitable methods of optimisation, for example by structural modelling, are well known in the art. Further optimisation or modification can then be carried out to arrive at one or more final compounds for in vivo or clinical testing.

Suitable agents for reducing FAMIN activity also include suppressor nucleic acids and targetable nucleases and nucleic acids encoding such agents. The use of nucleic acid suppression and targetable nucleases are well known in the art and described in more detail below.

Nucleic acid encoding a suppressor nucleic acid or targeting nuclease may be contained in a vector. Suitable expression vectors are well-known in the art and include viral vectors, such as retroviral, adenoviral, adeno-associated viral, lentiviral, vaccinia or herpes vectors.

Immune cells with reduced FAMIN activity are shown herein to increase the activation of cell mediated immune responses relative to control immune cells. For example, FAMIN deficient immune cells may increase the activation of T cells in vivo. In particular, FAMIN deficient immune cells are shown herein to increase tumour immune surveillance in cancer models relative to control immune cells and may therefore be useful in cell-based methods of cancer immunotherapy and the treatment of infection.

A FAMIN deficient immune cell is an immune cell in which FAMIN activity is reduced compared to a control immune cell. A FAMIN deficient immune cell may be devoid of FAMIN activity (i.e. FAMIN activity is absent from the immune cell), may show reduced expression of active FAMIN polypeptide, or may show reduced FAMIN activity, for example through inhibition of the FAMIN polypeptide in the cell.

The expression of active FAMIN polypeptide may be reduced in a FAMIN deficient immune cell compared to a control immune cell or may be absent i.e. the transcription of the FAMIN gene and/or translation of FAMIN mRNA may be reduced or absent, such that the immune cell lacks or has a reduced amount of active FAMIN polypeptide. For example, a FAMIN deficient immune cell may express up to 10%, up to 20%, up to 30%, up to 40% or up to 50% of the active FAMIN polypeptide that is expressed by control immune cells.

FAMIN activity may be reduced or abolished in a FAMIN deficient immune cell by recombinant techniques. Suitable techniques are well-known in the art and include nucleic acid suppression techniques and directed mutagenesis techniques, such as gene editing.

The expression of active FAMIN polypeptide may be reduced in a FAMIN deficient immune cell compared to a control immune cell or may be absent i.e. the transcription of the FAMIN gene and/or translation of FAMIN mRNA may be reduced or absent, such that the immune cell lacks or has a reduced amount of active FAMIN polypeptide. For example, a FAMIN deficient immune cell may express up to 10%, up to 20%, up to 30%, up to 40% or up to 50% of the active FAMIN polypeptide that is expressed by control immune cells.

The activity of FAMIN polypeptide may be reduced in a FAMIN deficient immune cell compared to a control immune cell i.e. the immune cell may display normal levels of FAMIN polypeptide but reduced or absent FAMIN activity. For example, a FAMIN deficient immune cell may display up to 10%, up to 20%, up to 30%, up to 40% or up to 50% of the FAMIN activity that is displayed by control immune cells.

FAMIN activity may be reduced or abolished in a FAMIN deficient immune cell by recombinant techniques. Suitable techniques are well-known in the art and include nucleic acid suppression techniques and directed mutagenesis techniques, such as gene editing. FAMIN activity may also be reduced or abolished in a FAMIN deficient immune cell using a FAMIN antagonist or inhibitor. Suitable compounds are described in more detail above.

Suitable immune cells for administration as described herein include leukocytes, in particular neutrophils and antigen presenting leukocytes, such as macrophages and dendritic cells.

Macrophages are phagocytic leukocytes that are involved in development, homeostasis, tissue repair and immunity (Wyn et al (2013) Nature 496 445-455). Macrophages may express MHC II, CD14 and CD33. Suitable methods for identifying and characterizing macrophages are well-known in the art.

Suitable macrophages may be any macrophage type, including tumour-associated macrophages (TAMs) and inflammatory macrophages.

Dendritic cells (DCs) are antigen presenting cells that interact with B and T cells in the lymph nodes to initiate adaptive immune responses. DCs capture and process antigens, express lymphocyte co-stimulatory molecules, migrate to lymphoid organs and secrete cytokines to initiate immune responses (Steinman et al Nature (1998) 19; 392 (6673): 245-52).

Suitable dendritic cells include CD11c$^+$ dendritic cells (DCs). DCs may be MHC$^{high}$ and negative for other lineage markers (e.g. CD3, CD19). Suitable methods for identifying and characterizing DCs are well-known in the art (see for example Autissier et al, Cytometry Part A 2010; DOI: 10.1002/cyto.a.20859).

Suitable immune cells may be obtained from a donor individual. The donor individual may be a mammal, preferably a human or a conventional non-human mammal model (e.g. a murine, primate, porcine, canine, or leporine animal).

Any suitable donor individual may be used. The donor individual may be suffering from cancer or infection, or may be a healthy individual, for example a healthy individual who is human leukocyte antigen (HLA) matched (either before or after donation) with an individual suffering from cancer or infection.

The population of immune cells may be isolated or otherwise obtained from appropriate samples from the donor individual e.g. samples from lymphoid tissue such as spleen or lymph nodes or from blood or tumour samples. Suitable isolation techniques are well known in the art and include, for example fluorescent activated cell sorting (FACS: see for example, Rheinherz et al (1979) PNAS 76 4061), cell panning (see for example, Lum et al (1982) Cell Immunol 72 122) and isolation using antibody coated magnetic beads (see, for example, Gaudernack et al 1986 J Immunol Methods 90 179).

Suitable immune cells may be obtained from a population of immune progenitor cells. The population of immune progenitor cells may be isolated or otherwise obtained from appropriate samples from the donor individual e.g. bone marrow samples. Suitable methods for isolating or generating immune progenitor cells and differentiating them into immune cells are well known in the art.

Immune progenitor cells are cells that are capable of differentiating into immune cells. Immune progenitor cells may include pluripotent cells, such as iPS cells, and multipotent or partially differentiated cells of the haematopoietic lineage, such as haematopoietic stem cells, multipotent progenitor cells, lymphoid progenitor cells, myeloid progenitor cells, lymphoblasts, prolymphocytes, myeloblasts and monoblasts.

Following isolation, the initial population of immune cells or immune progenitor cells may be cultured in vitro such that the cells proliferate in order to expand the initial population. Suitable conditions for the expansion of immune cells or immune progenitor cells are well-known in the art. For example human DCs may be cultured with IL-4 and GM-CSF and macrophages may be cultured with M-CSF according to standard techniques.

In some embodiments, FAMIN activity in the immune cells may be reduced, preferably abolished, to produce the population of FAMIN deficient immune cells. In other embodiments, FAMIN activity in the immune progenitor cells may be reduced, preferably abolished, and the immune progenitor cells further differentiated to produce the population of FAMIN deficient immune cells.

In some embodiments, FAMIN activity is reduced in the immune or immune progenitor cells by inhibiting the activity of FAMIN polypeptide, so that the immune cells or immune progenitor cells lack or have a reduced FAMIN activity. Suitable techniques for inhibiting FAMIN polypeptide, for example using a FAMIN inhibitor or antagonist are described above.

In other embodiments, FAMIN activity is reduced by reducing the expression of active FAMIN polypeptide so that the immune cells or immune progenitor cells lack or have a reduced amount of active FAMIN polypeptide. Suitable techniques for reducing the expression of active FAMIN polypeptide are well-known in the art and include nucleic acid suppression and targeted mutagenesis techniques.

In some embodiments, nucleic acid suppression may be used to reduce the expression of active FAMIN polypeptide in the population of immune cells or immune progenitor cells. The use of nucleic acid suppression techniques such as anti-sense and RNAi suppression, to down-regulate expression of target genes is well-established in the art.

The immune cells or immune progenitor cells may be transfected with a suppressor nucleic acid (i.e. a nucleic acid molecule which suppresses FAMIN expression), such as an siRNA or shRNA, or a heterologous nucleic acid encoding the suppressor nucleic acid. The suppressor nucleic acid reduces the expression of active FAMIN polypeptide by interfering with transcription and/or translation, thereby reducing FAMIN activity in the cells.

RNAi involves the expression or introduction into a cell of an RNA molecule which comprises a sequence which is identical or highly similar to the FAMIN coding sequence. The RNA molecule interacts with mRNA which is transcribed from the FAMIN gene, resulting in the sequence specific degradation or specific post-transcriptional gene silencing (PTGS) of the mRNA. This reduces or suppresses expression of active FAMIN polypeptide (Angell & Baulcombe (1997) The EMBO Journal 16, 12:3675-3684; Voinnet & Baulcombe (1997) Nature 389: pg 553).

The RNA molecule is preferably double stranded RNA (dsRNA) (Fire A. et al Nature 391, (1998)). Synthetic siRNA duplexes have been shown to specifically suppress expression of endogenous and heterologous genes in a wide range of mammalian cell lines (Elbashir SM. et al. Nature, 411, 494-498, (2001)).

Suitable RNA molecules for use in RNAi suppression include short interfering RNA (siRNA). siRNA are double stranded RNA molecules of 15 to 40 nucleotides in length, preferably 15 to 28 nucleotides or 19 to 25 nucleotides in length, for example 19, 20, 21, 22, 23, 24 or 25 nucleotides in length. For example, two unmodified 21 mer oligonucleotides may be annealed together to form a siRNA. A siRNA molecule may contain a 3' and/or 5' overhang on each strand having a length of about 0, 1, 2, 3, 4, or 5 nucleotides. The overhang lengths of the strands are independent, i.e., the length of the overhang on one strand is not dependent on the length of the overhang on the second strand.

Other suitable RNA molecules for use in RNAi include small hairpin RNAs (shRNAs). shRNA are single-chain RNA molecules which comprise or consist of a short (e.g. 19 to 25 nucleotides) antisense nucleotide sequence, followed by a nucleotide loop of 5 to 9 nucleotides, and the complementary sense nucleotide sequence (e.g. 19 to 25 nucleotides). Alternatively, the sense sequence may precede the nucleotide loop structure and the antisense sequence may follow. The nucleotide loop forms a hairpin turn which allows the base pairing of the complementary sense and antisense sequences to form the shRNA.

A suppressor nucleic acid, such as a siRNA or shRNA, may comprise or consist of a sequence which is identical or substantially identical (i.e. at least 90%, at least 95% or at least 98% identical) to all or part (for example, 15 to 40 nucleotides) of a reference FAMIN nucleotide coding sequence, or its complement. Suitable reference sequences coding FAMIN that may be used for the design of suppressor nucleic acids are publically available and include SEQ ID NO: 2. FAMIN activity is suppressed in the immune cells by down-regulation of the production of active FAMIN polypeptide by the suppressor nucleic acid. For example, a siRNA to suppress the expression of human FAMIN may comprise one of the following sequences; UCAGAGAG-GAGUCACAAUA (SEQ ID NO: 3), ACGGAGAGAUCC-CAAGGUA (SEQ ID NO: 4), GAUCUCAACCUCUGUA-CAU (SEQ ID NO: 5), or GACUGUAUACCGAUAGUUU (SEQ ID NO: 6).

Suppressor nucleic acids, such as siRNAs and shRNAs, for reducing FAMIN expression may be readily designed using reference FAMIN coding sequences and software tools which are widely available in the art and may be produced using routine techniques. For example, a suppressor nucleic acid may be chemically synthesized; produced recombinantly in vitro or cells (Elbashir, S. M. et al., Nature 411:494-498 (2001); Elbashir, S. M., et al., Genes & Development 15:188-200 (2001)) or obtained from commercial sources (e.g. Cruachem (Glasgow, UK), Dharmacon Research (Lafayette, Colo., USA)).

In some embodiments, two or more suppressor nucleic acids may be used to suppress the expression of FAMIN. For example a pool of siRNAs may be employed. Suitable siRNA pools are available in the art (for example Dharmacon SMART pool M-015653-00-0010, siGENOME Human LACC1 (144811) siRNA-SMARTpool; Dharmacon reference SO-2397682G). Other siRNAs and SIRNA pools may be produced using standard techniques (see for example reference #1).

Nucleic acid suppression may also be carried out using anti-sense techniques. Anti-sense oligonucleotides may be designed to hybridise to the complementary sequence of nucleic acid, pre-mRNA or mature mRNA, interfering with the production of the base excision repair pathway component so that its expression is reduced or completely or substantially completely prevented. In addition to targeting coding sequence, anti-sense techniques may be used to target control sequences of a gene, e.g. in the 5' flanking sequence, whereby the anti-sense oligonucleotides can interfere with expression control sequences. The construction of anti-sense sequences and their use is well known in the art (Peyman and Ulman, Chemical Reviews, 90:543-584, (1990); Crooke, Ann. Rev. Pharmacol. Toxicol. 32:329-376, (1992)).

Anti-sense oligonucleotides may be generated in vitro or ex vivo for administration or anti-sense RNA may be generated in vivo within the immune cells in which down-regulation of FAMIN is desired. Thus, double-stranded DNA may be placed under the control of a promoter in a "reverse orientation" such that transcription of the anti-sense strand of the DNA yields RNA which is complementary to normal mRNA transcribed from the sense strand of the target gene. The complementary anti-sense RNA sequence is thought then to bind with mRNA to form a duplex, inhibiting translation of the endogenous mRNA from the target gene into protein.

The complete sequence corresponding to the FAMIN coding sequence in reverse orientation need not be used. For example, fragments of sufficient length may be used. It is a routine matter for the person skilled in the art to screen fragments of various sizes and from various parts of the coding or flanking sequences of a gene to optimise the level of anti-sense inhibition. It may be advantageous to include the initiating methionine ATG codon, and perhaps one or more nucleotides upstream of the initiating codon. A suitable fragment may have about 14-23 nucleotides, e.g. about 15, 16 or 17.

In other embodiments, the expression of active FAMIN polypeptide is reduced in the population of immune cells or immune progenitor cells by targeted mutagenesis. The use of targeted mutagenesis techniques such as gene editing, to knock out or abolish expression of target genes is well-established in the art (see for example Gaj et al (2013) Trends Biotechnol. 31 (7) 397-405).

One or more mutations, such as insertions, substitutions or deletions, may be introduced into the FAMIN gene in the immune cells or immune progenitor cells. Suitable mutations include deletions of all or part of the FAMIN gene, for example, one, two or more exons, frameshift mutations, or nonsense mutations introducing premature stop codons. Other suitable mutations may include insertions, deletions or substitutions at or adjacent to residue C284, for example a C284R substitution, or residue 1254, for example an 1254V substitution. The mutations may prevent the expression of active FAMIN polypeptide, for example by impairing transcription or translation of the FAMIN gene or causing an inactive polypeptide to be expressed.

Targeted mutagenesis to introduce one or more mutations may be performed by any convenient method. For example, the immune cells or immune progenitor cells may be transfected with a heterologous nucleic acid which encodes a targetable nuclease. The targetable nuclease may inactivate the FAMIN gene encoding FAMIN in one or more cells of the individual, for example, by introducing one or more mutations that prevent the expression of active FAMIN polypeptide.

The targetable nuclease may be site-specific (e.g. ZFN or TALEN) or may be expressed with one or more targeting sequences that target the nuclease to the FAMIN gene (e.g. CRISPR/Cas).

The heterologous nucleic acid may include an inducible promoter that promotes expression of the targetable nuclease and optional targeting sequence within a specific cell type, for example a tumour cell or an immune cell, such as a macrophage or dendritic cell. For example, the inducible promoter could be a promoter-enhancer cassette that selectively favours expression of the targetable nuclease and the optional targeting sequence within the immune cell or tumour cell over other types of host cells.

Suitable targeting nucleases include, for example, site-specific nucleases, such as zinc-finger nucleases (ZFNs), transcription activator-like effector nucleases (TALENs), and meganucleases or RNA guided nucleases, such as clustered regularly interspaced short palindromic repeat (CRISPR) nucleases.

Zinc-finger nucleases (ZFNs) comprise one or more Cys$_2$-His$_2$ zinc-finger DNA binding domains and a cleavage domain (i.e., nuclease). The DNA binding domain may be engineered to recognize and bind to any nucleic acid sequence using conventional techniques (see for example Qu et al. (2013) Nucl Ac Res 41 (16): 7771-7782). The use of ZFNs to introduce mutations into target genes is well-known in the art (see for example, Beerli et al Nat. Bio-technol.2002; 20:135-141; Maeder et al Mol. Cell. 2008; 31:294-301; Gupta et al Nat. Methods. 2012; 9:588-590) and engineered ZFNs are commercially available (Sigma-Aldrich (St. Louis, MO).

Transcription activator-like effector nucleases (TALENs) comprise a nonspecific DNA-cleaving nuclease fused to a DNA-binding domain comprising a series of modular TALE repeats linked together to recognise a contiguous nucleotide sequence. The use of TALEN targeting nucleases is well known in the art (e.g. Joung & Sander (2013) Nat Rev Mol Cell Bio 14:49-55; Kim et al Nat Biotechnol. (2013); 31:251-258. Miller J C, et al. Nat. Biotechnol. (2011) 29:143-148. Reyon D, et al. Nat. Biotechnol. (2012); 30:460-465).

Meganucleases are endodeoxyribonucleases characterized by a large recognition site (double-stranded DNA sequences of 12 to 40 base pairs); as a result this site generally occurs only once in any given genome (see for example Silva et al. (2011) Curr Gene Ther 11 (1): 11-27).

CRISPR targeting nucleases (e.g. Cas9) complex with a guide RNA (gRNA) to cleave genomic DNA in a sequence-specific manner. The crRNA and tracrRNA of the guide RNA may be used separately or may be combined into a single RNA to enable site-specific mammalian genome cutting within the FAMIN gene or its regulatory elements. The use of CRISPR/Cas9 systems to introduce insertions or deletions into genes as a way of decreasing transcription is well known in the art (see for example Cader et al Nat Immunol 2016 17 (9) 1046-1056, Hwang et al. (2013) Nat. Biotechnol 31:227-229; Xiao et al., (2013) Nucl Acids Res 1-11; Horvath et al., Science (2010) 327:167-170; Jinek M et al. Science (2012) 337:816-821; Cong L et al. Science (2013) 339:819-823; Jinek M et al. (2013) eLife 2: e00471; Mali P et al. (2013) Science 339:823-826; Qi L S et al. (2013) Cell 152:1173-1183; Gilbert L A et al. (2013) Cell 154:442-451; Yang H et al. (2013) Cell 154:1370-1379; and Wang H et al. (2013) Cell 153:910-918).

In some preferred embodiments, the targetable nuclease is a Cas endonuclease, preferably Cas9, which is expressed in the immune cells in combination with a guide RNA targeting sequence that targets the Cas endonuclease to cleave genomic DNA within the FAMIN gene and generate insertions or deletions that prevent expression of active FAMIN polypeptide.

Nucleic acid sequences encoding a suppressor nucleic acid or targetable nuclease and optionally a guide RNA may be comprised within an expression vector. Suitable vectors can be chosen or constructed, containing appropriate regulatory sequences, including promoter sequences, terminator fragments, polyadenylation sequences, enhancer sequences, marker genes and other sequences as appropriate. Preferably, the vector contains appropriate regulatory sequences to drive the expression of the encoding nucleic acid in a host cell. Suitable regulatory sequences to drive the expression of heterologous nucleic acid coding sequences in a range of expression systems are well-known in the art and include constitutive promoters, for example viral promoters such as CMV or SV40. A vector may also comprise sequences, such as origins of replication and selectable markers, which allow for its selection and replication and expression in bacterial hosts, such as *E. coli* and/or in eukaryotic cells, such as yeast, insect or mammalian cells. Vectors suitable for use in expressing a suppressor nucleic acid or targetable nuclease in mammalian cells include plasmids and viral vectors e.g. retroviruses, lentiviruses, adenoviruses, and adeno-associated viruses. Suitable techniques for expressing a suppressor nucleic acid or targetable nuclease in mammalian cells are well known in the art (see for example; *Molecular Cloning: a Laboratory Manual:* 3rd edition, Russell et al., 2001, Cold Spring Harbor Laboratory Press or *Protocols in Molecular Biology*, Second Edition, Ausubel et al. eds. John Wiley & Sons, 1992; *Recombinant Gene Expression Protocols* Ed R S Tuan (March 1997) Humana Press Inc).

Transfection with the vector or nucleic acid may be stable or transient. Suitable techniques for transfecting immune cells are well known in the art. Following transfection, FAMIN deficient immune cells or immune progenitor cells may be identified, selected, isolated and/or purified using standard techniques.

The population of FAMIN deficient immune progenitor cells, for example FAMIN deficient iPS cells produced as described above, may be differentiated into fully differentiated FAMIN deficient immune cells, for example FAMIN deficient dendritic cells or macrophages. Suitable techniques for the differentiation of immune cells are well-known in the art.

The FAMIN deficient immune cells may be cultured and/or expanded. Any suitable system may be employed, including stirred tank fermenters, airlift fermenters, roller bottles, culture bags or dishes, and other bioreactors, in particular hollow fibre bioreactors. The use of such systems is well-known in the art.

Numerous culture media suitable for use in the proliferation of immune cells in vitro or ex vivo are available, in particular complete media, such as AIM-V, Iscoves medium and RPMI-1640 (Invitrogen-GIBCO). The medium may be supplemented with other factors such as serum, serum proteins and selective agents. For example, in some embodiments, RPMI-1640 medium containing 2 mM glutamine, 10% FBS, 25 mM HEPES, pH 7.2, 1% penicillin-strepto-mycin, and 55 µM B-mercaptoethanol. Media for DC culture may be supplemented with IL-4 and GM-CSF and media for macrophage culture may be supplemented with M-CSF.

Conveniently, cells are cultured at 37° C. in a humidified atmosphere containing 5% $CO_2$ in a suitable culture medium.

Methods and techniques for the culture of immune cells and other mammalian cells are well-known in the art (see, for example, Basic Cell Culture Protocols, C. Helgason, Humana Press Inc. U.S. (15 Oct. 2004) ISBN: 1588295451; Human Cell Culture Protocols (Methods in Molecular Medicine S.) Humana Press Inc., U.S. (9 Dec. 2004) ISBN: 1588292223; Culture of Animal Cells: A Manual of Basic Technique, R. Freshney, John Wiley & Sons Inc (2 Aug. 2005) ISBN: 0471453293, Ho W Y et al J Immunol Methods. (2006) 310:40-52)

FAMIN deficient immune cells as described may be investigated further, for example the immunological properties and/or activity may be determined. Methods and means of cell analysis are well-known in the art.

Following expansion, the population of FAMIN deficient immune cells produced as described herein may be stored, for example by lyophilisation and/or cryopreservation, as appropriate before use.

A population of FAMIN deficient immune cells as described herein may be useful in therapy, for example to stimulate cell-mediated immune responses. In some embodiments, FAMIN deficient immune cells may be administered to an individual for the treatment of cancer. In some embodiments, FAMIN deficient immune cells administered to an individual may display a disease antigen, such has a tumour antigen or tumour associated antigen. Suitable methods of displaying a disease antigen on the surface of an immune cell are well known in the art.

In other embodiments, the FAMIN deficient immune cells may be used as an adjuvant in adoptive T cell therapy (ACT). For example, the FAMIN deficient immune cells may be administered to an individual, for example an individual with cancer or an infection, in combination with a population of T cells. The immune cells and the T-cells may be administered to the individual simultaneously or sequentially.

In other embodiments, the FAMIN deficient immune cells may be used to expand or activate T cells in vitro. T cells activated with FAMIN deficient immune cells displaying a target antigen are shown herein to have increased cytolytic activity relative to T cells activated with control immune cells displaying the target antigen. For example, an in vitro method of activating antigen-specific T cells comprising;

providing a population of T cells, culturing the T cells with a population of immune cells having reduced FAMIN activity and displaying a target antigen, thereby producing an activated T cell population specific for the displayed target antigen.

Suitable immune cells for use in the activation of T cells include dendritic cells.

The T cells may be naïve T cells or may be antigen-specific T cells, for example tumour antigen specific T cells. Suitable T cells may include CD8+ cytotoxic T cells and CD4+ T helper cells.

Suitable techniques for generating immune cells displaying a target antigen of interest are well known in the art. Suitable target antigens include tumor antigens or tumor associated antigens expressed by cancer cells in an individual.

A population of T cells activated in vitro using immune cells having reduced FAMIN activity may be useful in stimulating cell-mediated immune responses in an individual for example in a method of immunotherapy, such as cancer immunotherapy.

T cells administered with FAMIN deficient immune cells or activated by FAMIN deficient immune cells in vitro before administration, may be specifically targeted to specific target cells in the individual, such as cancer cells. For example, the T cells may express an antigen receptor which binds specifically to the cancer cells in the individual. The antigen receptor may bind to a tumour antigen that is expressed by some or all of the individual's cancer cells. Suitable receptors include endogenous T cell receptors (TCR) or a heterologous antigen receptor such as a chimeric antigen receptor, T body receptor or heterologous αβTCR heterodimer.

The generation of T cells that target cancer cells in an individual and their use in cancer immunotherapy is well-known in the art.

Another aspect of the invention provides a method of stimulating a cell-mediated immune response in an individual in need thereof comprising administering to an individual in need thereof a population of T cells activated in vitro by immune cells having reduced FAMIN activity.

Preferably, the individual has cancer and the method is a method of cancer immunotherapy. The T cells may be specific for an antigen expressed by cancer cells in the individual.

Whilst a therapeutic agent described above, such as a FAMIN antagonist or inhibitor, suppressor nucleic acid, targetable nuclease, nucleic acid encoding a suppressor nucleic acid or targetable nuclease, FAMIN deficient immune cell or T cell activated by FAMIN deficient immune cells, may be administered alone, the therapeutic agent will usually be administered in the form of a pharmaceutical composition, which may comprise at least one component in addition to the active agent. A therapeutic agent may be admixed with other reagents, such as buffers, carriers, diluents, preservatives and/or pharmaceutically acceptable excipients in order to produce a pharmaceutical composition for use in cancer immunotherapy. Suitable reagents are described in more detail below.

Aspects of the invention provide (i) a pharmaceutical composition comprising a therapeutic agent selected from (a) a FAMIN antagonist or inhibitor (b) FAMIN suppressor nucleic acid, (c) FAMIN targetable nuclease, (d) nucleic acid encoding a FAMIN suppressor nucleic acid or targetable nuclease, and (e) a population of FAMIN deficient immune cells and/or T cells as described herein, and a pharmaceutically acceptable excipient and (ii) a method of producing a pharmaceutical composition for use in cancer immunotherapy comprising admixing a therapeutic agent as described above with a pharmaceutically acceptable excipient.

The term "pharmaceutically acceptable" as used herein pertains to compounds, materials, compositions, and/or dosage forms which are, within the scope of sound medical judgement, suitable for use in contact with the tissues of a subject (e.g., human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Pharmaceutical compositions suitable for administration (e.g. by infusion), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents. Examples of suitable isotonic vehicles for use in such formulations include Sodium Chloride Injection, Ringer's Solution, or Lactated Ringer's Injection. Suitable vehicles can be found in standard pharmaceutical texts, for example, Remington's Pharmaceutical Sciences, 18th edition, Mack Publishing Company, Easton, Pa., 1990.

In some embodiments, the therapeutic agent may be a population of FAMIN deficient immune cells and/or T cells as described herein. The population may be formulated into a pharmaceutical composition suitable for intravenous infusion into an individual. Typically, the number of cells administered is from about $10^5$ to about $10^{10}$ per Kg body weight, typically $10^8$-$10^{10}$ cells per individual, typically over the course of 30 minutes, with treatment repeated as necessary, for example at intervals of days to weeks.

The population of FAMIN deficient immune cells and/or T cells may be autologous i.e. the immune cells were originally obtained from the same individual to whom the FAMIN deficient immune cells and/or T cells are subsequently administered (i.e. the donor and recipient individual are the same). A suitable population of FAMIN deficient immune cells for administration to a recipient individual may be produced by a method comprising providing an initial population of immune cells obtained from the individual, reducing or abolishing FAMIN expression or activity in the immune cells to produce a population of FAMIN deficient immune cells and expanding the population of FAMIN deficient immune cells. A suitable population of T cells for administration to a recipient individual may be produced by a method comprising providing an initial population of naïve T cells obtained from the individual, activating the T cells with FAMIN deficient immune cells to produce an activated T cell population and expanding the activated T cell population.

The population of FAMIN deficient immune cells and/or T cells may be allogeneic i.e. the immune cells were originally obtained from a different individual to the individual to whom the FAMIN deficient immune cells and/or T cells are subsequently administered (i.e. the donor and recipient individual are different). The donor and recipient individuals may be HLA matched to avoid GVHD and other undesirable immune effects. A suitable population of FAMIN deficient immune cells for administration to a recipient individual may be produced by a method comprising providing an initial population of immune cells obtained from a donor individual, reducing or abolishing FAMIN expression or activity in the immune cells to produce a population of FAMIN deficient immune cells, and expanding the population of FAMIN deficient immune cells. A suitable population of T cells for administration to a recipient individual may be produced by a method comprising providing an initial population of naïve T cells obtained from a donor individual, activating the T cells with FAMIN deficient immune cells to produce an activated T cell population and expanding the activated T cell population.

A therapeutic agent or the pharmaceutical composition comprising the therapeutic agent as described herein may be administered to a subject by any convenient route of administration, whether systemically/peripherally or at the site of desired action, including but not limited to; parenteral, for example, by infusion, including intravenous infusion, in particular intravenous bolus infusion. Suitable infusion techniques are known in the art and commonly used in therapy (see, e.g., Rosenberg et al., New Eng. J. of Med., 319:1676, 1988).

It will be appreciated that appropriate dosages of the therapeutic agent, and compositions comprising the therapeutic agent, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular cells, the route of administration, the time of administration, the rate of loss or inactivation of the cells, the duration of the treatment, other drugs, compounds, and/or materials used in combination, and the age, sex, weight, condition, general health, and prior medical history of the patient. The amount of cells and the route of administration will ultimately be at the discretion of the physician, although generally the dosage will be to achieve local concentrations at the site of action which achieve the desired effect without causing substantial harmful or deleterious side-effects.

A typical oral dosage of a small molecule inhibitor is in the range of from about 0.05 to about 1000 mg, preferably from about 0.1 to about 500 mg, and more preferred from about 1.0 mg to about 200 mg administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art. For parenteral routes such as intravenous, intrathecal, intramuscular and similar administration, typically doses are in the order of about half the dose employed for oral administration.

A therapeutic agent, such as (a) a FAMIN antagonist or inhibitor (b) FAMIN suppressor nucleic acid, (c) a FAMIN targetable nuclease, (d) nucleic acid encoding a FAMIN suppressor nucleic acid or targetable nuclease, or (e) a population of FAMIN deficient immune cells and/or T cells as described herein, may be useful in therapy. For example, a therapeutic agent which reduces FAMIN activity may be administered to an individual for the treatment of cancer.

Therapeutic agents described above are shown herein to be useful in the treatment of cancer through effects on tumourigenesis and/or tumour immune surveillance.

Cancer is characterised by the abnormal proliferation of malignant cancer cells and may include leukaemia, such as AML, CML, ALL and CLL, lymphoma, such as Hodgkin lymphoma, non-Hodgkin lymphoma and multiple myeloma, and solid cancers such as sarcomas, skin cancer, melanoma, bladder cancer, brain cancer, breast cancer, uterus cancer, oral cancer, ovary cancer, prostate cancer, lung cancer, colorectal cancer, cervical cancer, liver cancer, head and neck cancer, oesophageal cancer, pancreas cancer, renal cancer, adrenal cancer, stomach cancer, testicular cancer, cancer of the gall bladder and biliary tracts, thyroid cancer, thymus cancer, cancer of bone, and cerebral cancer.

In some embodiments, the cancer may be an epithelial cancer, such as intestinal or colorectal cancer or oral cancers.

Cancerous cells may be immunologically distinct from normal somatic cells in an individual with cancer suitable for treatment as described herein (i.e. the cancerous tumour may be immunogenic). For example, cancerous cells may be capable of eliciting a systemic immune response in the individual against one or more antigens expressed by the cancer cells. The antigens that elicit the immune response may be tumour antigens or may be shared by normal cells.

An individual suitable for treatment with a therapeutic agent, such as (a) a FAMIN antagonist or inhibitor (b) FAMIN suppressor nucleic acid, (c) FAMIN targetable nuclease, (d) nucleic acid encoding a FAMIN suppressor nucleic acid or targetable nuclease, or (e) a population of FAMIN deficient immune cells and/or T cells as described herein, may be a mammal, such as a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orangutan, gibbon), or a human.

In some preferred embodiments, the individual is a human. In other preferred embodiments, non-human mammals, especially mammals that are conventionally used as models for demonstrating therapeutic efficacy in humans (e.g. murine, primate, porcine, canine, or rabbit animals) may be employed.

In some embodiments, the individual may have minimal residual disease (MRD) after an initial cancer treatment.

An individual with cancer may display at least one identifiable sign, symptom, or laboratory finding that is sufficient to make a diagnosis of cancer in accordance with clinical standards known in the art.

Examples of such clinical standards can be found in textbooks of medicine such as Harrison's Principles of Internal Medicine, 15th Ed., Fauci A S et al., eds., McGraw-Hill, New York, 2001. In some instances, a diagnosis of a cancer in an individual may include identification of a particular cell type (e.g. a cancer cell) in a sample of a body fluid or tissue obtained from the individual.

The term "treatment", as used herein in the context of treating a condition, pertains generally to treatment and therapy in which some desired therapeutic effect is achieved, for example, the inhibition of the progress of the condition, and includes a reduction in the rate of progress, a halt in the rate of progress and amelioration of the condition, and cure of the condition.

Treatment may be any treatment and therapy, whether of a human or an animal (e.g. in veterinary applications), in which some desired therapeutic effect is achieved, for example, the inhibition or delay of the progress of the condition, and includes a reduction in the rate of progress, a halt in the rate of progress, amelioration of the condition, cure or remission (whether partial or total) of the condition, preventing, delaying, abating or arresting one or more symptoms and/or signs of the condition or prolonging survival of a subject or patient beyond that expected in the absence of treatment.

Treatment as a prophylactic measure (i.e. prophylaxis) is also included. For example, an individual susceptible to or at risk of the occurrence or re-occurrence of cancer may be treated as described herein. Such treatment may prevent or delay the occurrence or re-occurrence of cancer in the individual.

In particular, treatment may include inhibiting cancer growth, including complete cancer remission, and/or inhibiting cancer metastasis. Cancer growth generally refers to any one of a number of indices that indicate change within the cancer to a more developed form. Thus, indices for measuring an inhibition of cancer growth include a decrease in cancer cell survival, a decrease in tumor volume or morphology (for example, as determined using computed tomographic (CT), sonography, or other imaging method), a delayed tumor growth, a destruction of tumor vasculature, improved performance in delayed hypersensitivity skin test, an increase in the activity of cytolytic immune cells, and a decrease in levels of tumor-specific antigens. Reducing immune suppression in cancerous tumours in an individual may improve the capacity of the individual to resist cancer growth, in particular growth of a cancer already present the subject and/or decrease the propensity for cancer growth in the individual.

A therapeutic agent, such as (a) a FAMIN antagonist or inhibitor (b) FAMIN suppressor nucleic acid, (c) FAMIN targetable nuclease, (d) nucleic acid encoding a FAMIN suppressor nucleic acid or targetable nuclease, or (e) a population of FAMIN deficient immune cells and/or T cells as described herein, may also be useful in the treatment of infection through the stimulation of cell-mediated immunity.

For example, an individual treated as described herein may have an infection, for example a viral, bacterial or fungal infection.

A therapeutic agent, such as (a) a FAMIN antagonist or inhibitor (b) FAMIN suppressor nucleic acid, (c) FAMIN targetable nuclease, (d) nucleic acid encoding a FAMIN suppressor nucleic acid or targetable nuclease or (e) a population of FAMIN deficient immune cells and/or T cells as described herein may be administered in combination with one or more other therapies, such as cytotoxic chemotherapy or radiotherapy.

While it is possible for a therapeutic agent to be administered alone, it may be preferable in some circumstances to administer the therapeutic agent in combination with one or more additional therapeutic agents.

Suitable additional therapeutic agents may include anti-cancer agents, populations of T-cells, tumour antigens, cytokines, such as IL-2 or other immunotherapy and cytostatic agents, including immune checkpoint inhibitors, for example anti-CTLA4 antibodies, such as ipilimumab, anti-PD-1 antibodies such as pembrolizumab and nivolumab, and anti-PD-L1 antibodies, such as atezolizumab.

Examples of suitable anti-cancer agents include chemotherapeutic agents, for example alkylating agents such as platinum complexes including cisplatin, mono(platinum), bis(platinum), tri-nuclear platinum complexes and carboplatin, thiotepa and cyclosphosphamide (CYTOXAN); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU) gemcitabine, fluorouracil, capecitabine, methotrexate sodium, ralitrexed, pemetrexed, tegafur, cytosine arabinoside, thioguanine, 5-azacytidine, 6-mercaptopurine, azathioprine, 6-thioguanine, pentostatin, pitavastatin, fludarabine phosphate, and cladribine; folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytosine arabinoside, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenishers such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); taxoids, e.g. paclitaxel (TAXOL) and docetaxel (TAXOTERE); chlorambucil; gemcitabine; 6-thioguanine; mercaptopurine; platinum analogs such as cisplatin and carboplatin; vinblastine; platinum; etoposide (VP-16); ifosfamide; mitomycin C; mitoxantrone; vincristine; vinorelbine; binblastine; vindesine; navelbine; novantrone; teniposide; daunomycin; aminopterin; ibandronate; CPT11; topoisomerase inhibitor RFS 2000; difluoromethylornithine (DMFO); retinoic acid; esperamicins; capecitabine (XELODA); Topoisomerase inhibitors such as doxorubicin HCl, daunorubicin citrate, mitoxantrone HCl, actinomycin D, etoposide, topotecan HCl, teniposide (VM-26), and irinotecan and pharmaceutically acceptable salts, acids or derivatives of any of the above.

When the therapeutic agents are used in combination with additional therapeutic agents, the compounds may be administered either sequentially or simultaneously by any convenient route.

When a therapeutic agent is used in combination with an additional therapeutic agent active against the same disease, the dose of each agent in the combination may differ from that when the therapeutic agents are used alone. Appropriate doses will be readily appreciated by those skilled in the art.

The one or more additional therapeutic agents may be administered by any convenient means.

Administration of therapeutic agents, such as (a) FAMIN antagonists or inhibitors (b) FAMIN suppressor nucleic acids (c) FAMIN targetable nucleases (d) nucleic acids encoding FAMIN suppressor nucleic acids or targetable nucleases, and (e) populations of FAMIN deficient immune cells and/or T cells as described herein, can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

Another aspect of the invention provides a kit comprising a population of immune cells, preferably DCs, with reduced FAMIN activity for use in activating T cells in vitro as described above.

The kit may further comprise a chemically defined basal medium, a supplement as described above and/or one or more other cell culture ingredients selected from the group consisting of amino acids, vitamins, inorganic salts, carbon energy sources, buffers, IL-4, GM-CSF, transferrin, 1-thioglycerol and defined lipids.

The components of the kit may be contained in separate hermetically-sealed vessels.

Kits as described above for activating T cells in vitro may further comprise a cell culture vessel. Suitable cell culture vessels, such as flasks, single or multiwell plates, single or multiwell dishes, bottles, jars, vials, bags and bioreactors, are well-known in the art.

Another aspect of the invention provides the use of a population of immune cells, preferably DCs, with reduced FAMIN activity as described above in a method for the in vitro activation of T cells.

Other aspects and embodiments of the invention provide the aspects and embodiments described above with the term "comprising" replaced by the term "consisting of" and the aspects and embodiments described above with the term "comprising" replaced by the term "consisting essentially of".

It is to be understood that the application discloses all combinations of any of the above aspects and embodiments described above with each other, unless the context demands otherwise. Similarly, the application discloses all combinations of the preferred and/or optional features either singly or together with any of the other aspects, unless the context demands otherwise.

Modifications of the above embodiments, further embodiments and modifications thereof will be apparent to the skilled person on reading this disclosure, and as such, these are within the scope of the present invention.

All documents and sequence database entries mentioned in this specification are incorporated herein by reference in their entirety for all purposes.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Certain aspects and embodiments of the invention will now be illustrated by way of example and with reference to the figures described above.

Experiments

Figure 1B:
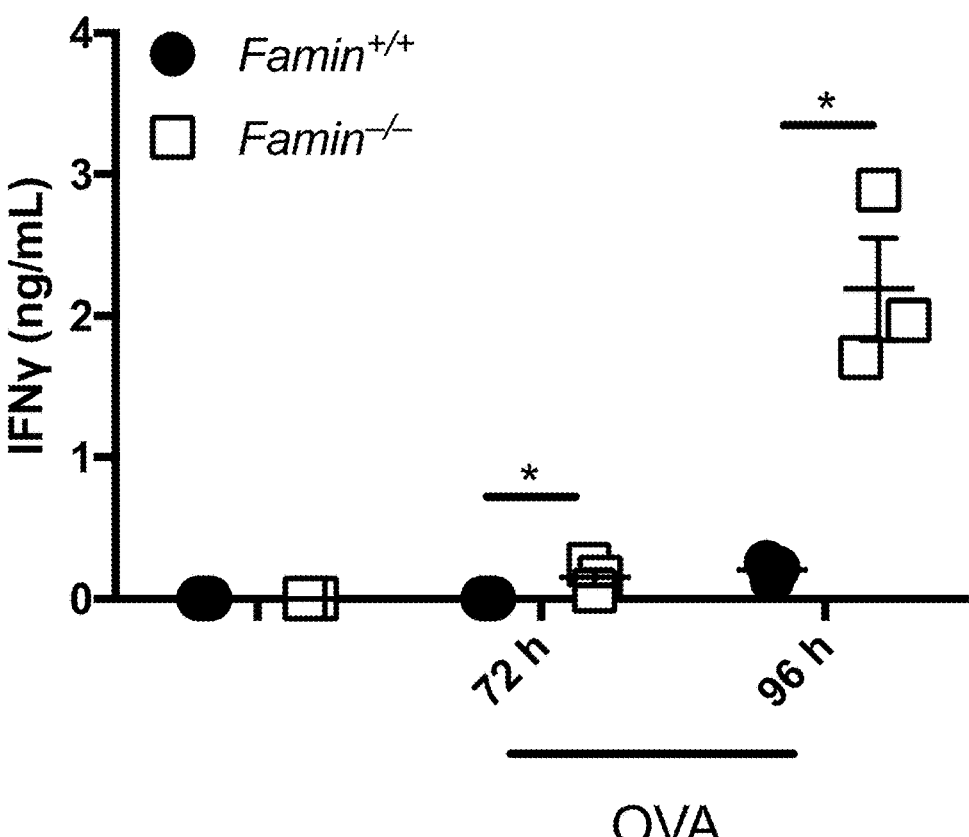
FIGS. 1B and 1C show the IFNγ and IL-2 secretion, respectively, of OT-II cells that had been activated and differentiated by co-culture of naïve OT-II cells with Famin$^{-/-}$ and Famin$^{+/+}$ DCs.
Figure 1C:
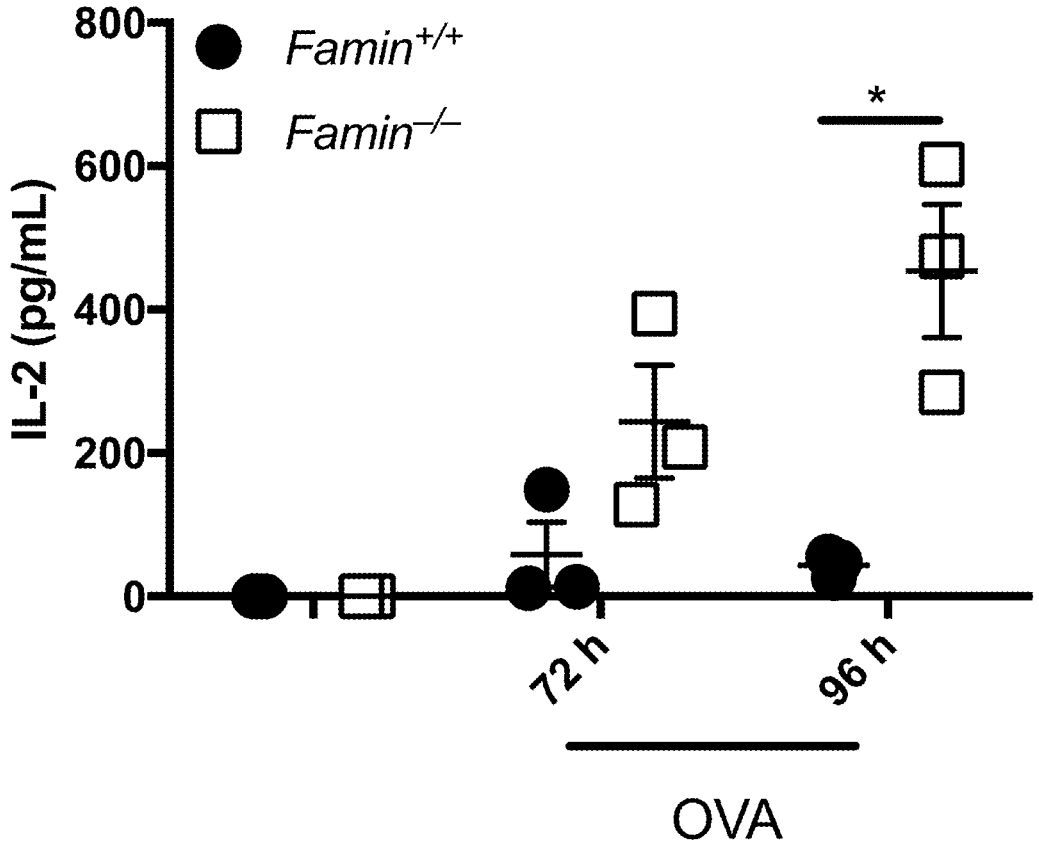

FAMIN (also known as LACC1 or C13orf31) controls adaptive immune responses Dendritic cells (DCs) presenting antigen to naïve T cells elicit antigen-specific adaptive MHC class I-and class II-restricted T cell responses. We hypothesised that FAMIN may control adaptive immune function. To assess this directly, we generated mice with a DC-specific deletion of Famin by crossing a Cd11c-Cre mouse line with $Famin^{fl/fl}$ mice to generate $Famin^{\Delta DC}$ mice ($Cd11c\text{-}Cre^{pos}$; $Famin^{fl/fl}$) and their $Famin^{WT}$ littermate controls ($Cd11c\text{-}Cre^{neg};Famin^{fl/fl}$). We also generated $Famin^{p.254I}$, $Famin^{p.254V}$ and $Famin^{p.284R}$ mice, which carry germ-line point mutations in their endogenous Famin gene that lets them express $FAMIN^{254I}$, $FAMIN^{254V}$ and $FAMIN^{284R}$ variants of the protein, which are associated with human disease. Decreased FAMIN Function Amplifies CD4 and CD8 T Cell Responses To assess how FAMIN function in DCs impacts on priming and differentiation of naïve T cells and their restimulation, we chose ovalbumin as model antigen and T cells from OT-I and OT-II mice that transgenically express cognate OVA peptide-specific MHC I and MHC II-restricted T cell receptors (TCRs), respectively. We co-cultured splenic $CD11c^+$ DCs pulsed with the I-Ad-restricted OVA MHC class II epitope $OVA^{323\text{-}339}$ (ISQAVHAA-HAEINEAGR (SEQ ID NO: 7)) with $OT\text{-}II;Rag2^{-/-}$ T cells that had been labelled with carboxyfluorescein succinimidyl ester (CFSE), which allows assessing proliferation due to the progressive halving of CFSE fluorescence within daughter cells following each cell division. As shown in FIG. 1A, OT-II cells co-cultured with $Famin^{-/-}$ DCs exhibited a higher division index compared to those co-cultured with $Famin^{+/+}$ DCs. Moreover, IFNγ (FIG. 1B) and IL-2 (FIG. 1C) secretion into the co-culture supernatant was profoundly increased when OT-II cells were primed with $Famin^{-/-}$ compared with $Famin^{+/+}$ DCs.

Figure 2A:
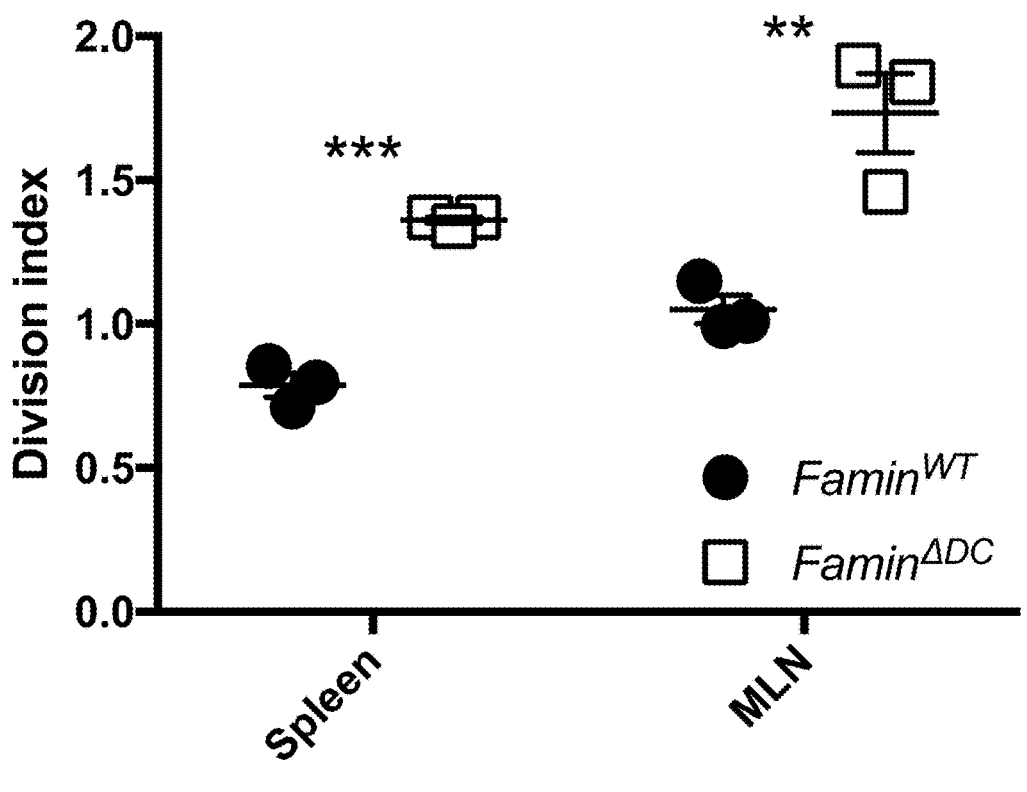
FIG. 2A shows the division index of OT-II T cells in mice with a DC-specific deletion of Famin ('Famin$^{\Delta DC}$') compared to wild-type controls ('Famin$^{WT}$').
Figure 2B:
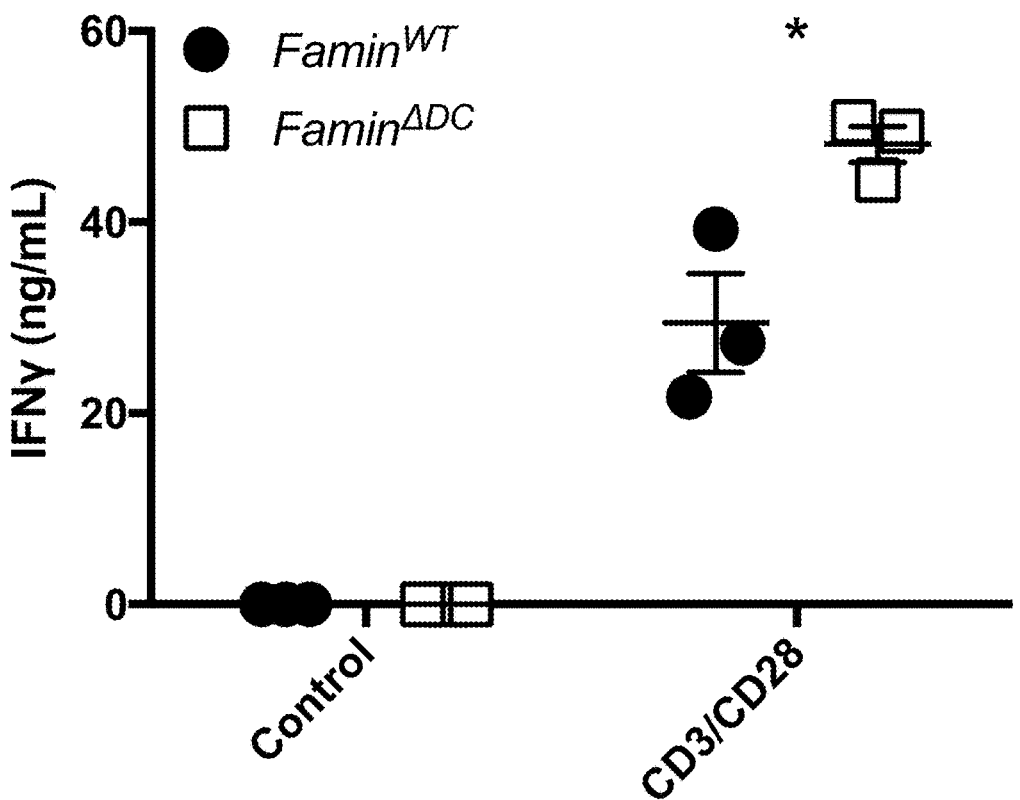
FIG. 2B shows IFNγ secretion of anti-CD3 and anti-CD28 re-stimulated splenocytes isolated from Famin$^{\Delta DC}$ and Famin$^{WT}$ mice that had received OT-II cells and OVA as antigen.

To assess CD4$^+$ T cell priming and activation in vivo, we intravenously injected 7.5×10$^6$ CFSE-labelled CD4$^+$ OT-II cells, obtained from OT-II; Rag2$^{-/-}$ mice, into Famin$^{\Delta DC}$ and Famin$^{WT}$ mice that were intraperitoneally immunised on day 2 with 25 µg OVA. Lymphocytes were harvested from mesenteric lymph nodes (MLN) and spleens. Consistent with results from the reductionist in vitro study, OT-II cells transferred into Famin$^{\Delta DC}$ mice exhibited higher division indices in MLN and spleen (FIG. 2A), compared to those injected into their respective Famin$^{WT}$ controls. Re-stimulation with anti-CD3$^+$ anti-CD28 in vitro resulted in increased IFNγ (FIG. 2B) secretion from splenocytes isolated from Famin$^{\Delta DC}$ mice that had received OT-II cells, compared to those obtained from OT-II-transferred Famin$^{WT}$ mice.

Figure 2C:
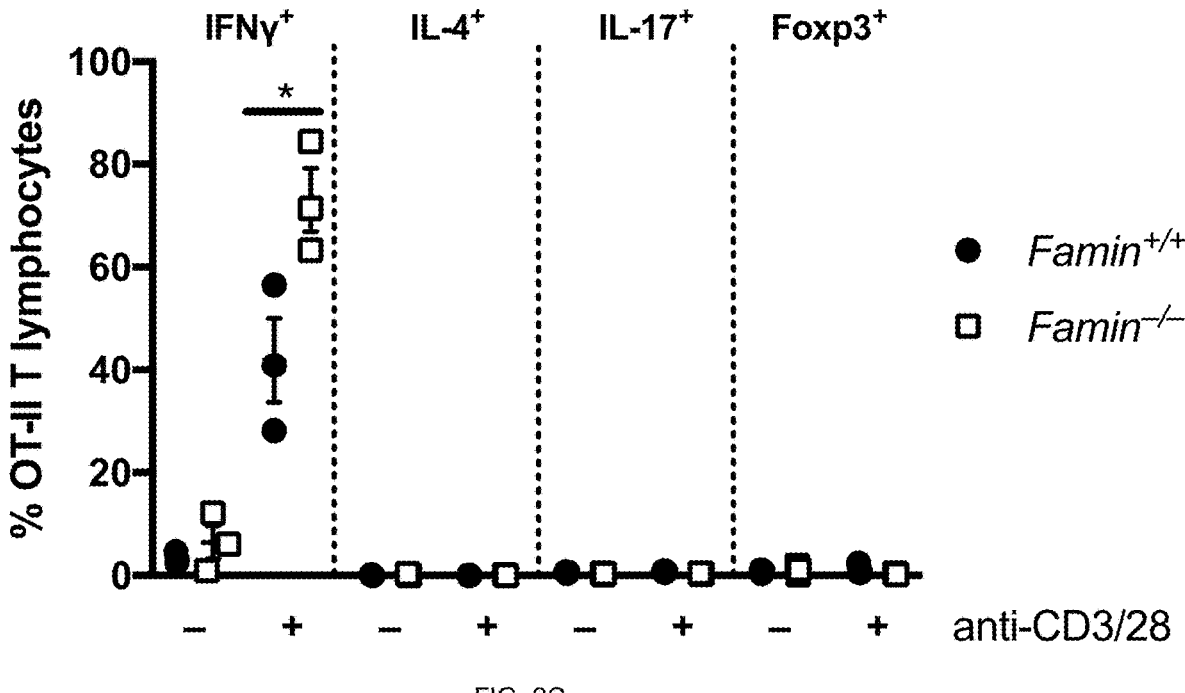
FIG. 2C shows the intracellular cytokine and transcription factor expression of anti-CD3 and anti-CD28 re-stimulated CD4$^+$ OT-II cells co-cultured in vitro with OVA-pulsed cDC2 cells.

Using the reductionistic co-culture system of CD4$^+$ OT-II cells and OVA-pulsed DCs as described above (here using cDC2, which were either derived from Famin$^{+/+}$ or Famin$^{-/-}$ mice) to prime T cell responses, we re-stimulated the resulting T cell population with anti-CD3$^+$ anti-CD28 to investigate their intracellular cytokine and transcription factor expression. FIG. 2C shows an almost doubling in the percentage of T cells expressing IFNγ, while the proportion of IL-4$^+$, IL-17$^+$ and FoxP3$^+$ T cells did not increase.

Figure 3A:
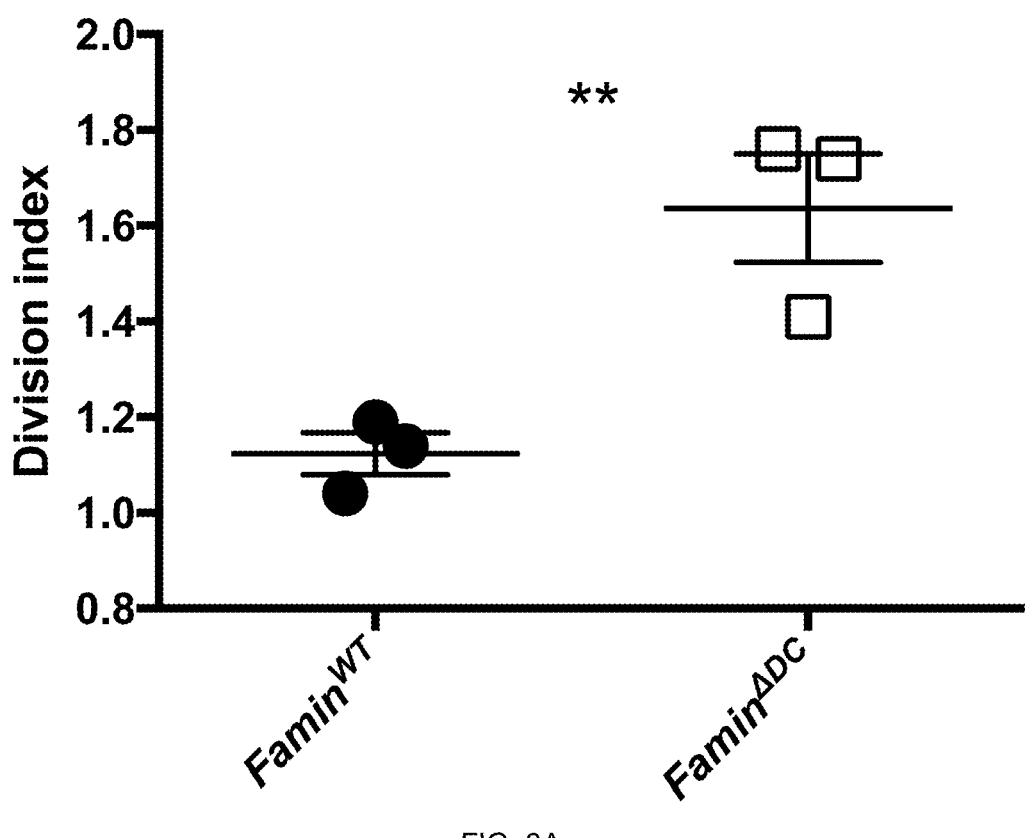
FIG. 3A shows the division index of OT-I T cells after priming in vitro with OVA antigen-presenting Famin$^{WT}$ or Famin$^{\Delta DC}$ DCs.
Figure 3B:
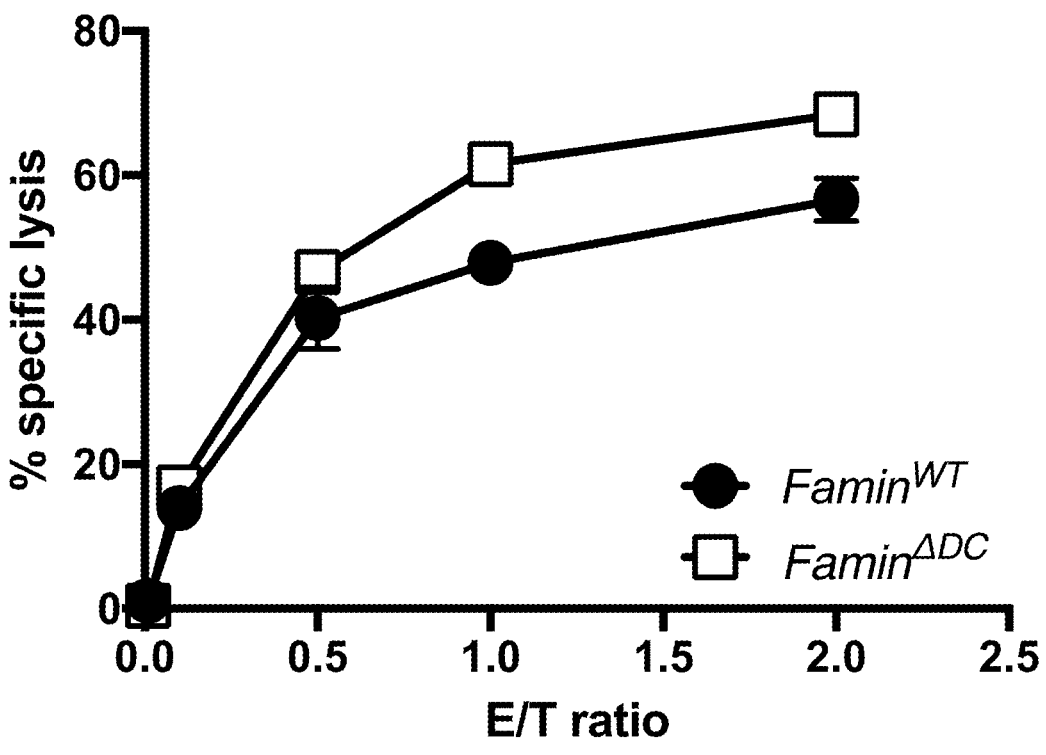
FIGS. 3B, 3C and 3D show the cytotoxicity, amount of granzyme B and IFNγ secretion, respectively of OT-I cells activated by DCs from Famin$^{\Delta DC}$ and Famin$^{WT}$ mice.
Figure 3C:
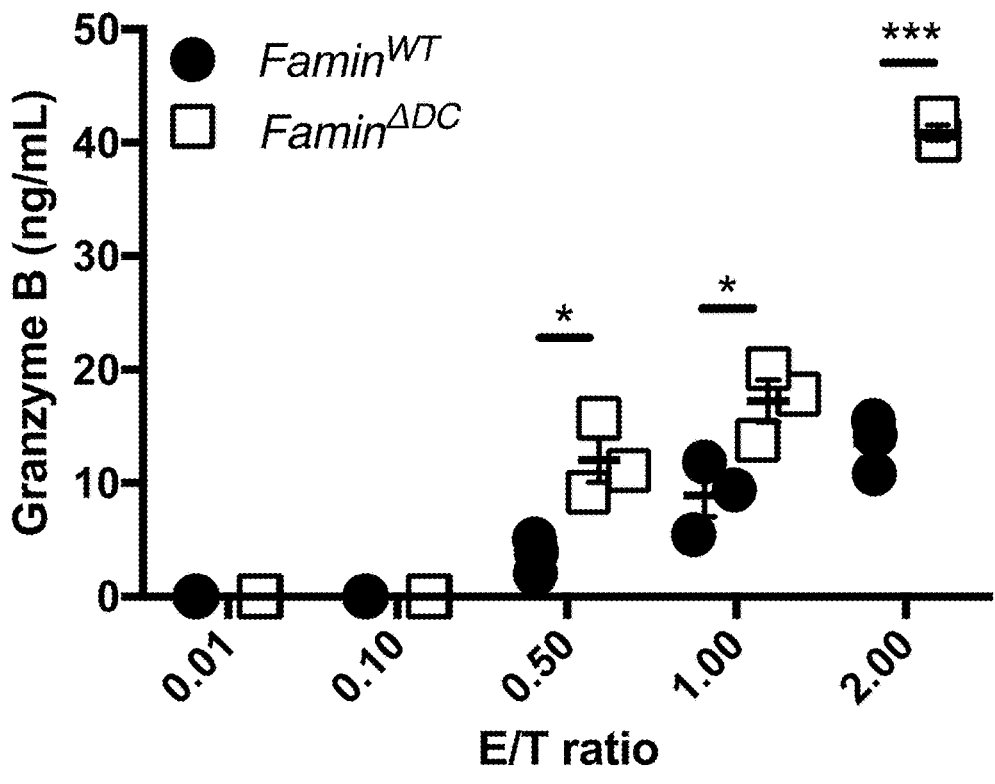
Figure 3D:
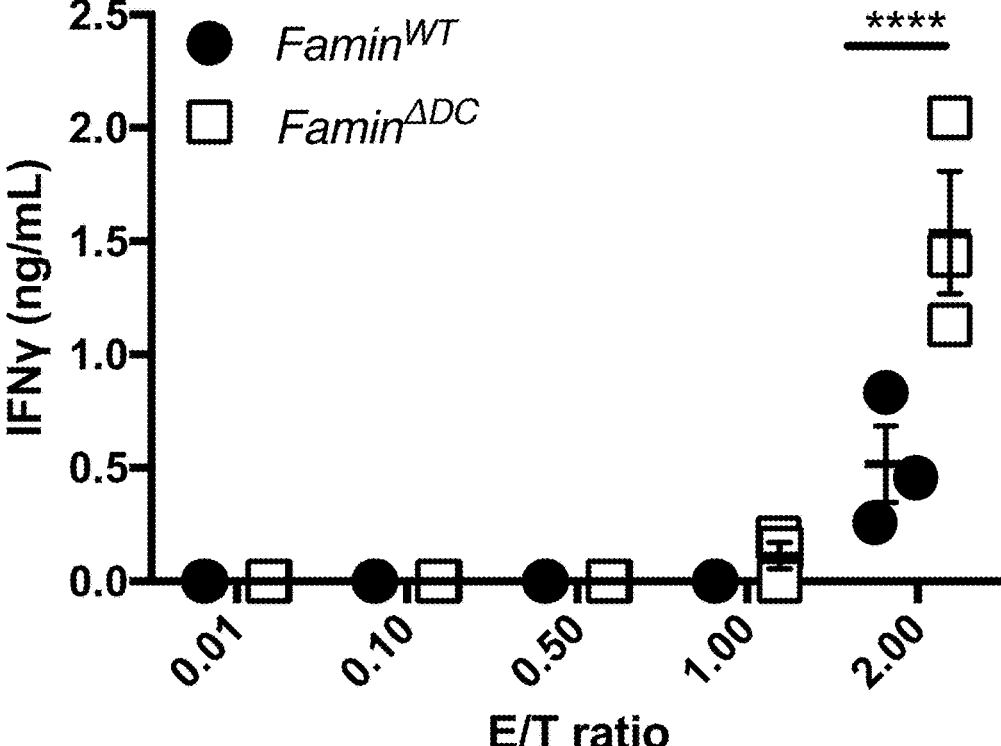

To assess whether DC-intrinsic FAMIN affects their capacity to prime CD8$^+$ cytotoxic T lymphocytes (CTL), we pulsed splenic CD11c$^+$ DCs isolated from Famin$^{\Delta DC}$ and Famin$^{WT}$ mice with the H-2Kb-restricted OVA MHC class I epitope OVA$^{257-264}$ (SIINFEKL (SEQ ID NO: 8)), and co-cultured them in vitro with T cells from OT-I; Rag$^{-/-}$ mice for 72 h. As depicted in FIG. 3A, OT-I cells primed by OVA$^{257-264}$-pulsed Famin$^{\Delta DC}$ exhibited a higher division index compared to those primed by OVA$^{257-264}$-pulsed Famin$^{WT}$ splenic DCs. In separate experiments, we passaged and hence rested proliferating lymphocytes for 6 days after priming of naïve OT-I T cells by co-culture with OVA$^{257-264}$-pulsed Famin$^{\Delta DC}$ and Famin$^{WT}$ splenic DCs. Cytotoxicity was then assessed against OVA$^{257-264}$-pulsed wild-type splenocytes at various effector: target (E:T) ratios. As depicted in FIG. 3B, OT-I cells primed by DCs from Famin$^{\Delta DC}$ mice exhibited increased cytotoxicity compared to those primed by Famin$^{WT}$ DCS. Consistent with such increased cytotoxicity, the levels of the major cytotoxic mediator of CTLs, granzyme B, in co-cultures were substantially higher when OT-I cells had been primed by Famin$^{\Delta DC}$ DCs compared to those primed by Famin$^{WT}$ DCs (FIG. 3C). OT-I cells primed by Famin$^{\Delta DC}$ DCs also exhibited higher secretion of IFNγ into the co-culture supernatant compared to those differentiated with Famin$^{WT}$ DCs (FIG. 3D).

Figure 3E:
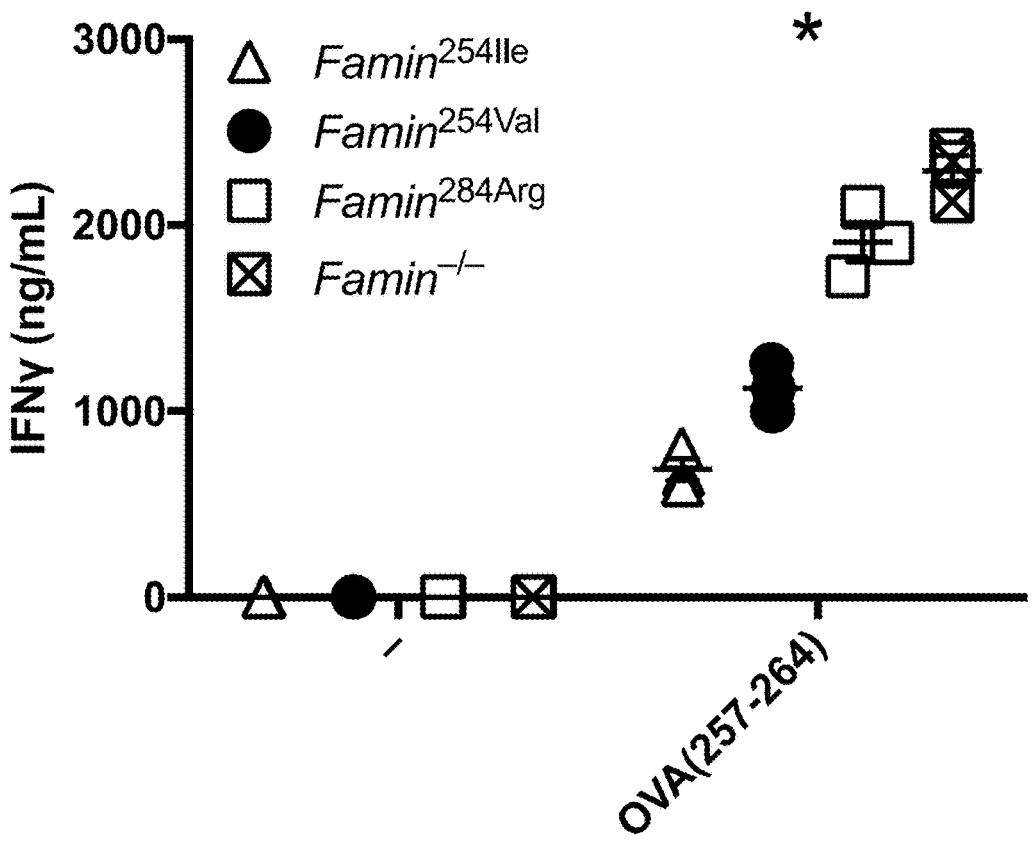
FIG. 3E shows the IFNγ secretion of OT-I cells primed by DCs from Famin$^{254Ile}$, Famin$^{254Val}$, Famin$^{284Arg}$ and Famin$^{-/-}$ mice following re-stimulation with cognate OVA peptide after 72 h of DC-OTI co-culture.
Figure 3F:
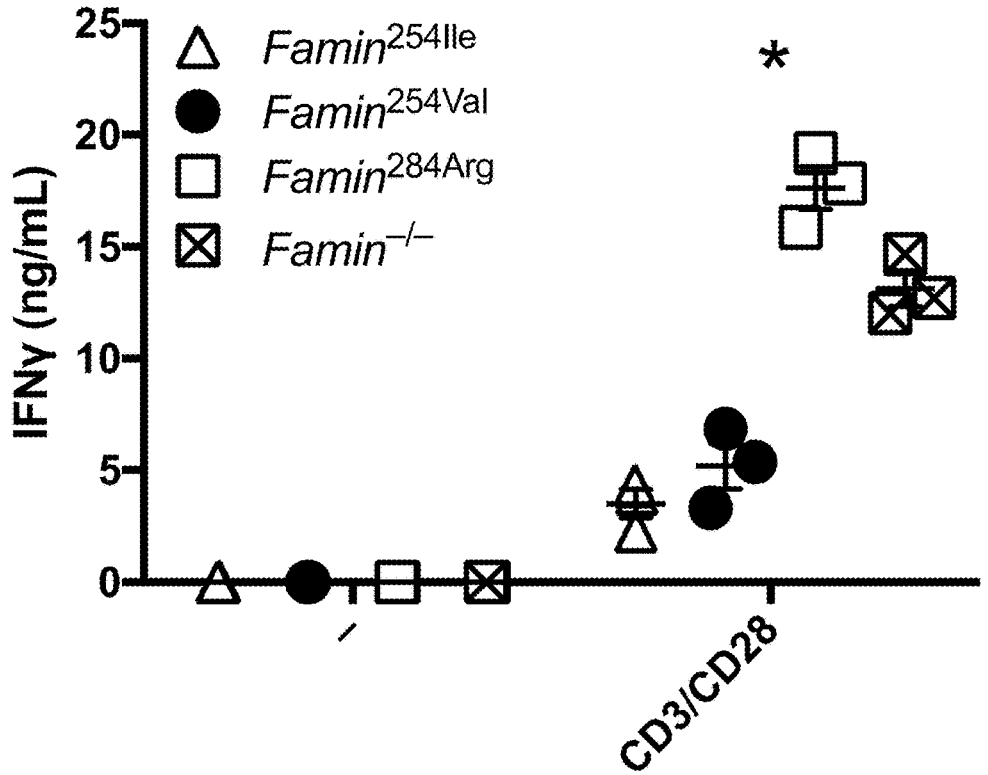
FIG. 3F shows the IFNγ secretion of OT-I cells primed by 72 h of DC-OTI co-culture, then T effector cells were expanded with IL-2 and re-stimulated with anti-CD3 and anti-CD28.
Figure 3G:
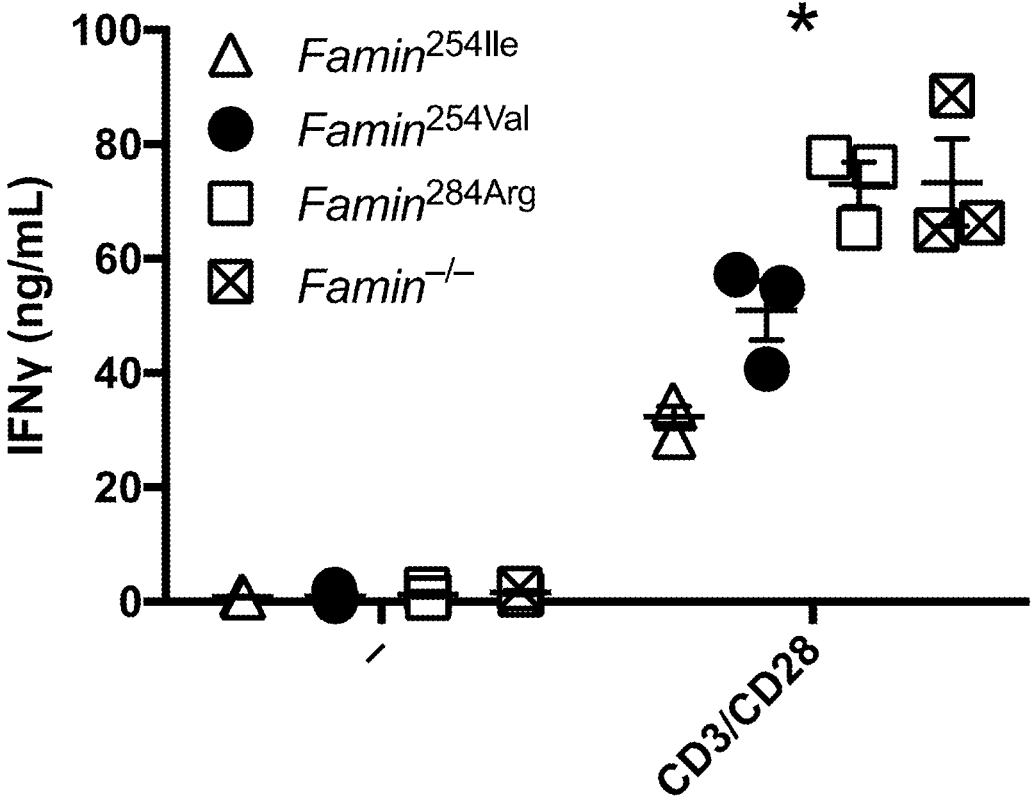
FIG. 3G shows the IFNγ secretion of OT-I cells primed by 72 h of DC-OTI co-culture, then T effector memory (TEM) cells were expanded with IL-15 and re-stimulated with anti-CD3 and anti-CD28.

We next turned to cDC1s derived from Flt3L-cultured bone marrow of mice carrying germ-line mutations in Famin, expressing either isoleucine (Ile, 'Famin$^{254Ile}$') or valine (Val, 'Famin$^{254Val}$') at amino acid position 254, arginine (Arg, 'Famin$^{284Arg}$') at amino acid 284, or a knockout cassette ('Famin$^{-/-}$'). The corresponding human FAMIN$^{254Val}$ variant is hypomorphic and associated with risk for Crohn's disease and leprosy, and homozygosity for FAMIN$^{284Arg}$, a loss-of-function variant, causes a monogenic form of systemic juvenile idiopathic arthritis or early-onset Crohn's disease. Similar to experiments described above, DCs from these various mice were pulsed with OVA$^{257-264}$ peptide and co-cultured with OT-I cells. After 72 h of co-culture T cells were restimulated with OVA$^{257-264}$ peptide, and supernatant assayed for IFNγ (FIG. 3E). Alternatively, T cells were harvested at 72 h and expanded further with IL-2 and IL-15, to generate T effector (TE) and T effector memory (TEM) cells, respectively; TE (FIG. 3F)

and TEM (FIG. 3G) cells were then re-stimulated with anti-CD3$^+$ anti-CD28. FIGS. 3E, F, G show that the hypomorphic and loss-of-function FAMIN variants step-wise increase IFNγ secretion from T cells at each of their differentiation stages. This demonstrates that with decreasing FAMIN function in dendritic cells, the potency of the primed CD8 T cell responses proportionally increases, and this proportionally increased potency is indeed maintained when they differentiate into effector and effector memory T cells.

Figure 4A:
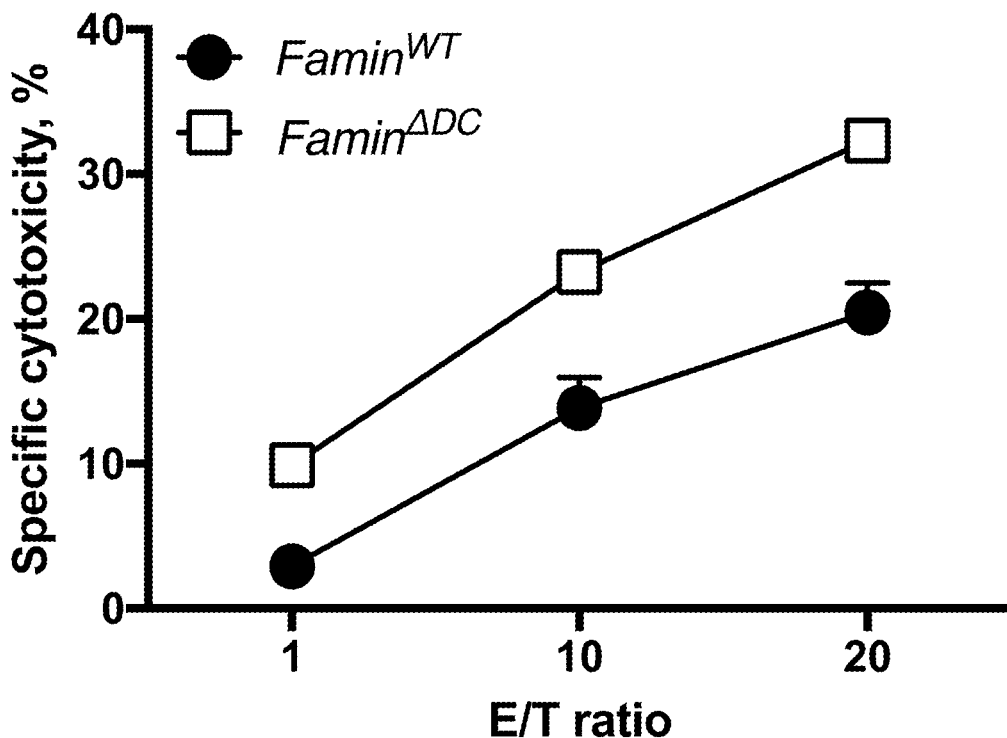
FIGS. 4A, 4B and 4C show the antigen-specific cytotoxicity, amount of granzyme B and IFNγ secretion, respectively, of OT-I CTL cells that had been primed and differentiated in Famin$^{\Delta DC}$ and Famin$^{WT}$ mice.
Figure 4B:
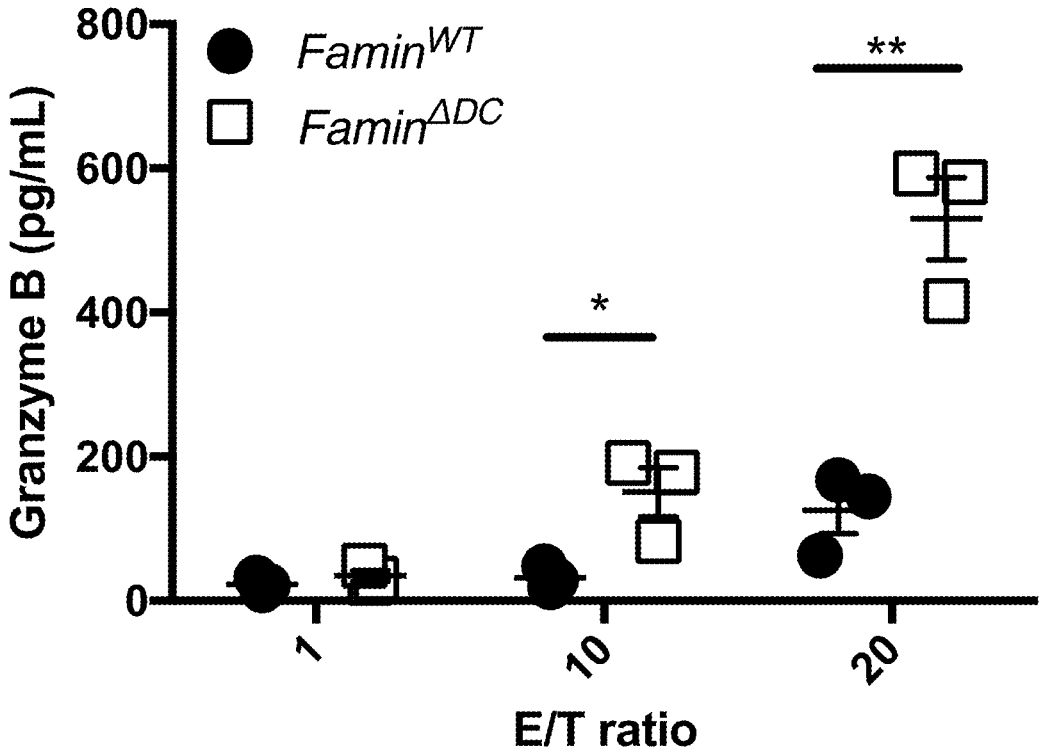
Figure 4C:
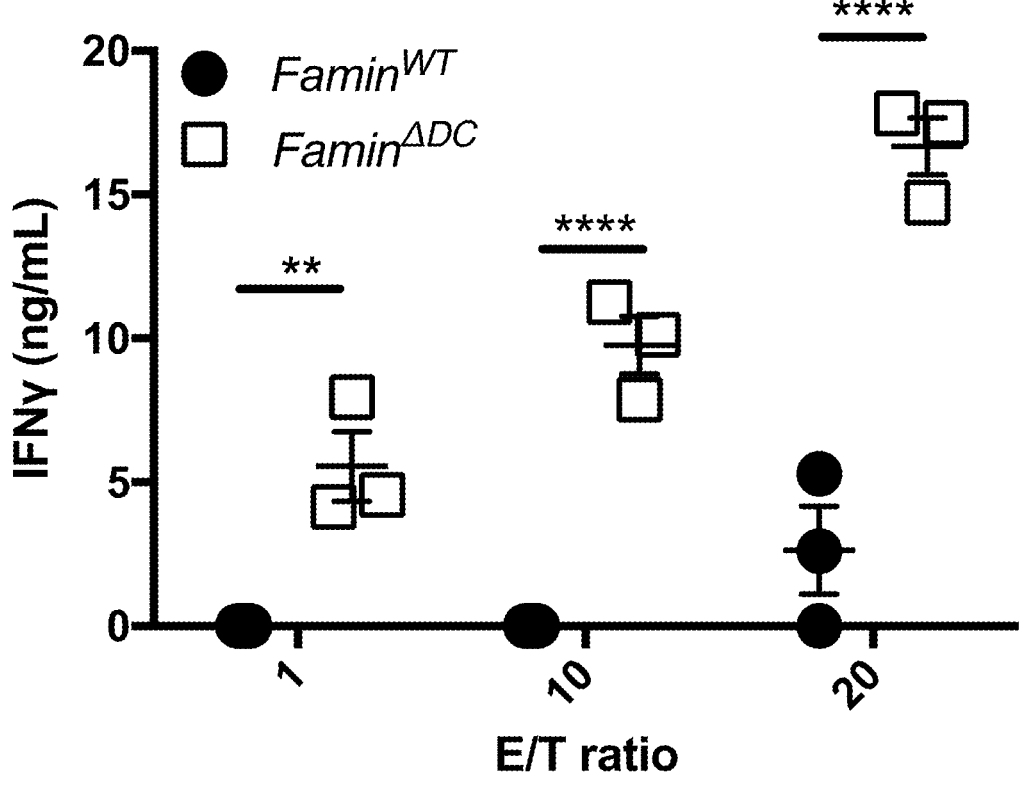

To investigate the differentiation of naïve CD8$^+$ T cells into antigen-specific CTLs in vivo, we injected 7.5×10$^6$ CFSE-labelled OT-I T cells (obtained from OT-I;Rag$^{-/-}$ mice), followed by intraperitoneal immunisation with 25 µg OVA on day 2, and assessment of CTL activity of cells isolated from MLN and spleen on day 5. Antigen-specific cytotoxicity of transferred OT-I cells against OVA$^{257-264}$-pulsed wild-type syngeneic splenocytes was substantially stronger in Famin$^{\Delta DC}$ compared to Famin$^{WT}$ mice (FIG. 4A). Consistent with increased cytotoxicity, granzyme B (FIG. 4B) and IFNγ (FIG. 4C) release into co-cultures with OVA$^{257-264}$-pulsed wild-type syngeneic splenocytes was substantially higher with CTLs obtained from Famin$^{\Delta DC}$ compared to Famin$^{WT}$ mice.

Decreased FAMIN Function Increases Tumour Immune Surveillance

Figure 5A:
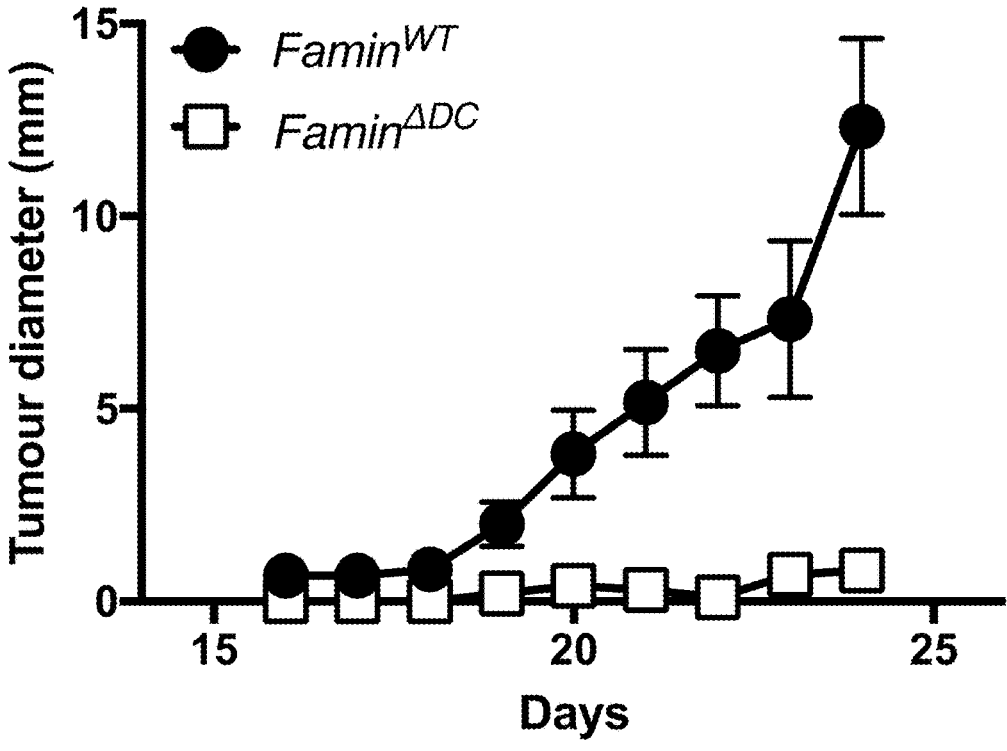
FIG. 5A shows macroscopic tumour growth after subcutaneous injection of 4×10$^4$ Lewis Lung carcinoma LL/2-OVA cells in Famin$^{\Delta DC}$ and Famin$^{WT}$ mice.
Figure 5B:
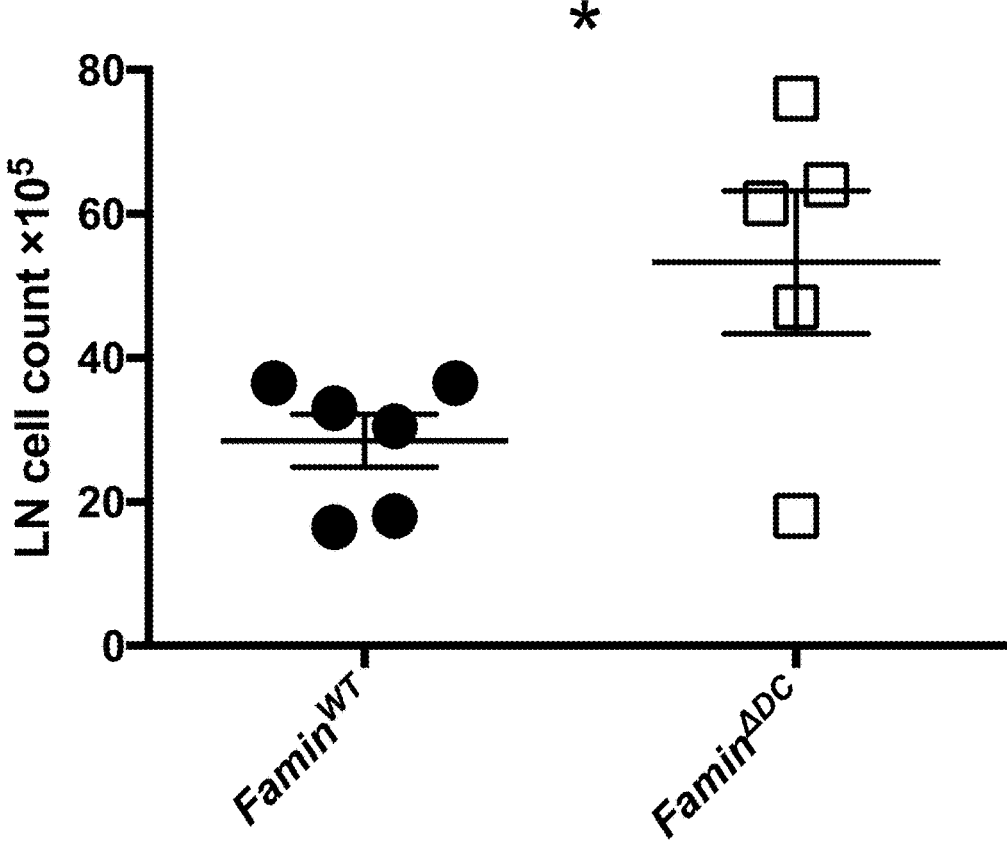
FIG. 5B shows total cell numbers in the inguinal lymph node (LN) draining the LL/2 tumour in Famin$^{\Delta DC}$ and Famin$^{WT}$ mice.
Figure 5C:
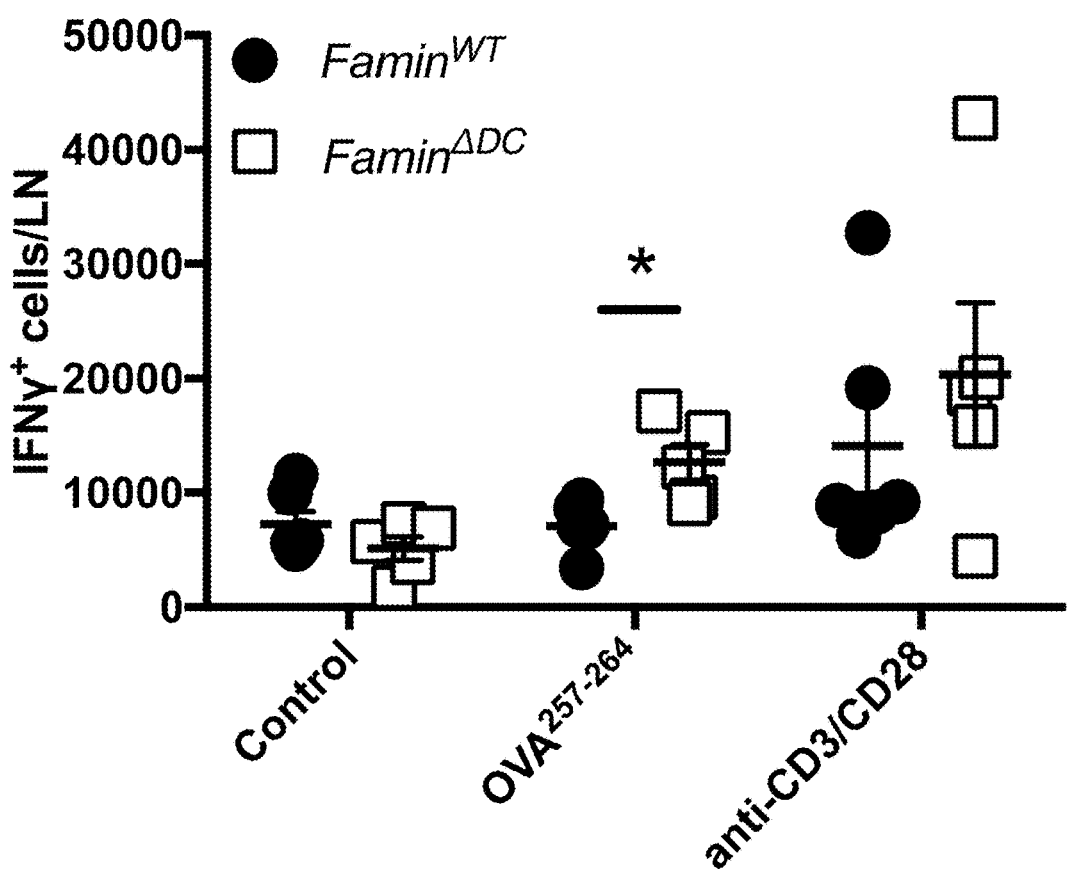
FIG. 5C shows OVA$^{257-264}$-specific and anti-CD3/CD28-elicited IFNγ responses of LN mononuclear cells from LL/2-OVA tumour-carrying Famin$^{WT}$ and Famin$^{\Delta DC}$ mice.

Tumour immune surveillance plays a major role in controlling growth of primary and metastatic tumours. We chose the C57Bl/6-syngenic Lewis lung carcinoma cell line LL/2 engineered to express the model antigen ovalbumin (OVA) as a well-established xenograft tumour model. Macroscopic tumour growth after subcutaneous injection of 4×10$^4$ LL/2-OVA cells became detectable from day 19 onwards in Famin$^{WT}$ mice, and tumour diameter continually increased in subsequent days. In stark contrast, no appreciable tumour was observed in Famin$^{\Delta DC}$ mice until the end of the observation period at that 24 (FIG. 5A). IFNγ, secreted by T helper 1 and CTLs, plays a critical role in tumour immune surveillance. Total cell numbers in the inguinal lymph node (LN) draining the LL/2 tumour were increased in Famin$^{\Delta DC}$ compared to Famin$^{WT}$ littermates (FIG. 5B). Stimulating these LN mononuclear cells from LL/2-OVA tumour-carrying Famin$^{WT}$ mice in vitro with the H-2Kb-restricted OVA MHC class I epitope OVA$^{257-264}$ did not increase the number of IFNγ+ cells above the background numbers detected in control-stimulated cells (FIG. 5C). In stark contrast, LN cells from Famin$^{\Delta DC}$ mice elicited a strong OVA$^{257-264}$ IFNγ response (FIG. 5C), indicating that a strong, antigen-specific MHC class I-restricted CD8 T cell response has been elicited. Furthermore, antigen-nonspecific T cell activation via anti-CD3$^+$ anti-CD28 monoclonal antibodies resulted in increased numbers of IFNγ$^+$ LN cells in Famin$^{\Delta DC}$ compared to Famin$^{WT}$ mice (FIG. 5C). Altogether this established that FAMIN function in DCs augmented these cells' ability to prime and promote a tumour-specific T cell response that was associated with profound protection from tumour growth.

Figure 5D:
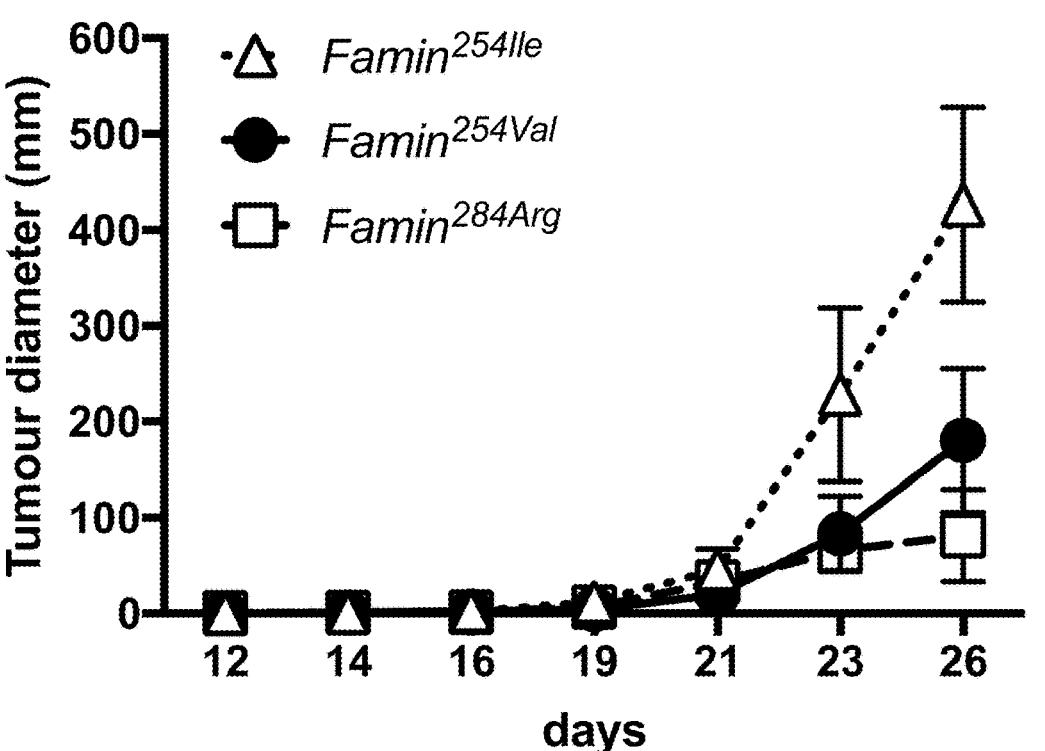
FIGS. 5D and 5E show tumour growth in Famin$^{254Ile}$, Famin$^{254Val}$ and Famin$^{254Arg}$ mice injected subcutaneously with 2.5×10$^4$ LL/2-OVA cells.
Figures 5E, 5F:
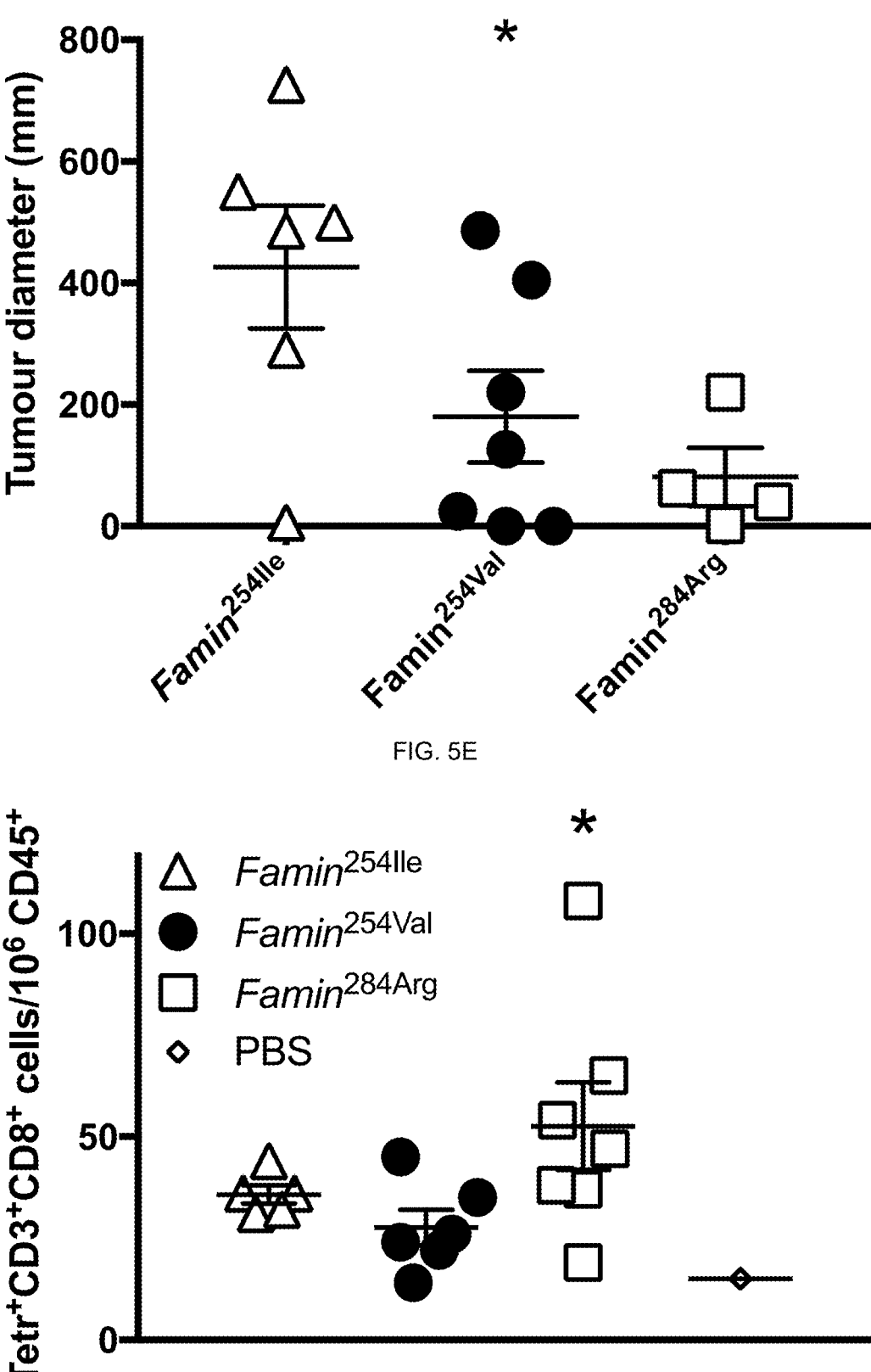
FIGS. 5F and 5G show the proportion of peripheral blood T cells staining positive for an OVA$^{257-264}$ [SIINFEKL (SEQ ID NO: 8)]-loaded tetramer in Famin$^{254Ile}$, Famin$^{254Val}$ and Famin$^{254Arg}$ mice 12 days (FIG. 5F) and 19 days (FIG. 5G) after subcutaneous injection with 2.5×10$^4$ LL/2-OVA cells.
Figure 5G:
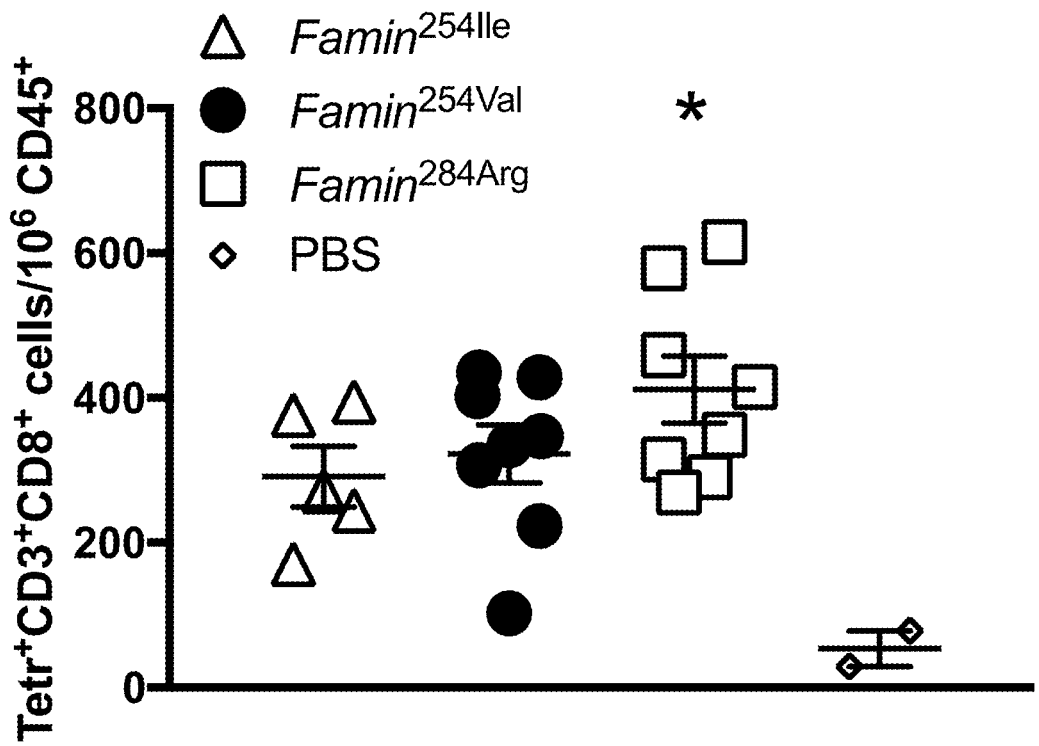

To additionally investigate contribution of FAMIN function in other cell types, and in particular its organism-wide decreased (FAMIN$^{254Val}$) and absent (FAMIN$^{284Arg}$) function, we studied the LL2/OVA model in mice carrying hypomorphic and loss-of-function variants in their germline. Mice were subcutaneously injected with 2.5×10$^4$ syngeneic LL2/OVA tumour cells. The smallest tumours were observed in Famin$^{284Arg}$ mice, which express a loss-of-function variant (FIG. 5D,E). Compared to Famin$^{254I}$ mice, which express the fully functional human 'wild-type' variant, tumour size was also smaller in mice expressing hypomorphic FAMIN$^{254V}$ that has reduced activity (FIG. 5D,E). Lower tumour burden was associated with increased numbers in peripheral blood of CD8$^+$ T cells staining positive with OVA$^{257-264}$ [SIINFEKL (SEQ ID NO: 8)]-loaded tetramer (FIG. 5F,G), even at time points when tumours were not yet macroscopically detectable. These data showed that reduced FAMIN function in the whole organism augments a tumour cell-specific protective immune response and causes decreased tumour growth.

Figure 5H:
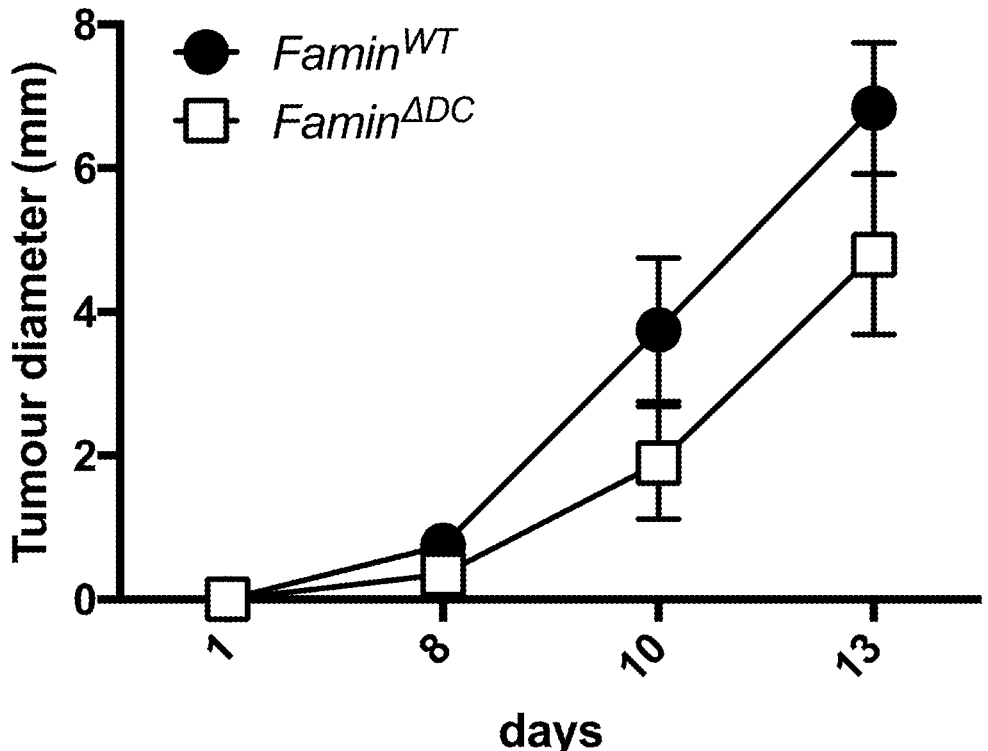
FIGS. 5H and 5I show the tumor size and tumour-free survival of Famin$^{\Delta DC}$ and Famin$^{WT}$ mice subcutaneously injected with 1×10$^5$ EL4-OVA cells.
Figure 5I:
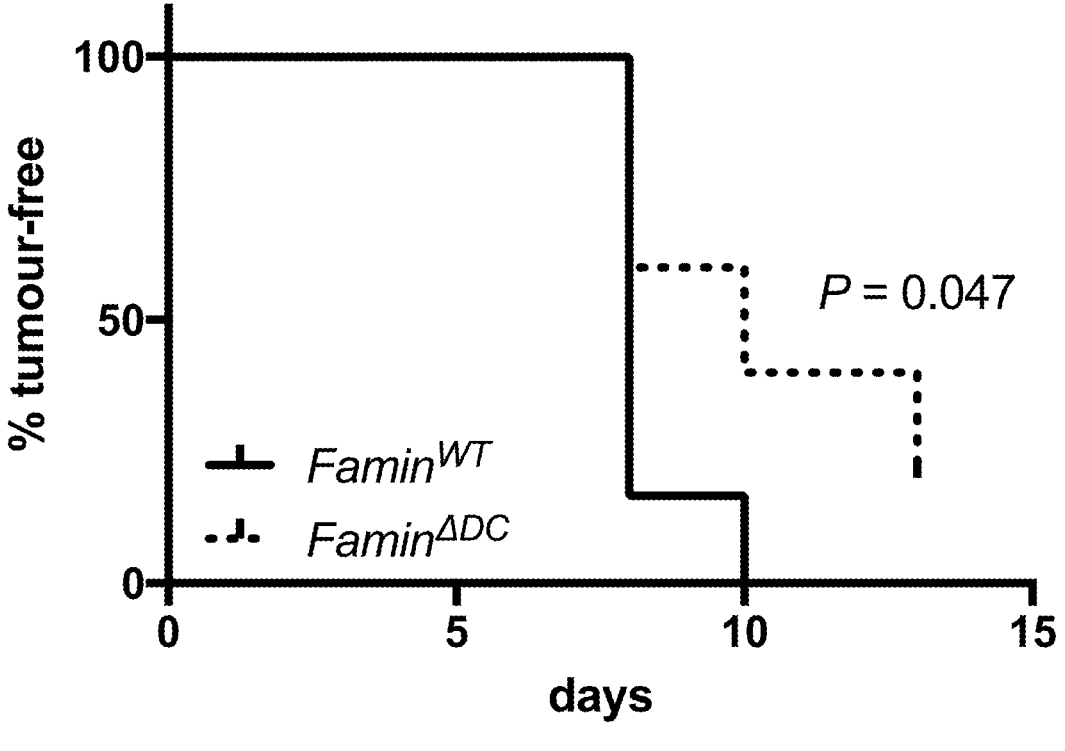

Protection from tumour growth was also observed in Famin$^{ΔDC}$ compared to Famin$^{WT}$ mice when subcutaneously injected with other tumour cell lines, such as 1×10$^5$ EL4-OVA cells, as reflected in smaller tumour sizes (FIG. 5H) and increased tumour-free survival (FIG. 5I).

Deletion of FAMIN Protects from Colitis-Associated Tumourigenesis

Figure 6:
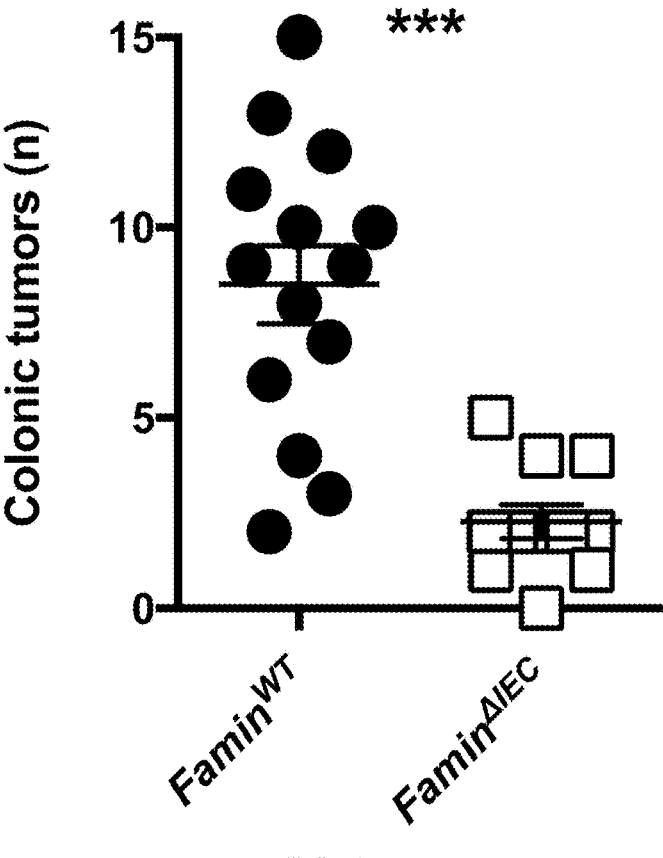
FIG. 6 shows the number of colonic tumours induced in a colitis-associated (azoxymethane/dextran sodium sulfate) cancer model in mice with an intestinal epithelial cell (IEC)-specific deletion of Famin relative to wild-type litter mate controls.

Long-standing inflammation, in individual organ systems or systemically, poses a substantial risk for tumourigenesis. Colitis-associated cancer (CAC), which may develop in long-standing inflammatory bowel disease (IBD), has served as a paradigm for the relationship between inflammation and tumourigenesis [2,3]. CAC can be modelled in rodents by the administration of a mutagen (azoxymethane), followed by the sequential administration of three cycles of dextran sodium sulfate (DSS), which induces intestinal inflammation. We hypothesized that FAMIN function in intestinal epithelial cells (IECs) may impact on CAC. We therefore crossed Villin-Cre transgenic mice with mice harbouring a floxed Famin allele, to generate mice with an IEC-specific deletion of Famin (Vil-Cre$^{pos}$;Famin$^{fl/fl}$ mice; "Famin$^{Δ/EC}$"). Compared to wild-type littermate controls (Vil-Cre$^{neg}$;Famin$^{fl/fl}$, "Famin$^{wt}$"), Famin$^{Δ/EC}$ mice exhibited a 73% reduction in the number of colonic tumours (FIG. 6).

Deletion of FAMIN Protects from Spontaneous Intestinal Tumours

Figure 7:
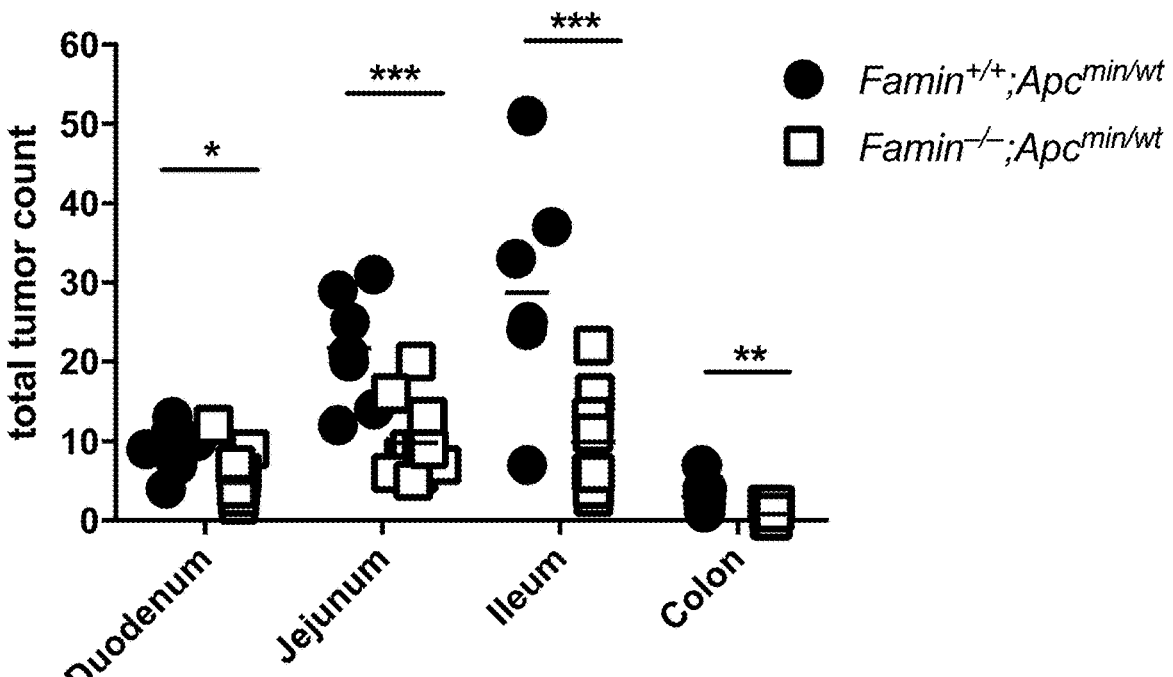
FIG. 7 shows the number of intestinal tumours induced in Famin deficient Apc mutant mice compared to Apc mutant mice with wild-type Famin.

Inactivating mutations in the Adenomatous Polyposis Coli (APC) gene are very common and a rate-limiting step in the adenoma-carcinoma sequence leading to colorectal cancer (CRC) [4]. Germline mutations in APC cause familial adenomatous polyposis. APC-associated CRC can be modelled by Apc mutant mice [5]. To test the hypothesis that FAMIN may impact on CRC formation, we crossed mice with a germ-line mutant Famin$^{-/-}$ allele with Apc$^{min}$ mice. Apc$^{min}$ mice predominantly develop small intestinal tumours, despite modelling human CRC 5. FIG. 7 depicts a profound reduction in tumour numbers in Famin$^{-/-}$;Apc$^{min}$ mice compared to Famin$^{+/+}$; Apc$^{min}$ controls, with a 65% reduction observed in the ileum.

Reduced FAMIN Function Decreases Proliferation in Tumour Cell Lines

Figure 8A:
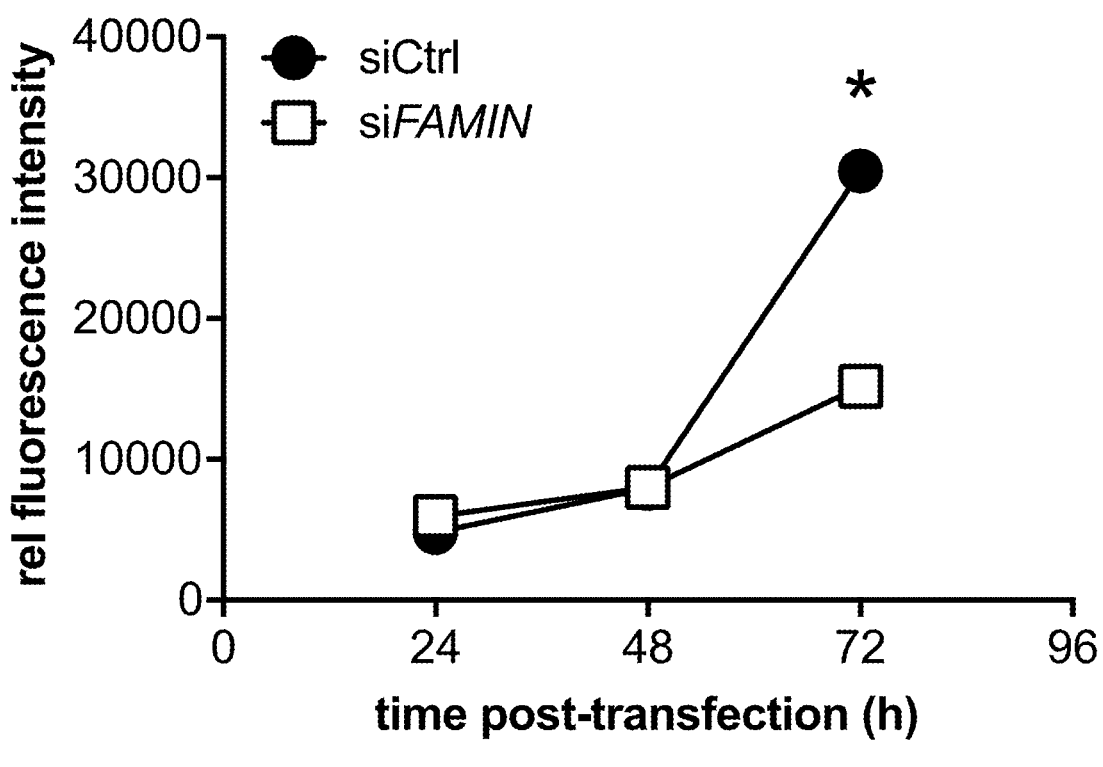
FIG. 8A shows proliferation of human hepatocellular carcinoma cell line HepG2 following knock-down of FAMIN expression via transient siRNA transfection, as measured by CyQuant.
Figure 8B:
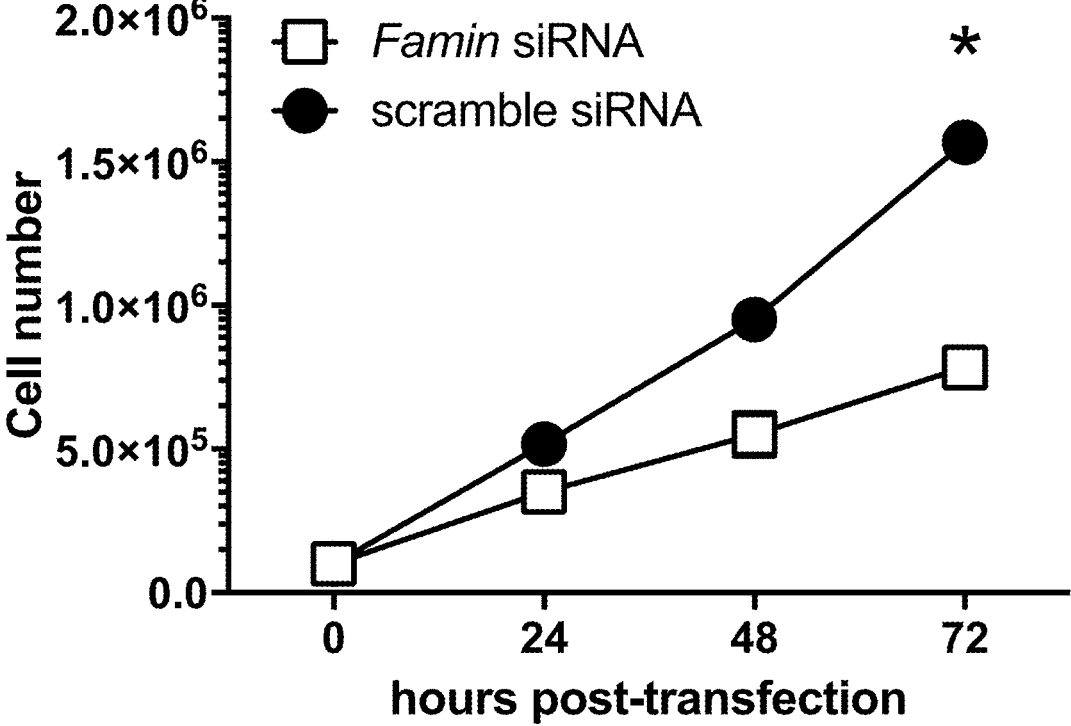
FIG. 8B shows proliferation of the murine B16-F10 melanoma cell line following knock-down of Famin expression via transient siRNA transfection, as measured by CyQuant.

Knock-down of FAMIN expression via transient siRNA transfection of the human hepatocellular carcinoma cell line HepG2 resulted in reduced proliferation compared to control-siRNA-transfected cells as measured by CyQuant (FIG. 8A). Similarly, knock-down of Famin in the murine B16-F10 melanoma cell line resulted in reduced proliferation compared to control siRNA transfected cells (FIG. 8B).

Reduced FAMIN Function Augments T Cell Responses Against Pathogens

Figures 9A, 9B:
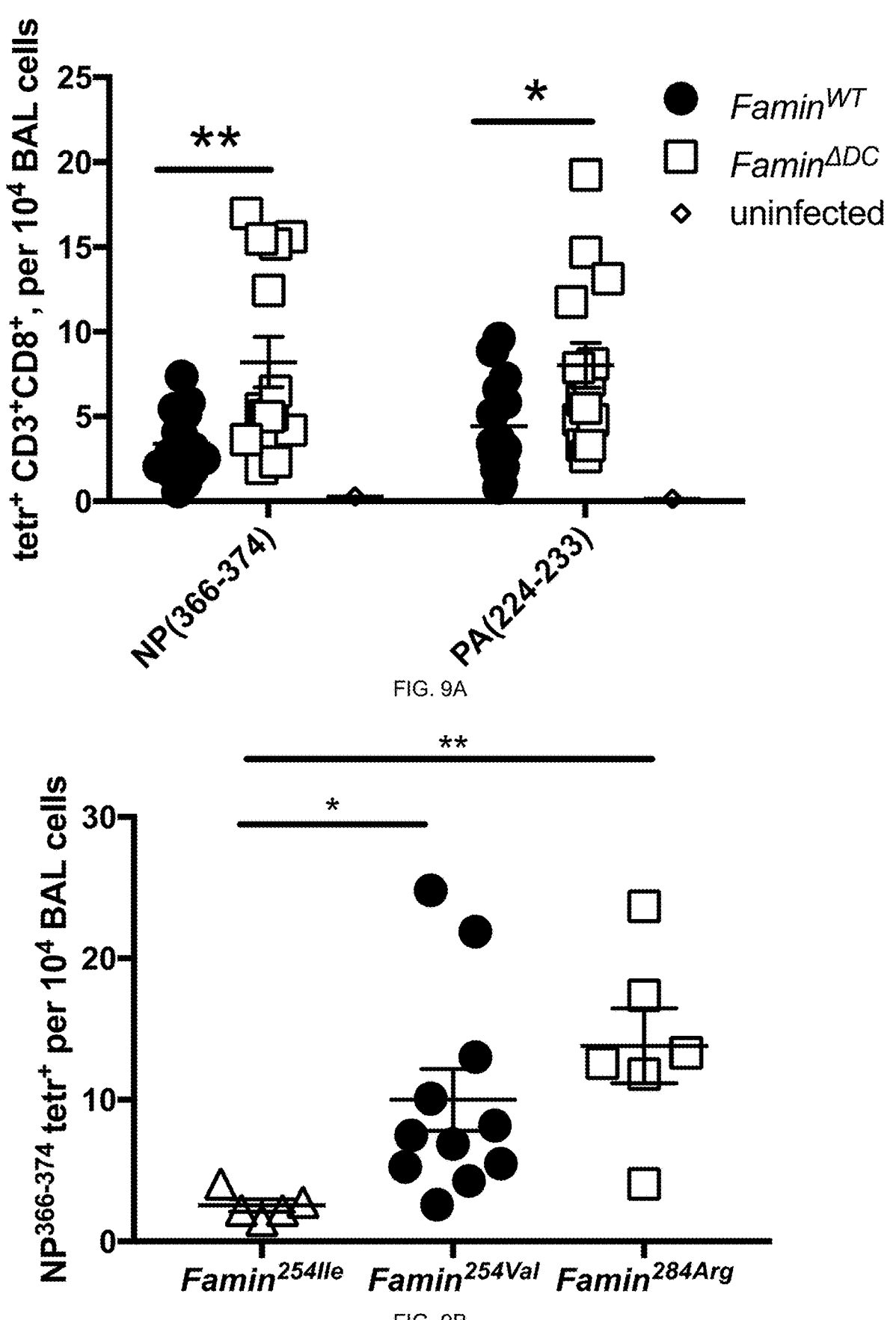
FIG. 9A shows influenza-specific T cell responses in the bronchoalveolar lavage (BAL) of mice with Famin deletion in CD11c$^+$ DCs (Famin$^{\Delta DC}$) and their corresponding wild-type controls (Famin$^{WT}$) 7 days after infection with 10$^4$ plaque forming units (PFU) of influenza A virus (strain A/X-31).
FIG. 9B shows the numbers of CD8$^+$ MHC I-restricted T cells specific for the influenza NP$^{366-374}$ peptide in the bronchoalveolar lavage (BAL) of mice with germ-line variants of FAMIN 6 days after infection with 10$^4$ plaque forming units (PFU) of influenza A virus (strain A/X-31).

To assess whether the increased T cell priming activity caused by decreased FAMIN activity as observed in reductionistic model systems using OVA and tumour immune surveillance models also extends to infectious disease, we infected mice with influenza A virus. Mice with Famin deletion in CD11c$^+$ DCs (Famin$^{ΔDC}$) and their corresponding wild-type controls (Famin$^{WT}$) were infected with 10$^4$ plaque forming units (PFU) of influenza A virus (strain A/X-31). Influenza-specific T cell responses in bronchoalveolar lavage (BAL) were measured on day 7 of infection with MHC I tetramers loaded with NP$^{366-374}$ and PA$^{224-233}$ peptides (FIG. 9A). Decreased FAMIN activity in DCs resulted in increased influenza A-specific T cell responses in BAL. In a similar experiment, mice carrying germ-line variants of FAMIN were infected with influenza A/X-31 strain, and numbers of CD8$^+$ MHC I-restricted T cells specific for the influenza NP$^{366-374}$ peptide measured in BAL on day 6 of infection (FIG. 9B). This demonstrated that hypomorphic (Famin$^{254Val}$) and loss-of-function (Famin$^{283Arg}$) resulted in increased T cell responses compared to Famin$^{284Ile}$.

FAMIN is a Purine Nucleoside Metabolising Enzyme

Figure 10A:
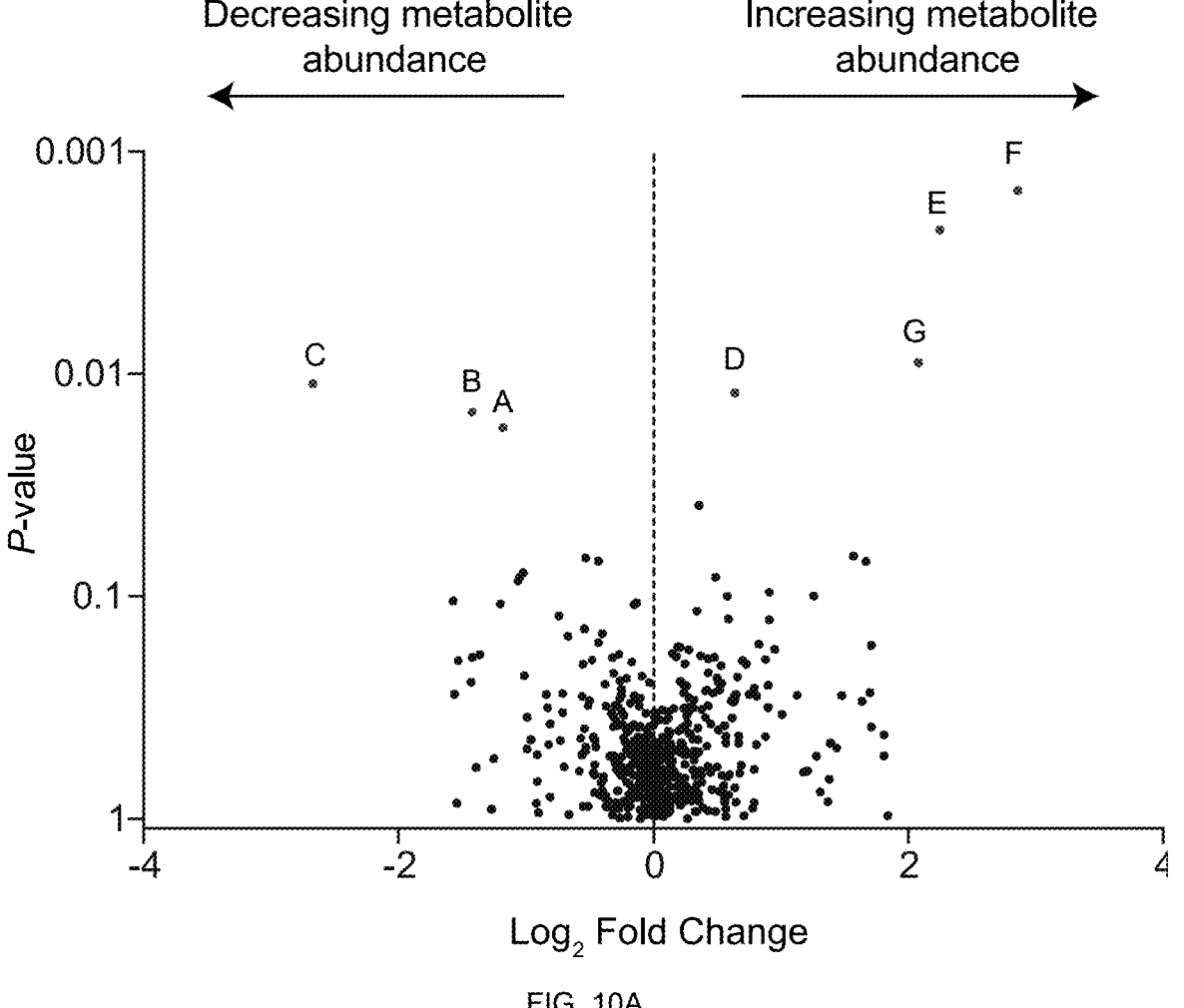
FIG. 10A shows the change in relative metabolite levels in a metabolomic library containing >25,000 liquid chromatography—mass spectrometry (LC-MS) features after incubation with either 10 µg recombinant FAMIN or protein buffer control, in 100 µl phosphate-buffered saline (PBS) for 1 h at 37° C. The metabolomic library consisted of aqueous extracts of methanol: choloroform (Folch method) extracted HepG2 cells. Volcano plot with unadjusted P value and log 2 fold change, grey dots labelled with letters indicate compounds whose abundance significantly decreased (candidate substrates; 'A'-'C') or increased (candidate products; 'D'-'F') in the presence of FAMIN (n=3 independent reactions). 'A' was unambiguously identified as adenosine, 'B' as guanosine, 'C' as inosine, 'D' as hypoxanthine, 'E' as guanine, 'F' as ribose-1-phosphate, and 'G' as xanthine.

We used quantitative, high-sensitivity and high-resolution orthogonal liquid chromatography mass spectrometry (LC-MS) methodology to capture and accurately resolve a wide range of chemically highly diverse metabolites in a metabolomic library constituting the aqueous phase of Folch-extracted cell culture extracts. This strategy was used to search for enzyme function by incubating this complex metabolomic library with recombinant highly purified FAMIN protein. FIG. 10A shows the change in relative metabolite levels in a metabolomic library encompassing >25,000 mass spectrometry features after incubation with either 10 μg recombinant FAMIN or protein buffer control, in 100 μl phosphate-buffered saline (PBS) for 1 h at 37° C. Volcano plot with unadjusted P value and log 2 fold change, grey dots labelled with letters indicate compounds whose abundance significantly decreased (candidate substrates; 'A'-'C') or increased (candidate products; 'D'-'F') in the presence of FAMIN. 'A' was unambiguously identified as adenosine, 'B' as guanosine, 'C' as inosine, 'D' as hypoxanthine, 'E' as guanine, 'F' as ribose-1-phosphate, and 'G' as xanthine. This strongly suggested that FAMIN metabolises purine nucleosides and generates purine nucleobases and ribose-1-phosphate. Experiments with pure substrate and recombinant FAMIN established that FAMIN has enzymatic activity and acts as adenosine deaminase (FIG. 10B), adenosine phosphorylase (FIG. 10C), purine nucleoside phosphorylase (FIG. 10D) and methylthioadenosine phosphorylase (FIG. 10E).

Small Molecule Inhibition of FAMIN

Figure 11A:
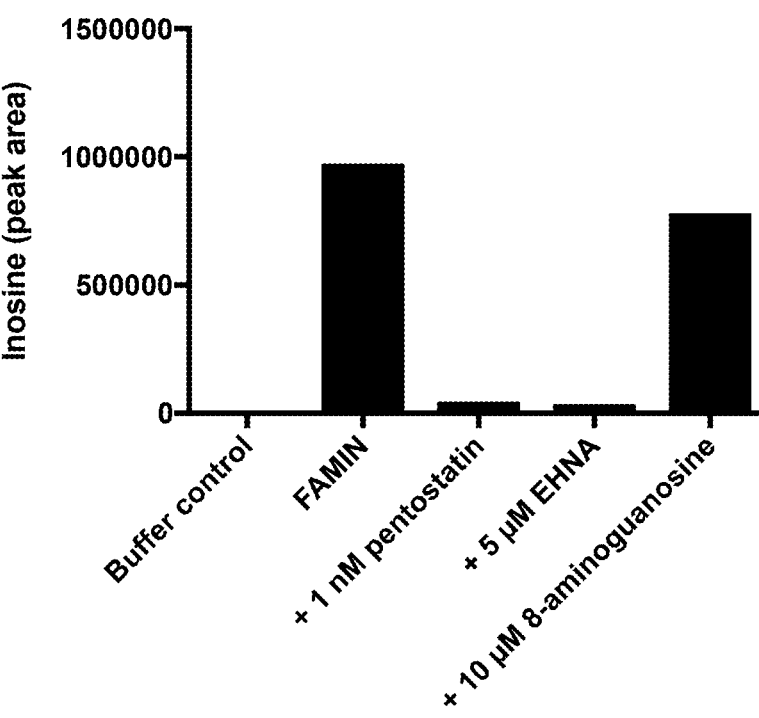
FIG. 11A shows levels of inosine after incubating 10 µg recombinant FAMIN or buffer control with 10 µM adenosine in PBS for 1 h at 37° C. in the presence or absence of pentostatin, erythro-9-(2-hydroxy-3-nonyl) adenine (EHNA), and 8-aminoguanosine at the indicated concentrations.
Figure 11B:
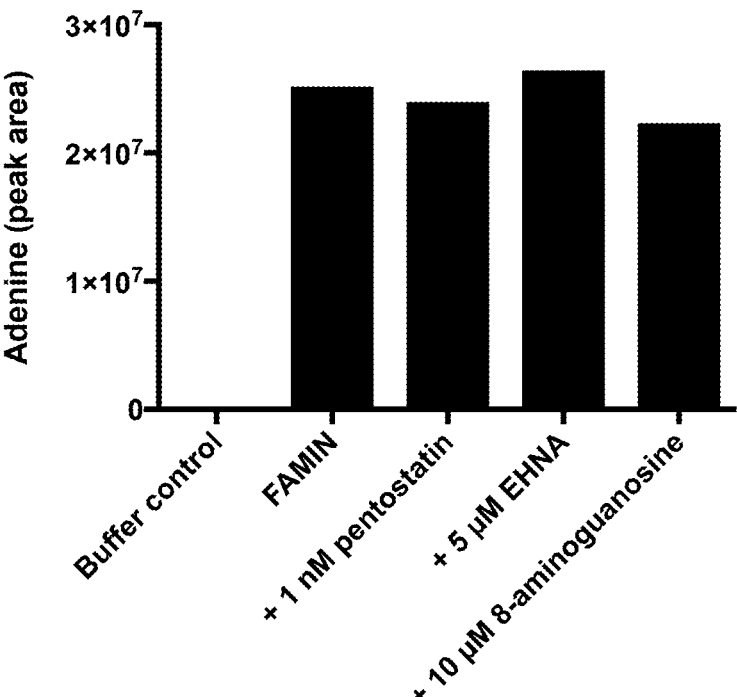
FIGS. 11B and 11C show levels of adenine and ribose-1-phosphate (R-1-P) in the reaction described in FIG. 11A.
Figure 11C:
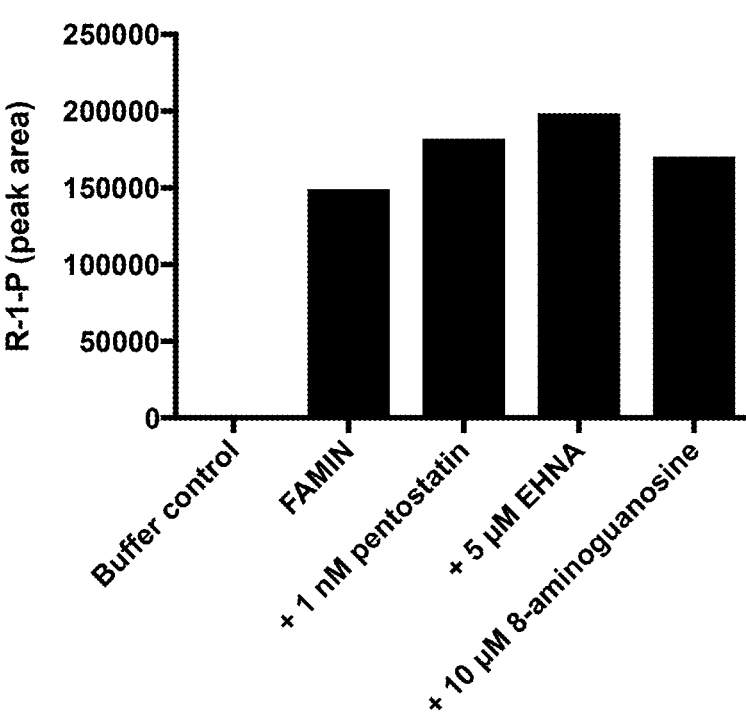
Figure 11D:
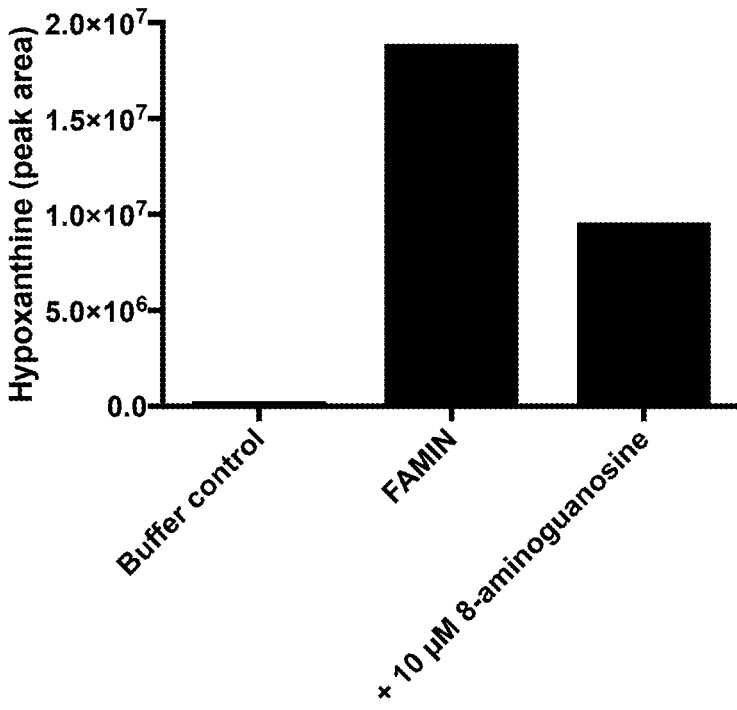
FIG. 11D shows levels of hypoxanthine after incubating 10 µg recombinant FAMIN or buffer control with 10 µM inosine in PBS for 1 h at 37° C. in the presence or absence of 8-aminoguanosine.
Figure 11E:
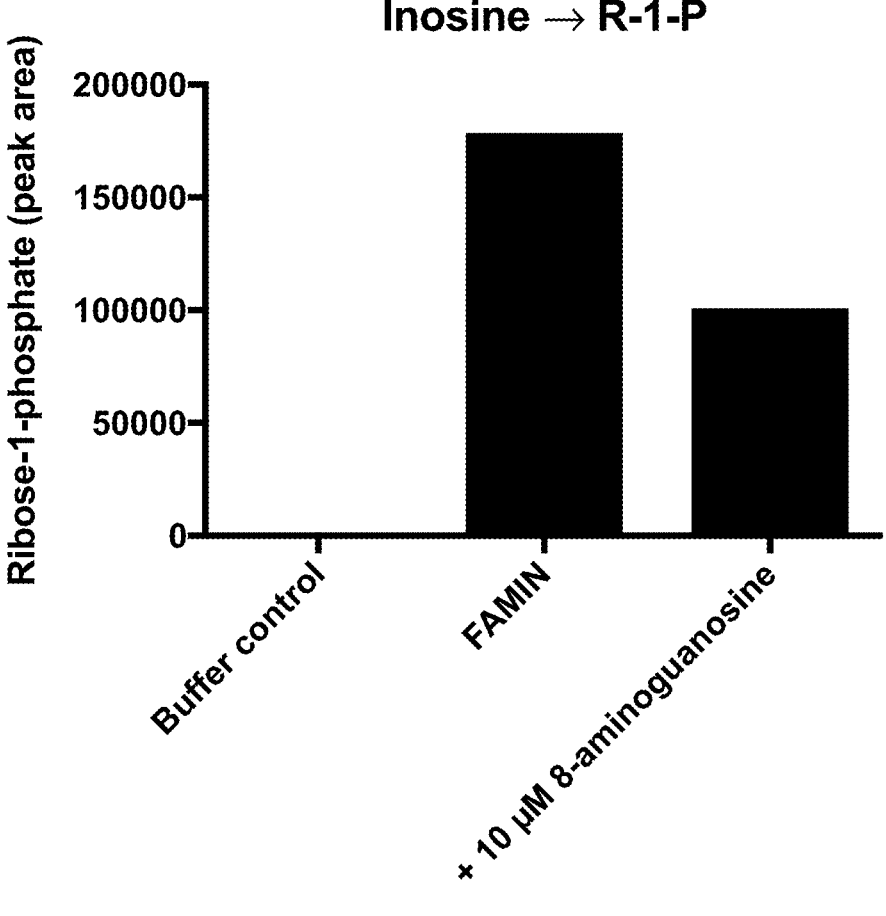
FIG. 11E shows R-1-P levels in the reaction described in FIG. 11D.

Pentostatin (PubchemID 439693, CAS ID 53910-25-1) and EHNA (erythro-9-(2-hydroxy-3-nonyl) adenine; PubchemID 3206. CAS ID 59262-86-1) were found to inhibit FAMIN's adenosine deaminase activity, preventing the generation of inosine from adenosine (FIG. 11A, B, C). 8-aminoguanosine (PubchemID 96849, CAS ID 3868-32-4) was found to be active on FAMIN's purine nucleoside phosphorylase activity (FIG. 11D, E), while leaving FAMIN's adenosine phosphorylase activity intact (FIG. 11B, C). This demonstrates that small molecule inhibition can be used to inhibit FAMIN function.

REFERENCES

1. Cader, M. Z. et al. *Nat. Immunol.* 17, 1046-1056 (2016).

2. Grivennikov, S. I., Greten, F. R. & Karin, M. *Cell* 140, 883-899 (2010).

3. Mantovani, *A. Curr. Mol. Med.* 10, 369-373 (2010).

4. Kinzler, K. W. & Vogelstein, B. *Cell* 87, 159-170 (1996).

5. Moser, A. R., Pitot, H. C. & Dove, W. F. *Science* 247, 322-324 (1990).

6. Wakil, S. M. et al *Arthritis Rheumatol.* 67, 288-295 (2015).

7. Patel, N. et al. *Gut* 63, 1831-1832 (2014).

8. Liu, H. et al. *Nat. Genet.* 47, 267-271 (2015).

9. Jostins, L. et al. *Nature* 491, 119-124 (2012).

The invention claimed is:

1. A method of decreasing the proliferation of tumour cells comprising;

contacting the cells with a suppressor nucleic acid or targeted nuclease that reduces expression of active FAMIN polypeptide, wherein the active FAMIN polypeptide comprises an amino acid sequence at least 95% identical to SEQ ID NO: 1 over the whole length of SEQ ID NO: 1, wherein the suppressor nucleic acid comprises a contiguous sequence of 15 to 40 nucleotides of a nucleotide sequence at least 95% identical to SEQ ID NO: 2 or its complement.

2. The method according to claim 1 wherein the suppressor nucleic acid is a siRNA or shRNA.

3. The method according to claim 1 wherein the suppressor nucleic acid is an antisense oligonucleotide.

4. The method of claim 1 wherein the active FAMIN polypeptide comprises the amino acid sequence of SEQ ID NO: 1.

5. The method of claim 1 wherein the suppressor nucleic acid comprises a contiguous sequence of 15 to 40 nucleotides of SEQ ID NO: 2 or its complement.

6. The method according to claim 1 wherein the suppressor nucleic acid is administered in combination with an additional therapeutic agent.

7. The method according to claim 6 wherein the additional therapeutic agent is an immune checkpoint inhibitor.

8. The method according to claim 6 wherein the additional therapeutic agent is an anti-cancer agent.

* * * * *

SEQUENCE LISTING

<160> NUMBER OF SEQ ID NOS: 8

<210> SEQ ID NO 1
<211> LENGTH: 430
<212> TYPE: PRT
<213> ORGANISM: Homo sapiens

<400> SEQUENCE: 1

```
Met Ala Glu Ala Val Leu Ile Asp Leu Phe Gly Leu Lys Leu Asn Ser
1               5                   10                  15

Gln Lys Asn Cys His Gln Thr Leu Leu Lys Thr Leu Asn Ala Val Gln
            20                  25                  30

Tyr His His Ala Ala Lys Ala Lys Phe Leu Cys Ile Met Cys Cys Ser
        35                  40                  45

Asn Ile Ser Tyr Glu Arg Asp Gly Glu Gln Asp Asn Cys Glu Ile Glu
    50                  55                  60

Thr Ser Asn Gly Leu Ser Ala Leu Leu Glu Glu Phe Glu Ile Val Ser
65                  70                  75                  80

Cys Pro Ser Met Ala Ala Thr Leu Tyr Thr Ile Lys Gln Lys Ile Asp
                85                  90                  95

Glu Lys Asn Leu Ser Ser Ile Lys Val Ile Val Pro Arg His Arg Lys
            100                 105                 110

Thr Leu Met Lys Ala Phe Ile Asp Gln Leu Phe Thr Asp Val Tyr Asn
            115                 120                 125

Phe Glu Phe Glu Asp Leu Gln Val Thr Phe Arg Gly Gly Leu Phe Lys
        130                 135                 140

Gln Ser Ile Glu Ile Asn Val Ile Thr Ala Gln Glu Leu Arg Gly Ile
145                 150                 155                 160

Gln Asn Glu Ile Glu Thr Phe Leu Arg Ser Leu Pro Ala Leu Arg Gly
                165                 170                 175

Lys Leu Thr Ile Ile Thr Ser Ser Leu Ile Pro Asp Ile Phe Ile His
            180                 185                 190

Gly Phe Thr Thr Arg Thr Gly Gly Ile Ser Tyr Ile Pro Thr Leu Ser
            195                 200                 205

Ser Phe Asn Leu Phe Ser Ser Ser Lys Arg Arg Asp Pro Lys Val Val
        210                 215                 220

Val Gln Glu Asn Leu Arg Arg Leu Ala Asn Ala Ala Gly Phe Asn Val
225                 230                 235                 240

Glu Lys Phe Tyr Arg Ile Lys Thr His His Ser Asn Asp Ile Trp Ile
                245                 250                 255

Met Gly Arg Lys Glu Pro Asp Ser Tyr Asp Gly Ile Thr Thr Asn Gln
            260                 265                 270

Arg Gly Val Thr Ile Ala Ala Leu Gly Ala Asp Cys Ile Pro Ile Val
            275                 280                 285

Phe Ala Asp Pro Val Lys Lys Ala Cys Gly Val Ala His Ala Gly Trp
        290                 295                 300

Lys Gly Thr Leu Leu Gly Val Ala Met Ala Thr Val Asn Ala Met Ile
305                 310                 315                 320

Ala Glu Tyr Gly Cys Ser Leu Glu Asp Ile Val Val Val Leu Gly Pro
                325                 330                 335

Ser Val Gly Pro Cys Cys Phe Thr Leu Pro Arg Glu Ser Ala Glu Ala
            340                 345                 350

Phe His Asn Leu His Pro Ala Cys Val Gln Leu Phe Asp Ser Pro Asn
        355                 360                 365
```

-continued

```
Pro Cys Ile Asp Ile Arg Lys Ala Thr Arg Ile Leu Leu Glu Gln Gly
    370             375             380

Gly Ile Leu Pro Gln Asn Ile Gln Asp Gln Asn Gln Asp Leu Asn Leu
385             390             395             400

Cys Thr Ser Cys His Pro Asp Lys Phe Phe Ser His Val Arg Asp Gly
            405             410             415

Leu Asn Phe Gly Thr Gln Ile Gly Phe Ile Ser Ile Lys Glu
            420             425             430

<210> SEQ ID NO 2
<211> LENGTH: 4288
<212> TYPE: DNA
<213> ORGANISM: Homo sapiens

<400> SEQUENCE: 2
agacctgcag ctcctgccgc cctgcgcccg ctcccagggc ccgtcgttcc gccgccctat        60
ccctcctcaa ggggcccta gctgcctcct cgcgacccctt tccggactcg gcctgcccac       120
tcctgcccgc taacccgcct ggctcccggg cgagagccct cgcgcggctc tggttcctgt       180
tcctctaacg ccgccggggc tgcgggatgc cgactccgcg gaccgcccag acccggaact       240
gctgaggcag cagcgggctc gcggcgcttg gctcatcccg ggattcccca gctctcgcgc       300
tgggcccgcc gcgttcgcac caagcacgcc aggcggccct ggcctacctc cctcccgcct       360
cccggcagct ggcacgaggg aacctggccg tcaggtttcc cctgggatcc tgggacggta       420
tcaggcgggg aatctgtgcg gccgcggcga ggtgatttat ttggcataaa agtattcttt       480
caaggatggc agaagctgtt ttgattgatc tttttggttt gaaattgaac tctcaaaaaa       540
actgccatca gacattactg aagactttga atgctgtcca ataccaccat gctgccaagg       600
ccaagtttct ctgtataatg tgttgcagta acatcagcta tgaaagggat ggagaacaag       660
ataattgtga aatagaaaca agcaatggat tatcagctct cttggaagaa tttgagattg       720
ttagctgtcc cagcatggct gccactttgt ataccattaa acagaaaatt gatgaaaaaa       780
atctgagcag cattaaggta attgtaccca ggcacaggaa gacattaatg aaagctttta       840
ttgatcaact cttcactgat gtttacaatt ttgaatttga agatttgcaa gtgactttta       900
ggggagggct ttttaaacag tccattgaaa taaacgtaat cacagctcaa gaactaagag       960
gaattcagaa tgaaatagaa acattttttga gaagtctgcc agcactgaga ggaaaattaa      1020
ctattatcac ttcttctttg atcccagata ttttcataca tggatttact acaagaacag      1080
gtgggatatc ttatatacca actcttagct cattcaatct cttcagtagt tccaaacgga      1140
gagatcccaa ggtagtggtt caagaaaatc tgcgtaggtt ggcgaatgct gcaggattta      1200
atgtggagaa attttaccga ataaagactc atcattccaa tgacatctgg attatgggaa      1260
gaaaggagcc tgactcttat gatggaataa ccacaaatca gagaggagtc acaatagcag      1320
ctcttggtgc agactgtata ccgatagttt ttgcagatcc agtcaaaaaa gcatgtgggg      1380
ttgctcacgc tggttggaaa ggtactttgt gggtgttgc tatggctaca gtgaatgcta      1440
tgatagcaga atatggctgc agtttggaag acattgttgt tgtacttgga ccttcagtag      1500
gaccttgctg tttttactctt ccaagggaat cagcagaggc atttcataat cttcatcctg      1560
catgtgtaca actatttgat tcaccaaatc cctgtatcga catccgtaaa gccacaagga      1620
ttcttctaga acaggagga attcttccac agaatattca ggaccagaac caagatctca      1680
acctctgtac atcttgccat cctgacaagt ttttctccca tgtccagat ggccttaatt      1740 ttggtacaca gattggcttc atatcaatta agaatgaga tacttgactg gattttttgta      1800
```

```
taactgcttc ctgcctcctt ccaaactgac tgcaagagag aaatttagct gtttgattta       1860
cttaaaacca aatggattac aatggataat tcatcttttg ggtatatttt tactattatt       1920
caaagccaaa tgattttcat ttaattgtaa taataactga caaaaatcag tatgttgtag       1980
ctaatatgtt ttatgcatga gaattattct taaagtttgt tctccctgtt tattacacag       2040
atcaggaata gatttgttca gttcagtatt tattggatac cctctattgg tcaggcattg       2100
tgttaagcat atgtgaatca aaatgaacac aacttttccc tttgagtctg atacagtgaa       2160
ggagataaac acttctacaa cttaaattta attttaatag cagtagaaga gaacataagg       2220
aatagaggtt aattttaccc agaagcagga tagagaaaat attacagaga aaatcacata       2280
tcacatgggc tcgaaagatg tagaggtttt tgacaaatga agaacaacca taacaggtag       2340
agggaacacc atgaaccagg gcatgaaact gaaagtgcat aacatattct agagagagaa       2400
gggtgtgggc atgagttagg gctggaaaaa caggttggaa acagataagt aagggtctca       2460
aatgcaatgt caaagagctt gcagtttatt ttccaggcaa tgagtaggca gccaaaaaaa       2520
aaaaagtaag gatgtttttt tttttttttcc catggcatca tatttaagag gatggattta       2580
aattgtgtga gaccaaagca tagagactag ataagaggcg atcaaaatat ttcaaaaaga       2640
aataatgaag atccaatgaa ggaagtggaa attaaaatag ggaagagagt agatggatta       2700
gagagacatt taagagatgg aatcaataga tcctgttact agataatgga agtaagaggt       2760
gaggaagagt ggaaaagtca ttaatgactc taagatttct gcttggctgc ttaccaagat       2820
tggcaacaaa gggaggggaga aggtttggaa aaagagagaa ggataatgag tttgacttta       2880
catagaatga agggcatcca gatagaaatc tttggttaat aattagaaat atagacctag       2940
aaattaggag gaaacctgag acagagacaa atatttcaaa gcttacaata cagagatgat       3000
acctgattct attggagcag gtttgatcat ctaggcagaa attaggatga gaaaaaagga       3060
gatccaataa tacaacctta tagtcacaga agtaagaaaa aaagggtagt tgttttgaag       3120
aagccaggat aggtgtggaa agtactcaaa aagaaatctt cagggataaa ataaagtgat       3180
aatttaaaag aaatcaatgg attaaacata ttgaaactgt tctataggca gtggtcattg       3240
agtcagcttt cagtgcatta ggaagaagat gcataggtgt caactctttt ctgacagcat       3300
ttactagaga agagaaaaag ctggggacta catcttcaag gaagggactt tttttggatg       3360
agcagttttg agtgtgtttg tcagttaaag agaggaatta ggttagtttt catttgggaa       3420
aaattgtata tatatttaat gtaagttatc acattgcatc ttaaaaatat tcttatttaa       3480
tacatatatt tcctacatgt atatgtggta gcatgatagc aaataacatt tgtttggtat       3540
ttccaaagga ctttcatgta cattgcctca ttttaccttt acagctactc tgaaatacac       3600
aggcattatc cctttattc agctgagaaa actgagcttc attgaggtgg aggtcaaaaa       3660
tcacaaaatt tgtgatgaat taagatttga acatatgttt tgtgactcca gttttccttt       3720 cagatttttaa aattaattaa agggatcttc attatacttt tattgttaac tttttgttaa       3780
cataatttat tcatacattc agtgaaaatt ttgttgaggt actgggacag gttaaaaaat       3840
acagttgtag ccctcaggat atttaatatc cagtgaaaag tgacagtcag taaaccaaca       3900
atctcaatac tttgatatat gttgtgaggt tgtgataacc gattcttgtt tagtttaatt       3960
ctatatctcc cttagaccag tgttaaattt aaataaaaca cctcattttt tccaattcag       4020
ggaaggcact aaacataaag cataggatag aaatgttgaa ctcatccaaa atattatttt       4080
gtttaatgaa aatgatgaag attaaggaat acttccatgt attgagtaag gttgataatt       4140
```

```
ttctaattct tcactgtgca ttattttgtt tgaagttggt aaatttggag tatcctgcag   4200
acacattttg ctttatgtac tacaacattc tacaaccaaa taaaaattat tttgattatc   4260
tgaaaaaaaa aaaaaaaaaa aaaaaaa                                       4288

<210> SEQ ID NO 3
<211> LENGTH: 19
<212> TYPE: RNA
<213> ORGANISM: Artificial Sequence
<220> FEATURE:
<223> OTHER INFORMATION: suppressor nucleic acid siRNA

<400> SEQUENCE: 3
ucagagagga gucacaaua                                                       19

<210> SEQ ID NO 4
<211> LENGTH: 19
<212> TYPE: RNA
<213> ORGANISM: Artificial Sequence
<220> FEATURE:
<223> OTHER INFORMATION: suppressor nucleic acid siRNA

<400> SEQUENCE: 4
acggagagau cccaaggua                                                       19

<210> SEQ ID NO 5
<211> LENGTH: 19
<212> TYPE: RNA
<213> ORGANISM: Artificial Sequence
<220> FEATURE:
<223> OTHER INFORMATION: suppressor nucleic acid siRNA

<400> SEQUENCE: 5
gaucucaacc ucuguacau                                                       19

<210> SEQ ID NO 6
<211> LENGTH: 19
<212> TYPE: RNA
<213> ORGANISM: Artificial Sequence
<220> FEATURE:
<223> OTHER INFORMATION: suppressor nucleic acid siRNA

<400> SEQUENCE: 6
gacuguauac cgauaguuu                                                       19

<210> SEQ ID NO 7
<211> LENGTH: 17
<212> TYPE: PRT
<213> ORGANISM: Artificial Sequence
<220> FEATURE:
<223> OTHER INFORMATION: OVA MHC class II epitope

<400> SEQUENCE: 7

Ile Ser Gln Ala Val His Ala Ala His Ala Glu Ile Asn Glu Ala Gly
1               5                  10                  15

Arg
```

-continued

```
<210> SEQ ID NO 8
<211> LENGTH: 8
<212> TYPE: PRT
<213> ORGANISM: Artificial Sequence
<220> FEATURE:
<223> OTHER INFORMATION: OVA MHC class I epitope

<400> SEQUENCE: 8

Ser Ile Ile Asn Phe Glu Lys Leu
1               5
```